(12) United States Patent
Tang et al.

(10) Patent No.: US 8,304,411 B2
(45) Date of Patent: *Nov. 6, 2012

(54) DICYCLOAZAALKANE DERIVATES, PREPARATION PROCESSES AND MEDICAL USES THEREOF

(75) Inventors: Peng Cho Tang, Shanghai (CN); Zhigang Lin, Shanghai (CN); Hejun Lu, Shanghai (CN); Fuqiang Zhao, Shanghai (CN); Li Li, Shanghai (CN); Fanglong Yang, Shanghai (CN); Jianghong Fu, Shanghai (CN); Lin Wang, Shanghai (CN); Guangyuan Shen, Shanghai (CN); Dongliang Guan, Shanghai (CN)

(73) Assignees: Jiangsu Hansoh Pharmaceutical Co., Ltd., Lianyungang, Jiangsu (CN); Shanghai Hengrui Pharmaceutical Co. Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 12/863,964

(22) PCT Filed: May 20, 2008

(86) PCT No.: PCT/CN2008/071014
§ 371 (c)(1),
(2), (4) Date: Jul. 21, 2010

(87) PCT Pub. No.: WO2009/094866
PCT Pub. Date: Aug. 6, 2009

(65) Prior Publication Data
US 2010/0311747 A1 Dec. 9, 2010

(30) Foreign Application Priority Data
Jan. 23, 2008 (CN) .......................... 2008 1 0004727

(51) Int. Cl.
| | |
|---|---|
| *A61K 31/5377* | (2006.01) |
| *A61K 31/403* | (2006.01) |
| *A61K 31/454* | (2006.01) |
| *C07D 403/12* | (2006.01) |
| *C07D 401/14* | (2006.01) |
| *C07D 413/14* | (2006.01) |
| *A61P 3/10* | (2006.01) |

(52) U.S. Cl. ..................... 514/235.2; 514/323; 514/414; 544/143; 546/200; 548/468

(58) Field of Classification Search ........................ None
See application file for complete search history.

(56) References Cited

U.S. PATENT DOCUMENTS
| | | | |
|---|---|---|---|
| 5,736,550 A | 4/1998 | Kikuchi et al. | ............... 514/261 |
| 6,110,949 A | 8/2000 | Villhauer | ..................... 514/365 |
| 2005/0130981 A1 | 6/2005 | Aranyl et al. | |
| 2009/0176847 A1 | 7/2009 | Tang et al. | |

FOREIGN PATENT DOCUMENTS
| | | |
|---|---|---|
| CN | 1639159 A | 7/2005 |
| CN | 1798559 | 7/2006 |
| CN | 101050194 A | 10/2007 |
| CN | 101230058 | 7/2008 |
| CN | 101230059 | 7/2008 |
| WO | WO 98/19998 | 5/1998 |
| WO | WO 2006/028961 A2 | 3/2009 |

OTHER PUBLICATIONS

Chapman et al., cpalus an 1959:111795.*
Fairhurst et al., caplus an 2004:857388.*
Hansen, Lene et al., Endocrinology, vol. 140, No. 11, "Glucagon-Like Peptide-1-(7-36) Amide is Transformed to Glucagon-Like Peptide-1-(9-36) Amide by Dipeptidyl Peptidase IV in the Capillaries Supplying the L Cells of the Porcine Intestine".
Barluenga, Jose et al., Chem. Eur. J. 1997, 3. No. 8, "Zirconium-Mediated Intramolecular Coupling of Terminal Alkynes and Their Subsequent Carbonylation: Novel Synthesis of Seven- and Eight-Membered Heterocycles".
Mihovilovic, Marko D. et al., ARKIVOC 2001 (II) 28-33, "Application of dry-state adsorption condition (DSAC) Pauson-Khand cyclization for the synthesis of perhydrocyclopental [c]pyrroles".
Xiao, J. et al. "Quantitative Structure-activity Relationship of Dipeptidyl Peptidase IV Inhibitors" Institute of Materia Medica, Chinese Academy of Medical Sciences and Peking Union Medical College, Beijing, Acta Chimica Sinica, vol. 63 No. 8, 2005 pp. 757-763.
Becker, D. P. and D. L. Flynn, "Studies of the Solid-Phase Pauson-Khand Reaction: Selective in-situ Enone Reduction to 3-Azabicyclo[3.3.0] octanones" Tetrahedron Letters, vol. 34, No. 13, 1993, pp. 2087-2090.

* cited by examiner

*Primary Examiner* — Sun Jae Loewe
(74) *Attorney, Agent, or Firm* — Ryan L. Marshall; Brinks Hofer Gilson & Lione

(57) ABSTRACT

Disclosed are new dicycloazaalkane derivates represented by general formula (I), preparation processes and pharmaceutical compositions containing them, and the uses for treatment especially for dipeptidyl peptidase inhibitor (DPP-IV), in which each substitute group of general formula (I) is as defined in specification.

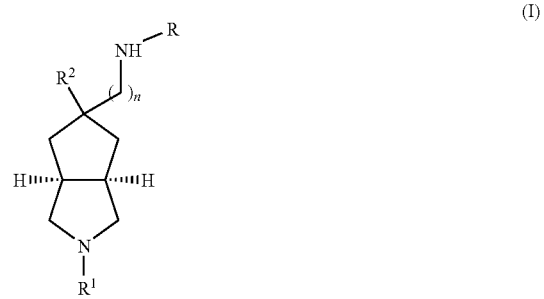

(I)

33 Claims, No Drawings

DICYCLOAZAALKANE DERIVATES, PREPARATION PROCESSES AND MEDICAL USES THEREOF

The present application is the national phase application of PCT Application No. PCT/CN2008/071014, filed May 20, 2008, which claims priority to Chinese Patent Application No. 200810004727.1, filed Jan. 23, 2008, the entireties of both of which are hereby incorporated by references.

FIELD

This disclosure relates to derivatives of azabicyclo alkane, methods for preparing the same, compositions containing the same, and the uses thereof, particularly their pharmaceutical use as inhibitors of dipeptidyl peptidase IV (DPP-IV).

BACKGROUND

Diabetes refers to a disease derived from multiple causative factors and characterized by elevated levels of plasma glucose or hyperglycemia, along with sugar, fat and protein metabolism disorders caused by insulin secretion and/or the action defects. Diabetes is an ancient disease due to the human body absolute or relative lack of insulin, which results in increased concentrations of glucose in the blood. The glucose is largely discharged in urine. High blood levels of glucose can cause several problems, such as excessive thirst, frequent urination, increased appetite, weight loss, dizziness, fatigue, and other symptoms.

Dipeptidyl peptidase-IV (DPP-IV) is a serine protease that cleaves N-terminal dipeptides from a peptide chain containing, preferably, a proline residue in the penultimate position. Although its biological role in mammalian systems has not been completely established, DPP-IV is believed to play an important role in neuropeptide metabolism, T-cell activation, attachment of cancer cells to the endothelium, and the entry of HIV into lymphoid cells (WO98/19998).

More recently, it was discovered that DPP-IV is responsible for inhibiting the secretion of glucagon-like peptide (GLP)-1. More particularly, DPP-IV cleaves the amino-terminal His-Ala dipeptide of GLP-1, degrading active GLP-1 (7-36)$NH_2$ into inactive GLP-1(9-36)$NH_2$ (Endocrinology, 1999, 140: 5356-5363). Under the physiological condition, the half-life of the whole GLP-1 in blood circulation is short, the inactive metabolite from GLP-1 degraded by DPP-IV can combine with GLP-1 receptor to antagonize the active GLP-1, so the physiological response to GLP-1 is shortened. The endogenous even exogenous GLP-1 can be entirely protected by the DPP-IV inhibitor from being deactivated by DPP-IV, and the GLP-1 bioactivity can be significantly increased (5- to 10-fold). Since GLP-1 is a major stimulator of pancreatic insulin secretion and can directly effect on glucose disposal, the DPP-IV inhibitor is well useful for treating non-insulin-dependent diabetes mellitus (NIDDM) (U.S. Pat. No. 6,110,949).

SUMMARY

Accordingly, the present disclosure relates to the compounds of formula (I) or pharmaceutically acceptable salts thereof.

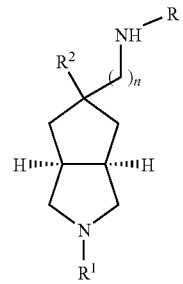

Wherein:

R is selected from the group consisting of alkyl, cycloalkyl, haloalkyl, aryl, heteroaryl, aminocarbonyl alkyl, amide alkyl, heterocyclic carbonyl alkyl, and heterocyclic aminoalkyl, wherein the heterocycle is 5- or 6-membered heterocyclic ring further substituted with one or more groups selected from the group consisting of alkyl, aryl, heteroaryl, haloalkyl, haloalkoxyl, hydroxyl, amino, alkylamino, amido, aminocarbonyl, cyano, alkynyl, alkoxyl, aryloxyl, aminoalkyl, hydroxyalkyl, heterocyclic alkyl, carboxylic acid, carboxylic ester and halogen;

$R^1$ is selected from the group consisting of hydrogen, alkyl, cycloalkyl, heterocyclic alkyl, aryl, heteroaryl, —C(O)$NR^3R^4$, —C(O)$R^3$ and —C(O)$OR^3$, wherein the alkyl, cycloalkyl, heterocyclic alkyl, aryl or heteroaryl is further optionally substituted with one or more groups selected from the group consisting of alkyl, aryl, hydroxyl, amino, alkoxyl, aryloxyl and heterocyclic alkyl;

$R^2$ is selected from the group consisting of hydrogen and alkyl, wherein the alkyl is further substituted with one or more groups selected from the group consisting of cycloalkyl and aryl;

$R^3$ and $R^4$ are each independently selected from the group consisting of hydrogen, alkyl, cycloalkyl, aryl, heteroaryl and heterocyclic alkyl, wherein the alkyl, cycloalkyl, aryl, heteroaryl or heterocyclic alkyl is further optionally substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclic alkyl, heterocyclic alkoxyl, trifluoromethyl, carboxylic acid and carboxylic ester;

$R^3$ and $R^4$ are optionally attached together with the N atom to form a 3- to 8-membered heterocyclic ring, wherein the 5- to 8-membered heterocyclic ring further optionally contains one or more heteroatoms selected from N, O, and S, and the 3- to 8-membered ring is further optionally substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclic alkyl, carboxylic acid, carboxylic ester, halogen and —$NR^3R^4$; and n is an integer from 0 to 4.

Further, the present disclosure includes the compounds of formula (IA) or pharmaceutically acceptable salts thereof.

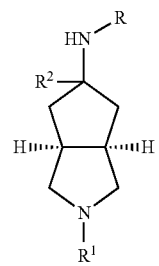

Wherein:

R is selected from the group consisting of alkyl, cycloalkyl, haloalkyl, aryl, heteroaryl, aminocarbonyl alkyl, amide alkyl, heterocyclic carbonyl alkyl, and heterocyclic aminoalkyl, wherein the heterocycle is 5- or 6-membered heterocyclic ring further substituted with one or more groups selected from the group consisting of alkyl, aryl, heteroaryl, haloalkyl, haloalkoxyl, hydroxyl, amino, alkylamino, amido, aminocarbonyl, cyano, alkynyl, alkoxyl, aryloxyl, aminoalkyl, hydroxyalkyl, heterocyclic alkyl, carboxylic acid, carboxylic ester and halogen;

$R^1$ is selected from the group consisting of hydrogen, alkyl, cycloalkyl, heterocyclic alkyl, aryl, heteroaryl, —C(O)NR$^3$R$^4$, —C(O)R$^3$ and —C(O)OR$^3$, wherein the alkyl, cycloalkyl, heterocyclic alkyl, aryl or heteroaryl is optionally further substituted with one or more groups selected from the group consisting of alkyl, aryl, hydroxyl, amino, alkoxyl, aryloxyl and heterocyclic alkyl;

$R^2$ is selected from the group consisting of hydrogen and alkyl, wherein the alkyl is further substituted with one or more groups selected from the group consisting of cycloalkyl and aryl;

$R^3$ and $R^4$ are each independently selected from the group consisting of hydrogen, alkyl, cycloalkyl, aryl, heteroaryl and heterocyclic alkyl, wherein the alkyl, cycloalkyl, aryl, heteroaryl or heterocyclic alkyl is further optionally substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclic alkyl, heterocyclic alkoxyl, trifluoromethyl, carboxylic acid and carboxylic ester; and $R^3$ and $R^4$ are optionally attached together with the N atom to form a 3- to 8-membered heterocyclic ring, wherein the 5- to 8-membered heterocyclic ring further optionally contains one or more heteroatoms selected from N, O and S, and the 3- to 8-membered ring is further optionally substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclic alkyl, carboxylic acid, carboxylic ester, halogen and —NR$^3$R$^4$.

Preferably, in the compounds of formula (I) or pharmaceutically acceptable salts thereof, R is the following formula.

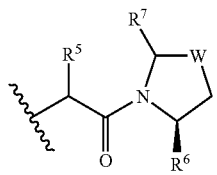

Wherein:

$R^5$ is selected from the group consisting of hydrogen, alkyl, cycloalkyl, aryl, heteroaryl and heterocyclic alkyl, wherein the alkyl, cycloalkyl, aryl, heteroaryl or heterocyclic alkyl is further optionally substituted with one or more groups selected from the group consisting of alkyl, cycloalkyl, aryl, heteroaryl, alkoxyl, cycloalkoxyl, aryloxyl, heteroaryloxyl, halogen, hydroxyl, amino alkylamino, cyano, hydroxyalkyl, heterocyclic alkyl, heterocyclic alkoxyl, carboxylic acid and carboxylic ester; and $R^6$ and $R^7$ are each independently selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclic alkyl, carboxylic acid, carboxylic ester and halogen; and W is C, S or O, wherein C is further optionally substituted with $R^6$ or $R^7$.

Further, the present disclosure includes the compounds of formula (IB) or pharmaceutically acceptable salts thereof.

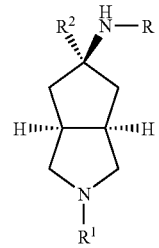

(IB)

Wherein:

R is the following formula:

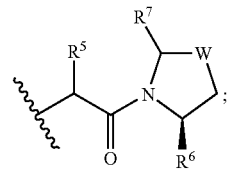

$R^1$ is selected from the group consisting of hydrogen, alkyl, cycloalkyl, heterocyclic alkyl, aryl, heteroaryl, —C(O)NR$^3$R$^4$, —C(O)R$^3$ and —C(O)OR$^3$, wherein the alkyl, cycloalkyl, heterocyclic alkyl, aryl or heteroaryl is further substituted with one or more groups selected from the group consisting of alkyl, aryl, hydroxyl, amino, alkoxyl, aryloxyl and heterocyclic alkyl;

$R^2$ is selected from the group consisting of hydrogen and alkyl, wherein the alkyl is further substituted with one or more groups selected from the group consisting of cycloalkyl and aryl;

$R^3$ and $R^4$ are each independently selected from the group consisting of hydrogen, alkyl, cycloalkyl, aryl, heteroaryl and heterocyclic alkyl, wherein the alkyl, cycloalkyl, aryl, heteroaryl or heterocyclic alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclic alkyl, heterocyclic alkoxyl, trifluoromethyl, carboxylic acid and carboxylic ester;

$R^3$ and $R^4$ are attached together with the N atom to form a 3- to 8-membered heterocyclic ring, wherein the 5- to 8-membered heterocyclic ring further contains one or more heteroatoms selected from N, O and S, and the 3- to 8-membered ring is further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclic alkyl, carboxylic acid, carboxylic ester, halogen, and —NR$^3$R$^4$;

$R^5$ is selected from the group consisting of hydrogen, alkyl, cycloalkyl, aryl, heteroaryl and heterocyclic alkyl, wherein the alkyl, cycloalkyl, aryl, heteroaryl or heterocyclic alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclic alkyl, heterocyclic alkoxyl, carboxylic acid and carboxylic ester; and R[6] and R[7] are each independently selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclic alkyl, carboxylic acid, carboxylic ester and halogen; and W is C, S or O, wherein C can be further substituted with R[6] or R[7].

Further, the present disclosure includes the compounds of formula (IC) or pharmaceutically acceptable salts thereof.

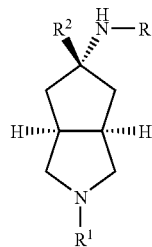
(IC)

Wherein: R is the following formula:

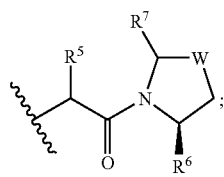

R[1] is selected from the group consisting of hydrogen, alkyl, cycloalkyl, heterocyclic alkyl, aryl, heteroaryl, —C(O)NR[3]R[4], —C(O)R[3] and —C(O)OR[3], wherein the alkyl, cycloalkyl, heterocyclic alkyl, aryl or heteroaryl is further substituted with one or more groups selected from the group consisting of alkyl, aryl, hydroxyl, amino, alkoxyl, aryloxyl and heterocyclic alkyl;

R[2] is selected from the group consisting of hydrogen and alkyl, wherein the alkyl is further substituted with one or more groups selected from the group consisting of cycloalkyl and aryl;

R[3] and R[4] are each independently selected from the group consisting of hydrogen, alkyl, cycloalkyl, aryl, heteroaryl and heterocyclic alkyl, wherein the alkyl, cycloalkyl, aryl, heteroaryl or heterocyclic alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclic alkyl, heterocyclic alkoxyl, trifluoromethyl, carboxylic acid and carboxylic ester;

R[3] and R[4] are attached together with the N atom to form a 3- to 8-membered heterocyclic ring, wherein the 5- to 8-membered heterocyclic ring further contains one or more heteroatoms selected from N, O and S, and the 3- to 8-membered ring is further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclic alkyl, carboxylic acid, carboxylic ester, halogen and —NR[3]R[4];

R[5] is selected from the group consisting of hydrogen, alkyl, cycloalkyl, aryl, heteroaryl and heterocyclic alkyl, wherein the alkyl, cycloalkyl, aryl, heteroaryl or heterocyclic alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclic alkyl, heterocyclic alkoxyl, carboxylic acid and carboxylic ester; and R[6] and R[7] are each independently selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclic alkyl, carboxylic acid, carboxylic ester and halogen; and W is C, S or O, wherein C can be further substituted with R[6] or R[7].

This disclosure provides compounds of formula (I) or pharmaceutically acceptable salts, wherein the salts are obtained by reaction of the compounds of formula (I) with the acids selected from the group consisting of hydrochloric acid, p-toluenesulfonic acid, tartaric acid, maleic acid, lactic acid, methanesulfonic acid, sulfuric acid, phosphoric acid, citric acid, acetic acid and trifluoroacetic acid. Preferred acids are p-toluenesulfonic acid, hydrochloric acid, tartaric acid, and trifluoroacetic acid.

In a particularly preferred embodiment, the compounds of formula (I) or pharmaceutically acceptable salts include:

| Example No. | Structure | Name |
|---|---|---|
| 1 | 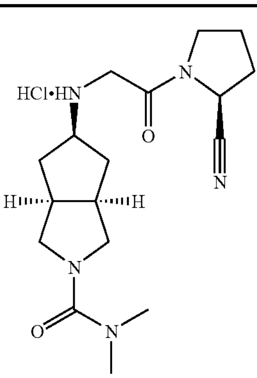 | cis-5-[2-((S)-2-Cyano-pyrrolidin-1-yl)-2-oxo-ethylamino]-hexahydro-cyclopenta[c]pyrrole-2-carboxylic acid dimethylamide hydrochloride |

1

-continued

| Example No. | Structure | Name |
|---|---|---|
| 2 | 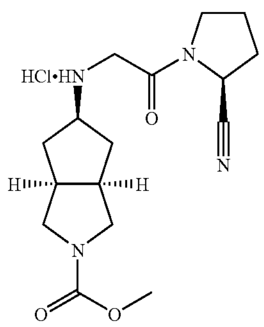 | cis-5-[2-((S)-2-Cyano-pyrrolidin-1-yl)-2-oxoethylamino]-hexahydro-cyclopenta[c]pyrrole-2-carboxylic acid methyl ester hydrochloride |
| 3 | 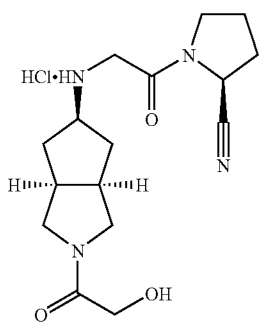 | cis-(S)-1-{2-[2-(2-Hydroxy-acetyl)-octahydro-cyclopenta[c]pyrrol-5-ylamino]-acetyl}-pyrrolidine-2-carbonitrile hydrochloride |
| 4 | 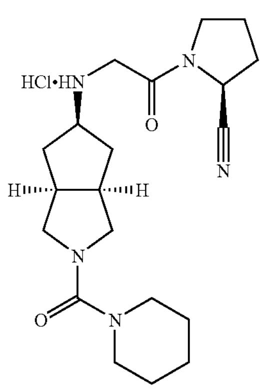 | cis-(S)-1-{2-[2-(Piperidine-1-carbonyl)-octahydro-cyclopenta[c]pyrrol-5-ylamino]-acetyl}-pyrrolidine-2-carbonitrile hydrochloride |
| 5 | 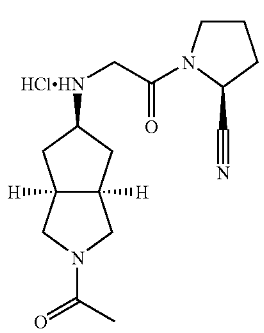 | cis-(S)-1-[2-(2-Acetyl-octahydro-cyclopenta[c]pyrrol-5-ylamino)-acetyl]-pyrrolidine-2-carbonitrile hydrochloride |

-continued

| Example No. | Structure | Name |
|---|---|---|
| 6 | 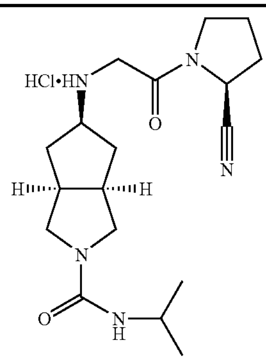 | cis-5-[2-((S)-2-Cyano-pyrrolidin-1-yl)-2-oxo-ethylamino]-hexahydro-cyclopenta[c]pyrrole-2-carboxylic acid isopropylamide hydrochloride |
| 7 | 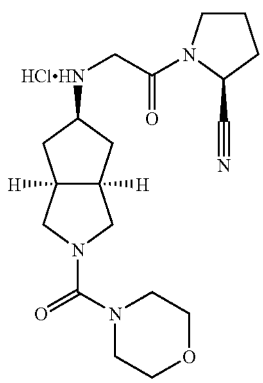 | cis-(S)-1-{2-[2-(Morpholine-4-carbonyl)-octahydro-cyclopenta[c]pyrrol-5-ylamino]-acetyl}-pyrrolidine-2-carbonitrile hydrochloride |
| 8 | 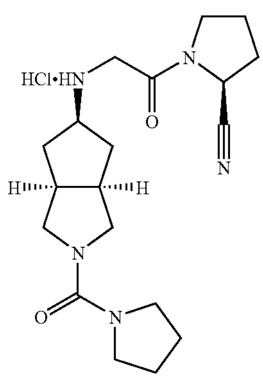 | cis-(S)-1-{2-[2-(Pyrrolidine-1-carbonyl)-octahydro-cyclopenta[c]pyrrol-5-ylamino]-acetyl}-pyrrolidine-2-carbonitrile hydrochloride |
| 9 | 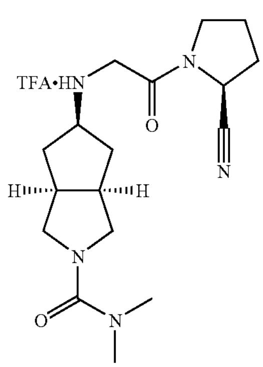 | cis-5-[2-((S)-2-Cyano-pyrrolidin-1-yl)-2-oxo-ethylamino]-hexahydro-cyclopenta[c]pyrrole-2-carboxylic acid dimethylamide trifluoroacetate |

-continued

| Example No. | Structure | Name |
|---|---|---|
| 10 | 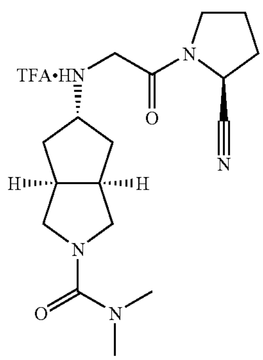 | trans-5-[2-((S)-2-Cyano-pyrrolidin-1-yl)-2-oxo-ethylamino]-hexahydro-cyclopenta[c]pyrrole-2-carboxylic acid dimethylamide trifluoroacetate |
| 11 | 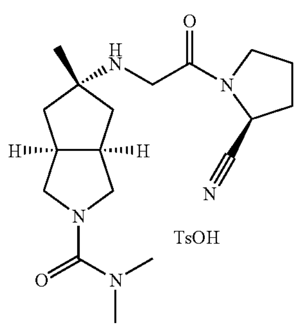 | 5-[2-((S)-2-Cyano-pyrrolidin-1-yl)-2-oxo-ethylamino]-5-methyl-hexahydro-cyclopenta[c]pyrrole-2-carboxylic acid dimethylamide p-toluenesulfonate |
| 12 | 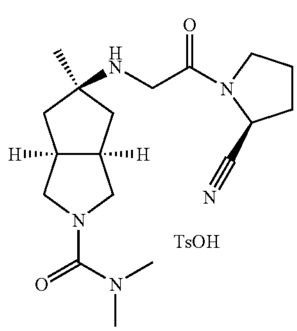 | 5-[2-((S)-2-Cyano-pyrrolidin-1-yl)-2-oxo-ethylamino]-5-methyl-hexahydro-cyclopenta[c]pyrrole-2-carboxylic acid dimethylamide p-toluenesulfonate |
| 13 | 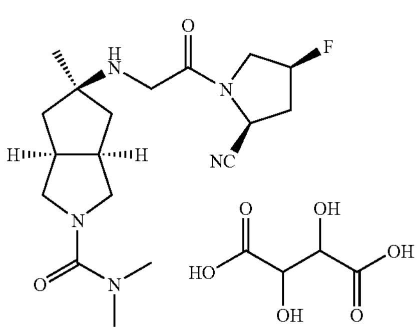 | 5-[2-((2S,4S)-2-Cyano-4-fluoro-pyrrolidin-1-yl)-2-oxo-ethylamino]-N,N,5-trimethyl-hexahydrocyclopenta[c]pyrrole-2-carboxamide tartrate |

-continued

| Example No. | Structure | Name |
|---|---|---|
| 14 | 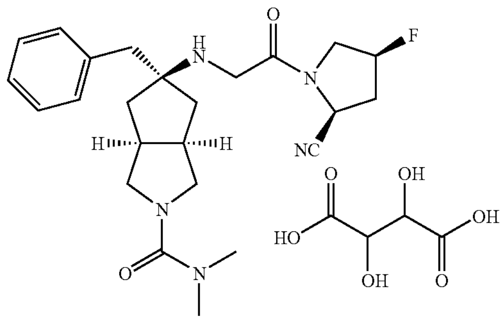 | 5-Benzyl-5-[2-((2S,4S)-2-cyano-4-fluoropyrrolidin-1-yl)-2-oxo-ethylamino]-hexahydrocyclopenta[c]pyrrole-2-carboxylic acid dimethylamide tartrate |
| 15 | 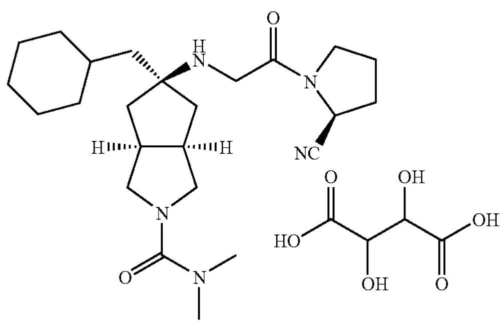 | 5-Cyclohexylmethyl-5-[2-((S)-2-cyano-pyrrolidin-1-yl)-2-oxo-ethylamino]-hexahydrocyclopenta[c]pyrrole-2-carboxylic acid dimethylamide tartrate |
| 16 | 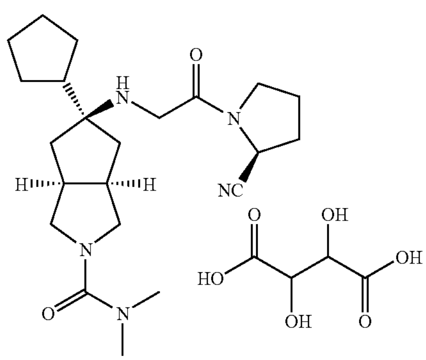 | 5-Cyclopentyl-5-[2-((S)-2-cyano-pyrrolidin-1-yl)-2-oxo-ethylamino]-hexahydrocyclopenta[c]pyrrole-2-carboxylic acid dimethylamide tartrate |
| 17 | 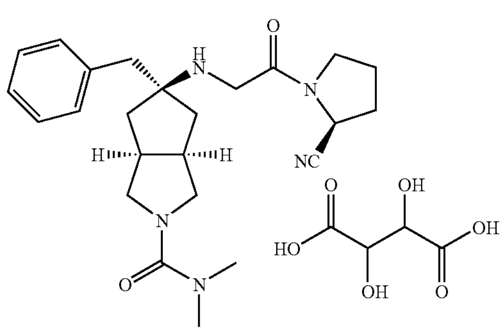 | 5-Benzyl-5-[2-((S)-2-cyano-pyrrolidin-1-yl)-2-oxo-ethylamino]-hexahydrocyclopenta[c]pyrrole-2-carboxylic acid dimethylamide tartrate |

-continued

| Example No. | Structure | Name |
|---|---|---|
| 18 | 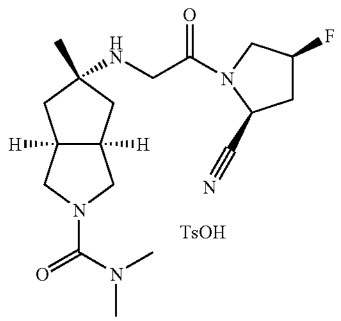 | 5-[2-((2S,4S)-2-Cyano-4-fluoro-pyrrolidin-1-yl)-2-oxo-ethylamino]-5-methyl-hexahydrocyclopenta[c]pyrrole-2-carboxylic acid dimethylamide p-toluenesulfonate |
| 19 | 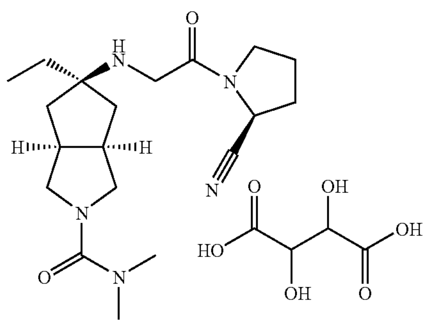 | 5-Ethyl-5-[2-((S)-2-cyano-pyrrolidin-1-yl)-2-oxo-ethylamino]-hexahydrocyclopenta[c]pyrrole-2-carboxylic acid dimethylamide tartrate |

Further, this disclosure relates to the compounds of formula (ID) as intermediates in the synthesis of compounds of formula (I).

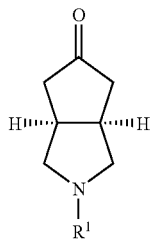

(ID)

Wherein:

$R^1$ is selected from the group consisting of hydrogen, alkyl, cycloalkyl, heterocyclic alkyl, aryl, heteroaryl, —C(O)NR$^3$R$^4$, —C(O)R$^3$ and —C(O)OR$^3$, wherein the alkyl, cycloalkyl, heterocyclic alkyl, aryl or heteroaryl is further substituted with one or more groups selected from the group consisting of alkyl, aryl, hydroxyl, amino, alkoxyl, aryloxyl and heterocyclic alkyl;

$R^3$ and $R^4$ are each independently selected from the group consisting of hydrogen, alkyl, cycloalkyl, aryl, heteroaryl and heterocyclic alkyl, wherein the alkyl, cycloalkyl, aryl, heteroaryl or heterocyclic alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclic alkyl, heterocyclic alkoxyl, trifluoromethyl, carboxylic acid and carboxylic ester; and $R^3$ and $R^4$ are attached together with the N atom to form a 3- to 8-membered heterocyclic ring, wherein the 5- to 8-membered heterocyclic ring further contains one or more heteroatoms selected from N, O and S, and the 3- to 8-membered ring is further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclic alkyl, carboxylic acid, carboxylic ester, halogen, and —NR$^3$R$^4$.

Furthermore, this disclosure relates to a process for the preparation of compounds of formula (ID), comprising the following steps of:

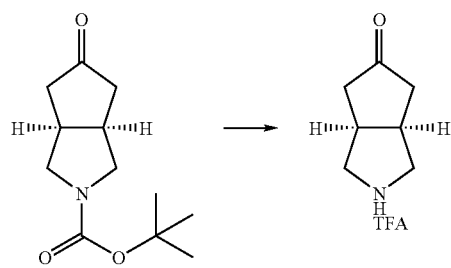

reacting starting material tert-5-oxo-hexahydro-cyclopenta[c]pyrrole-2-carboxylic acid ester with trifluoroacetic acid in a suitable solvent such as dichloromethane, upon cooling by an ice-water bath, to obtain hexahydro-cyclopenta[c]pyrrol-5-one trifluoroacetate; and

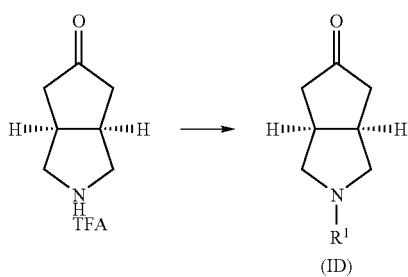

reacting hexahydro-cyclopenta[c]pyrrol-5-one trifluoroacetate with the corresponding acyl chloride or ester in the presence of a base to obtain the compound of formula (ID).

This disclosure relates to the process for the preparation of compounds of formula (IB), comprising the following step:

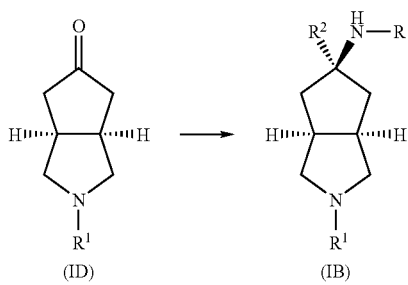

reacting the intermediate of formula (ID), in a suitable solvent such as methanol or ethanol, with an amine, substituted sodium borohydride, and a suitable base such as triethylamine to obtain the compound of formula (IB).

This disclosure relates to the process for the preparation of compounds of formula (IC), comprising the following steps of:

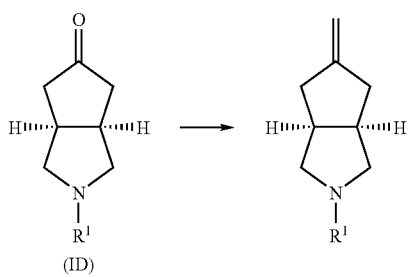

heating potassium tert-butoxide and a solution of methyltriphenylphosphonium iodide in toluene; then adding the intermediate of formula (ID) at room temperature to obtain an azabicyclo alkenyl compound;

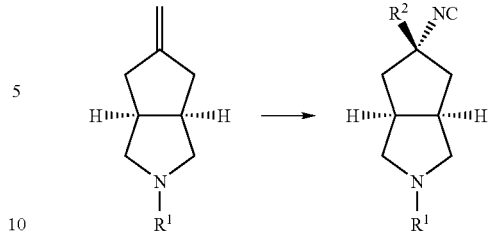

reacting the azabicyclo alkenyl compound, in a suitable solvent such as dichloromethane, with trimethylsilyl cyanide in the presence of silver perchlorate at room temperature to obtain an azabicyclo cyano compound;

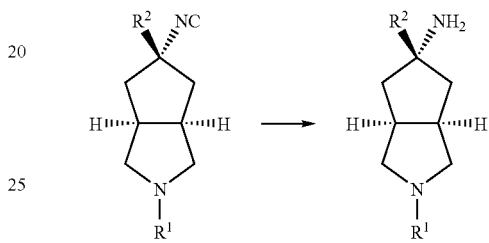

reacting the azabicyclo cyano compound in a suitable solvent such as ethanol with a suitable acid at room temperature to obtain an azabicyclo amine compound; and

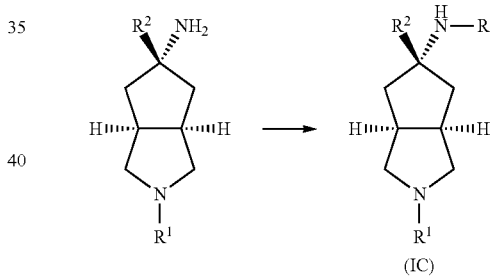

reacting the azabicyclo amine compound with a halo substituted compound in the presence of an alkaline solvent such as N,N-dimethylformamide to obtain compound of formula (IC).

This disclosure relates to the process for the preparation of compounds of formula (IB), comprising the following steps of:

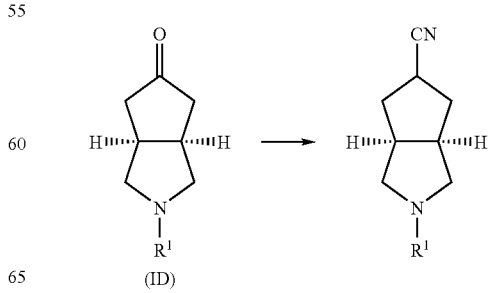

reacting the intermediate of formula (ID) with tosylmethyl isocyanide in a suitable solvent such as ethylene glycol dimethyl ether via an isocyanide reaction to obtain an azabicyclo cyano compound;

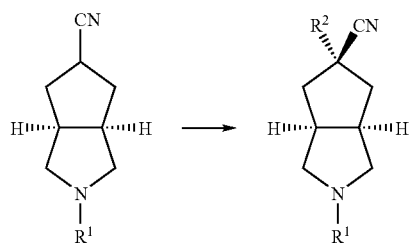

reacting the azabicyclo cyano compound in a suitable solvent such as tetrahydrofuran with a halo compound in the presence of lithium hexamethyldisilazide to obtain a $R^2$ substituted azabicyclo cyano compound;

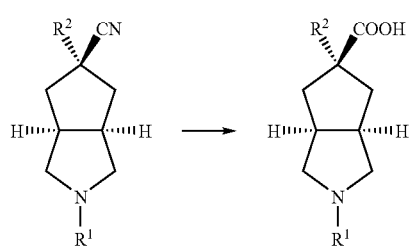

hydrolyzing the $R^2$ substituted azabicyclo cyano compound in the presence of an acid to obtain a $R^2$ substituted azabicyclo carboxyl compound; or reacting the $R^2$ substituted azabicyclo cyano compound with a reductant such as DIBAL-H in a suitable solvent such as dichloromethane upon cooling by an ice-water bath, to obtain an aldehyde compound; reacting the aldehyde compound in a solvent mixture of tetradrofuran/water with sodium dihydrogen phosphate, sodium chlorite and 2-methyl-2-butene, upon cooling by an ice-water bath, to obtain a $R^2$ substituted azabicyclo carboxyl compound;

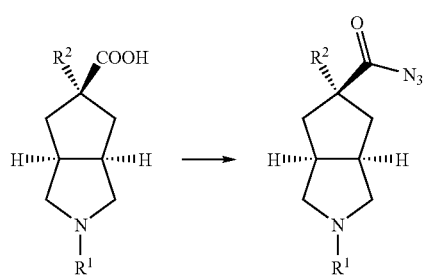

reacting the $R^2$ substituted azabicyclo carboxyl compound with ethyl chloroformate in the presence of a base such as triethylamine via azido reaction to obtain an azabicyclo azido compound;

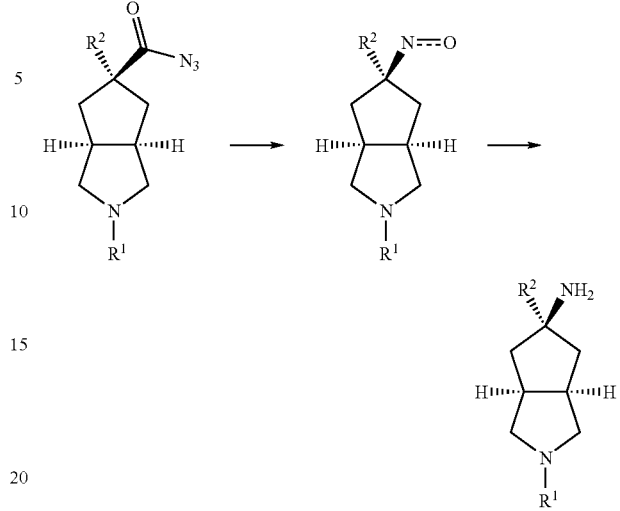

heating the azabicyclo azido compound in a suitable solvent such as toluene followed by stirring in an acidic solution; neutralizing the reaction solution to pH showing alkalescence to obtain a $R^2$ substituted azabicyclo amine compound; and

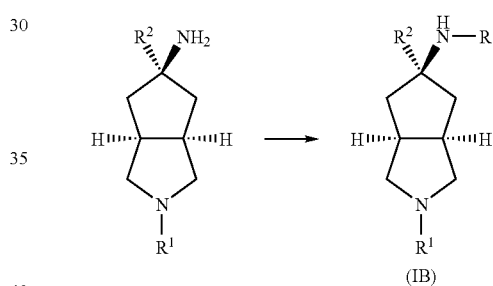

reacting the $R^2$ substituted azabicyclo amine compound with a halo substituted compound in the presence of an alkaline solvent such as N,N-dimethylformamide to obtain the compound of formula (IB).

This disclosure relates to the process for the preparation of compounds of formula (IC), comprising the following steps of:

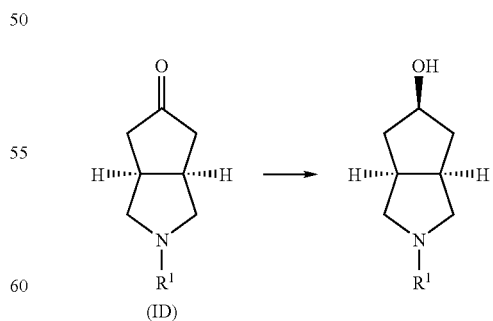

reacting the intermediate of formula (ID) in a suitable solvent such as tetrahydrofuran with a reductant such as lithium tri-tert-butoxyaluminum hydride upon cooling by an ice-water bath to obtain an azabicyclo hydroxyl compound;

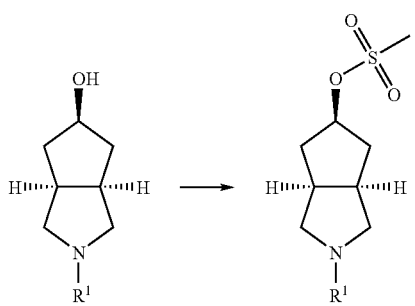

reacting the azabicyclo hydroxyl compound in a suitable solvent such as dichloromethane with an alkaline agent such as triethylamine and methylsulfonyl chloride to obtain an azabicyclo methyl sulfonic acid compound;

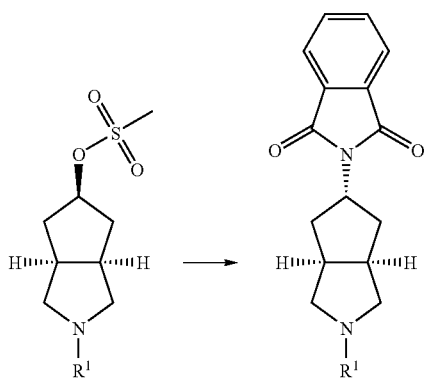

heating the azabicyclo methyl sulfonic acid compound and phthalimide-potassium in the presence of an alkaline agent such as N,N-dimethylformamide to obtain a phthalimide substituted azabicyclo compound;

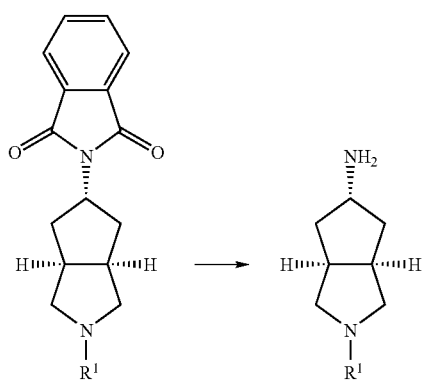

heating the phthalimide substituted azabicyclo compound and hydrazine in a suitable solvent such as ethanol to obtain an azabicyclo amine compound; and

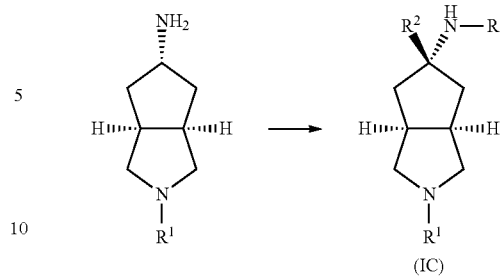

heating the azabicyclo amine compound and a halo compound in a suitable solvent such as dichloromethane to obtain compound of formula (IC).

Preferably, in the preparation processes described above, R is the following formula:

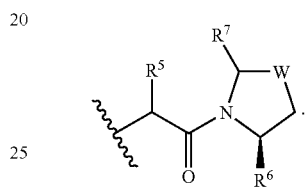

$R^5$ is selected from the group consisting of hydrogen, alkyl, cycloalkyl, aryl, heteroaryl and heterocyclic alkyl, wherein the alkyl, cycloalkyl, aryl, heteroaryl or heterocyclic alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclic alkyl, heterocyclic alkoxyl, carboxylic acid and carboxylic ester.

$R^6$ and $R^7$ are each independently selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclic alkyl, carboxylic acid, carboxylic ester and halogen; and W is C, S or O, wherein C can be further substituted with $R^6$ or $R^7$.

The purified compounds of formula (IB) and formula (IC) are further reacted with acids in the solvent of methanol, dichloromethane or ethyl acetate to obtain the acid addition salts.

Furthermore, this disclosure relates to a pharmaceutical composition comprising the compounds of the present disclosure or salts thereof in an effective therapeutic dose, and a pharmaceutically acceptable carrier.

Furthermore, this disclosure relates to a use of the compounds of the present disclosure or pharmaceutical acceptable salts in the preparation of a medicament as a dipeptidyl peptidase (DPP-IV) inhibitor.

This disclosure also relates to the compounds of formula (I) or pharmaceutically acceptable salts thereof, wherein the compounds of formula (I) may be present in free form or in the form of acid addition salts which are pharmaceutically acceptable non-toxic. The pharmaceutically acceptable salts include hydrochloride, p-toluenesulfonate, tartarate, maleate, lactate, methanesulfonate, sulfate, phosphate, citrate, acetate and trifluoroacetate, preferably p-toluenesulfonate, hydrochloride, tartarate and trifluoroacetate.

DETAILED DESCRIPTION OF THE DISCLOSURE

Unless otherwise stated, the following terms used in the specification and claims have the meanings discussed below.

The term "alkyl" refers to a saturated aliphatic hydrocarbon group including $C_1$-$C_{20}$ straight chain and branched chain groups. Preferably an alkyl group is a moderate size alkyl having 1 to 10 carbon atoms, e.g., methyl, ethyl, propyl, 2-propyl, n-butyl, iso-butyl, tert-butyl, pentyl, and the like. More preferably, it is a lower alkyl having 1 to 4 carbon atoms, e.g., methyl, ethyl, propyl, 2-propyl, n-butyl, iso-butyl, or tert-butyl, and the like. The alkyl group may be substituted or unsubstituted. When substituted, the substituent group(s) is preferably halo, hydroxyl, lower alkoxy, aryl, aryloxy, heteroaryl, heterocyclic alkyl, —C(O)$R^3$ and —C(O)N$R^3R^4$.

The term "cycloalkyl" refers to a 3- to 8-membered all-carbon monocyclic ring, an all-carbon 5-membered/6-membered or 6-membered/6-membered fused bicyclic ring or a multicyclic fused ring (a "fused" ring system means that each ring in the system shares an adjacent pair of carbon atoms with other ring in the system) group wherein one or more rings may contain one or more double bonds, but none of the rings has a completely conjugated pi-electron system. Examples of cycloalkyl groups are cyclopropyl, cyclobutyl, cyclopentyl, cyclopentenyl, chcyclohexyl, cyclohexadienyl, adamantyl, cycloheptyl, cycloheptatrienyl, and the like. The cycloalkyl group may be substituted or unsubstituted. When substituted, the substituent group(s) is preferably one or more independently selected from the group consisting of lower alkyl, trihaloalkyl, halo, hydroxy, lower alkoxy, aryl (optionally substituted with one or more groups which each independently is halo, hydroxy, lower alkyl or lower alkoxy groups), aryloxy (optionally substituted with one or more groups which each independently is halo, hydroxy, lower alkyl or lower alkoxy groups), 6-membered heteroaryl (having 1 to 3 nitrogen atoms on the ring, the carbons on the ring being optionally substituted with one or more groups which each independently is halo, hydroxy, lower alkyl or lower alkoxy groups), 5-membered heteroaryl (having 1 to 3 heteroatoms selected from the group consisting of nitrogen, oxygen and sulfur, the carbon and nitrogen atoms of the group being optionally substituted with one or more groups which each independently is halo, hydroxy, lower alkyl or lower alkoxy groups), 5- or 6-membered heterocyclic alkyl (having 1 to 3 heteroatoms selected from the group consisting of nitrogen, oxygen and sulfur, the carbon and nitrogen (if present) atoms of the group being optionally substituted with one or more groups which each independently is halo, hydroxy, lower alkyl or lower alkoxy groups), mercapto, (lower alkyl) thio, arylthio (optionally substituted with one or more groups which each independently is halo, hydroxy, lower alkyl or lower alkoxy groups), cyano, acyl, thioacyl, O-carbamyl, N-carbamyl, O-thiocarbamyl, N-thiocarbamyl, C-amido, N-amido, nitro, N-sulfonamido, S-sulfonamido, C(O)$R^3$, C(O)N$R^3R^4$ and —C(O)O$R^3$ The term "alkenyl" refers to an alkyl group as defined above having at least 2 carbon atoms and at least one carbon-carbon double bond. Representative examples include, but are not limited to ethenyl, 1-propenyl, 2-propenyl, 1-, 2-, 3-butenyl, and the like.

The term "alkynyl" refers to an alkyl group as defined above having at least 2 carbon atoms and at least one carbon-carbon triple bond. Representative examples include, but are not limited to ethynyl, 1-propynyl, 2-propynyl, 1-, 2-, 3-butynyl, and the like.

The term "aryl" refers to groups having at least one aromatic ring, i.e., having a conjugated pi-electron system, including all-carbon cyclic aryl, heteroaryl and biaryl group. The aryl group may be optionally substituted with one or more groups each independently selected from the group consisting of halo, trihalomethyl, hydroxy, SR, nitro, cyano, alkoxyl and alkyl.

The term "heteroaryl" refers to an aryl having 1 to 3 heteroatoms selected from the group consisting of N, O, and S as ring atoms, the remaining ring atoms being C. The ring is 5- or 6-membered ring. The examples of heteroaryl groups include furyl, thienyl, pyridyl, pyrrolyl, N-alkyl pyrrolyl, pyrimidinyl, pyrazinyl, imidazolyl, and the like.

The term "heterocyclic alkyl" refers to a monocyclic or fused ring group of 5 to 9 ring atoms, wherein one, or two ring heteroatoms are selected from the group consisting of N, O, and S(O)$_n$ (n is integer from 0 to 2), the remaining ring atoms are C, in addition, the ring may also have one or more double bonds, but not have a completely conjugated pi-electron system. The unsubstituted heterocyclic alkyl includes, but is not limited to pyrrolidyl, piperidyl, piperazinyl, morpholinyl, thiomorpholinyl, homopiperazinyl, and the like. The heterocyclic alkyl may be substituted or unsubstituted. When substituted, the substituent group is preferably one or more, more preferably one, two, or three, further more preferably one or two groups, each independently selected from the group consisting of lower alkyl, trihaloalkyl, halo, hydroxy, lower alkoxy, cyano and acyl. Preferably, the heterocyclic alkyl is optionally substituted with one or two groups independently selected from the group consisting of halo, lower alkyl, trihaloalkyl, hydroxy, mercapto, cyano, N-amido, and carboxy.

The term "hydroxy" refers to an —OH group.

The term "alkoxyl" refers to both an —O-(alkyl) and an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

The term "haloalkoxy" refers to an —O-(haloalkyl). Representative examples include, but are not limited to, trifluoromethoxy, tribromomethoxy, and the like.

The term "aryloxyl" refers to both an —O-aryl and an —O-heteroaryl group, wherein the aryl and heteroaryl are as defined above. Representative examples include, but are not limited to, phenoxy, pyridinyloxy, furanyloxy, thienyloxy, pyrimidinyloxy, pyrazinyloxy, and the like, and derivatives thereof.

The term "mercapto" refers to a —SH group.

The term "alkylthio" refers to a —S-(alkyl) and a —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

The term "arylthio" refers to a —S-aryl and a —S-heteroaryl group, wherein the aryl and heteroaryl are as defined above. Representative examples include, but are not limited to, e.g., phenylthio, pyridinylthio, furanylthio, thienylthio, pyrimidinylthio, and the like, and derivatives thereof.

The term "acyl" refers to a —C(O)—R" group, where R" is selected from the group consisting of hydrogen, lower alkyl, trihalomethyl, unsubstituted cycloalkyl, aryl (optionally substituted with one or more, preferably one, two, or three substituents selected from the group consisting of lower alkyl, trihalomethyl, lower alkoxy and halo groups), heteroaryl (bonded through a ring carbon) (optionally substituted with one or more, preferably one, two, or three substituents selected from the group consisting of lower alkyl, trihaloalkyl, lower alkoxy and halo groups), and heteroalicyclic (bonded through a ring carbon) (optionally substituted with one or more, preferably one, two, or three substituents selected from the group consisting of lower alkyl, trihaloalkyl, lower alkoxy and halo groups). Representative acyl groups include, but are not limited to, acetyl, trifluoroacetyl, benzoyl, and the like.

The term "thioacyl" refers to a —C(S)—R" group, wherein R" is as defined above.

The term "acetyl" refers to a —C(O)CH$_3$ group.

The term "halo" refers to fluoro, chloro, bromo, or iodo, preferably fluoro or chloro.

The term "trifluoromethyl" refers to a —CF3 group.

The term "cyano" refers to a —C≡N group.

The term "amino" refers to a —NH$_2$ group.

The term "carboxylic acid" refers to a —COOH group.

The term "carboxylic ester" refers to a —COOR group, wherein R is alkyl or cycloalkyl.

The term "hydroxyl alkyl" refers to a —(CH$_2$)$_r$OH group, wherein r is an integer from 1 to 4.

The term "optional" or "optionally" means that the subsequently described event or circumstance may or may not occur, and that the description includes instances where the event or circumstance may or may not occur. For example, "heterocycle group optionally substituted with an alkyl group" means that the alkyl may or may not be present, and the description includes situations where the heterocyclic group is substituted with an alkyl group and situations where the heterocyclic group is not substituted with the alkyl group.

The term "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

Synthesis Method of the Disclosure Compound

Scheme I

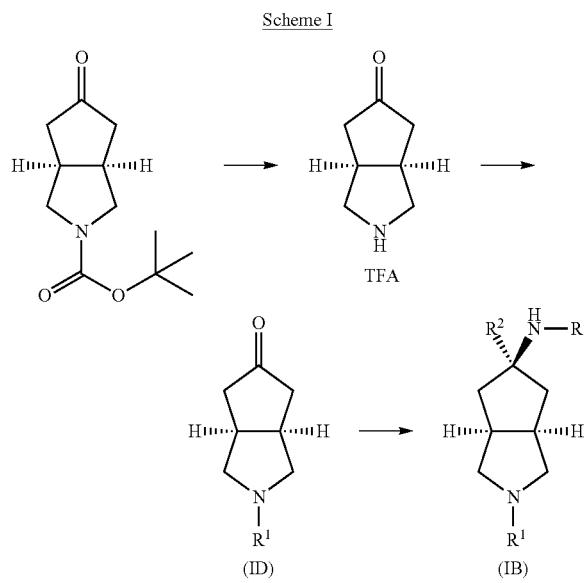

Scheme I includes the steps of: reacting tert-butyl-5-oxo-hexahydro-cyclopenta[c]pyrrole-2-carboxylic acid ester with trifluoroacetic acid in a suitable solvent such as dichloromethane, upon cooling by an ice-water bath, to obtain hexahydro-cyclopenta[c]pyrrol-5-one trifluoroacetate; reacting hexahydro-cyclopenta[c]pyrrol-5-one trifluoroacetate with an acyl chloride or ester in the presence of a base to obtain the compound of formula (ID); and reacting the intermediate of formula (ID), in a suitable solvent such as methanol or ethanol, with corresponding amines, substituted sodium borohydride and a suitable base such as triethylamine to obtain the compound of formula (IB) at room temperature.

Scheme II

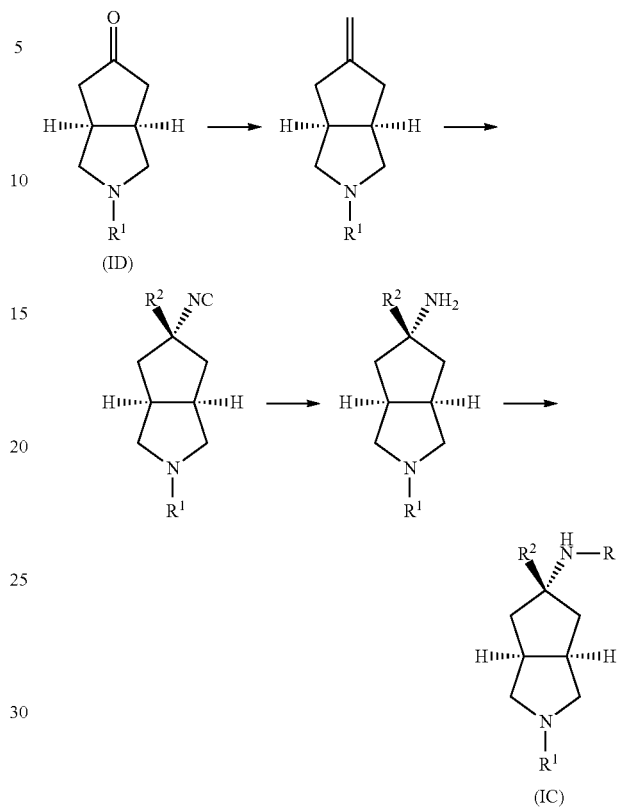

Scheme II includes the steps of: heating potassium tert-butoxide and a solution of methyltriphenylphosphonium iodide in toluene followed by addition of the intermediate of formula (ID) at room temperature to obtain an azabicyclo alkenyl compound; reacting the azabicyclo alkenyl compound, in a suitable solvent such as dichloromethane, with trimethylsilyl cyanide in the presence of silver perchlorate at room temperature to obtain an azabicyclo cyano compound; reacting the azabicyclo cyano compound in a suitable solvent such as ethanol with a suitable acid such as hydrochloric acid at room temperature to obtain an azabicyclo amine compound; and reacting the azabicyclo amine compound with a halo substituted compound in the presence of an alkaline solvent such as N,N-dimethylformamide to obtain compound of formula (IC).

Scheme III

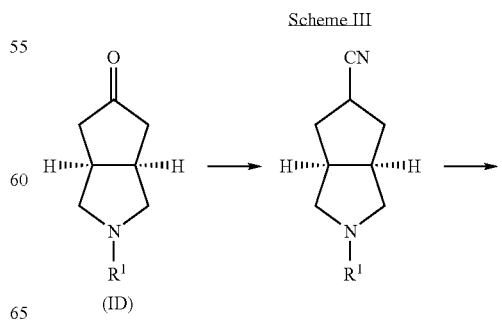

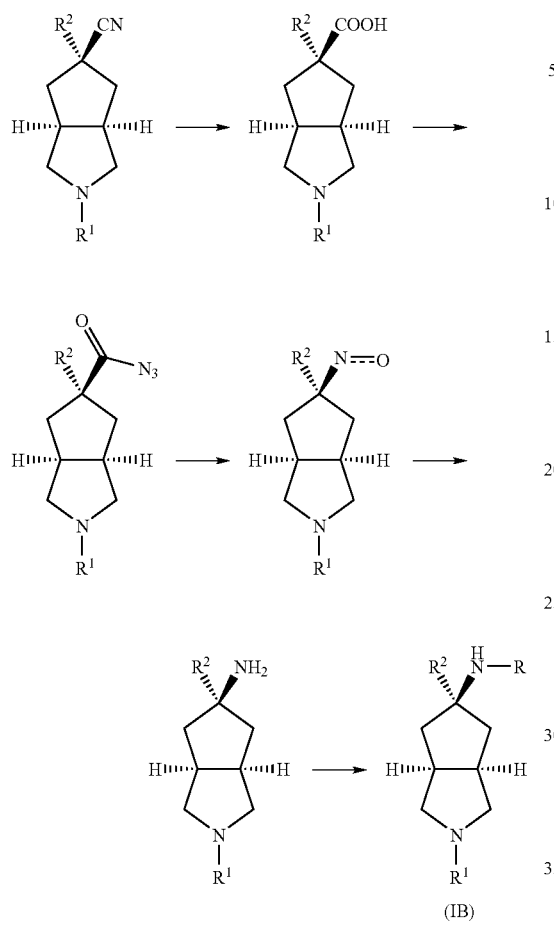

(IB)

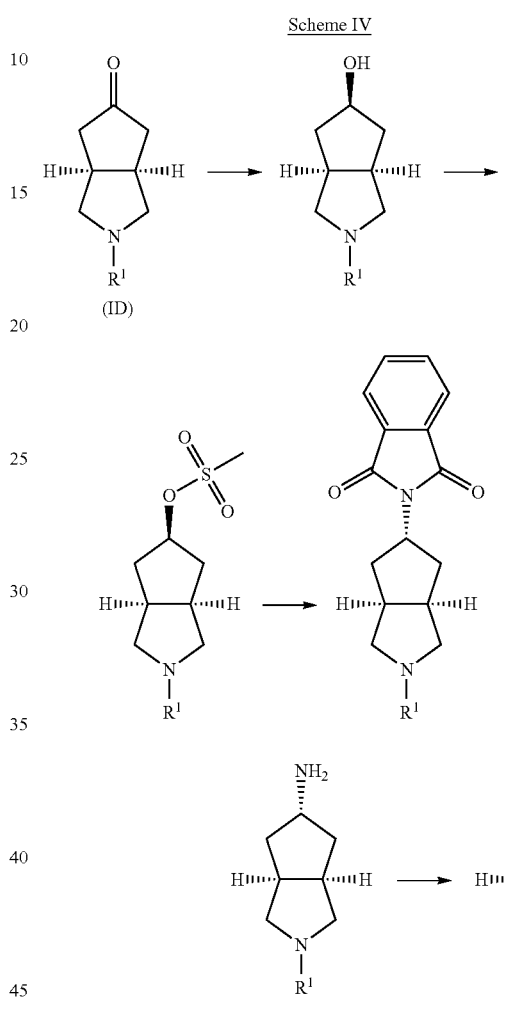

(IC)

Scheme III includes the steps of: reacting the intermediate of formula (ID) with tosylmethyl isocyanide in a suitable solvent such as ethylene glycol dimethyl ether via an isocyanide reaction to obtain an azabicyclo cyano compound; reacting the azabicyclo cyano compound in a suitable solvent such as tetrahydrofuran with a halo compound in the presence of lithium hexamethyldisilazide to obtain a $R^2$ substituted azabicyclo cyano compound; hydrolyzing the $R^2$ substituted azabicyclo cyano compound in the presence of an acid to obtain a $R^2$ substituted azabicyclo carboxyl compound or reacting the $R^2$ substituted azabicyclo cyano compound with a reductant such as DIBAL-H in a suitable solvent such as dichloromethane upon cooling by an ice-water bath, to obtain an aldehyde compound; reacting the aldehyde compound in a solvent mixture of tetradrofuran/water with sodium dihydrogen phosphate, sodium chlorite and 2-methyl-2-butene, upon cooling by an ice-water bath, to obtain a $R^2$ substituted azabicyclo carboxyl compound; reacting the $R^2$ substituted azabicyclo carboxyl compound with ethyl chloroformate in the presence of a base such as triethylamine via azido reaction to obtain an azabicyclo azido compound; heating the azabicyclo azido compound in a suitable solvent such as toluene followed by stirring in an acidic solution; neutralizing the reaction solution to pH showing alkalescence to obtain a $R^2$ substituted azabicyclo amine compound; and reacting the $R^2$ substituted azabicyclo amine compound with a halo substituted compound in the presence of an alkaline solvent such as N,N-dimethylformamide to obtain the compound of formula (IB).

Scheme IV

Scheme IV includes the steps of: reacting the intermediate of formula (ID) in a suitable solvent such as tetrahydrofuran with a reductant such as lithium tri-tert-butoxyaluminum hydride upon cooling by an ice-water bath to obtain an azabicyclo hydroxyl compound; reacting the azabicyclo hydroxyl compound in a suitable solvent such as dichloromethane with an alkaline agent such as triethylamine and methylsulfonyl chloride to obtain an azabicyclo methyl sulfonic acid compound; heating the azabicyclo methyl sulfonic acid compound and phthalimide-potassium in the presence of an alkaline agent such as N,N-dimethylformamide to obtain a phthalimide substituted azabicyclo compound; heating the phthalimide substituted azabicyclo compound and hydrazine in a suitable solvent such as ethanol to obtain an azabicyclo amine compound; and heating the azabicyclo amine compound and a halo compound in a suitable solvent such as dichloromethane to obtain compound of formula (IC).

The purified compounds of formula (IB) and formula (IC) are further reacted with acids in the solvent of methanol, dichloromethane or ethyl acetate to obtain the acid addition salts.

Furthermore, this disclosure relates to a pharmaceutical composition comprising the compounds of the present disclosure or salts thereof in an effective therapeutic dose, and a pharmaceutically acceptable carrier; and a use of the compounds of the present disclosure or pharmaceutical acceptable salts in the preparation of a medicament as a dipeptidyl peptidase (DPP-IV) inhibitor. In other words, this disclosure also provides a pharmaceutical composition comprising the above mentioned compounds in an effective therapeutic dose, as well as their use in the preparation of a medicament as a dipeptidyl peptidase (DPP-IV) inhibitor.

Specific Implementation Methods

The following examples serve to illustrate the disclosure, but the examples should not be considered as limiting the scope of the disclosure.

EXAMPLES

The structures of all compounds were identified by nuclear magnetic resonance ($^1$H NMR) and mass spectrometry (MS). $^1$H NMR chemical shifts (δ) were recorded in ppm ($10^{-6}$). NMR was performed on a Bruker AVANCE-400 spectrometer. The suitable solvents were deuterated-chloroform ($CDCl_3$), deuterated-dimethyl sulfoxide (DMSO-$d_6$) and deuterated-methanol ($CD_3OD$) with tetramethylsilane (TMS) as an internal standard and chemical shifts were recorded in ppm ($10^{-6}$).

MS was determined by a FINNIGA N LCQ Ad (ESI) mass spectrometer.

The average of inhibitory rate of kinase and $IC_{50}$ was determined by a NovoStar ELIASA (BMG Co. German)

Thin-layer silica gel was Yantai Huanghai HSGF254 or Qingdao GF254 silica gel plate.

Column chromatography studies generally used Yantai Huanghai 200-300 mesh silica gel as a carrier.

DMSO-$D_6$: deuterated-dimethyl sulfoxide.
$CDCl_3$: deuterated-chloroform.
$CD_3OD$: deuterated-methanol Example 1 cis-5-[2-((S)-2-Cyano-pyrrolidin-1-yl)-2-oxo-ethylamino]-N,N-dimethyl-hexahydro-cyclopenta[c]pyrrole-2-carboxamide hydrochloride

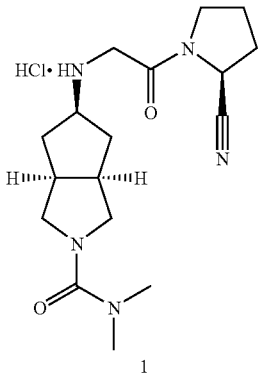

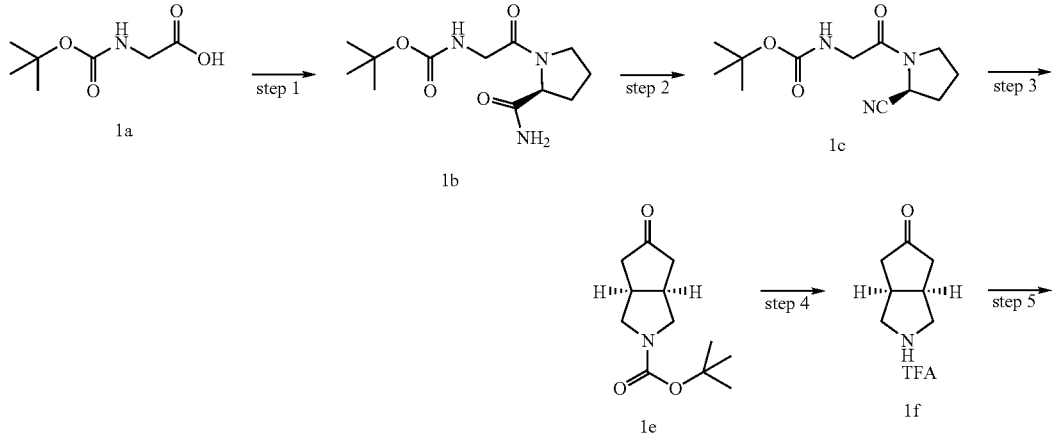

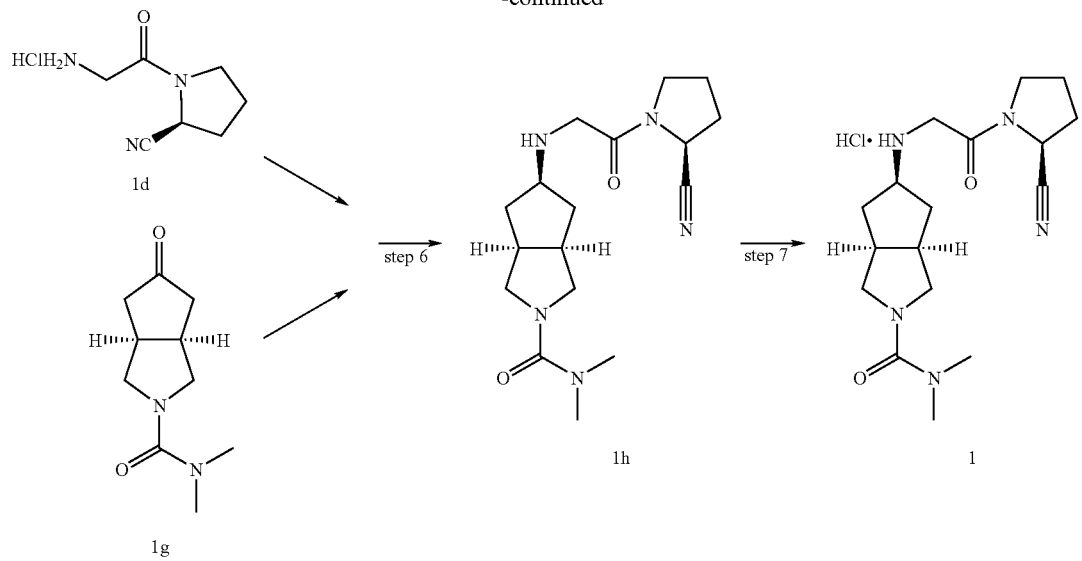

Step 1

Preparation of (S)-[2-(2-carbamoyl-pyrrolidin-1-yl)-2-oxo-ethyl]-carbamic acid tent-butyl ester 1b N-tert-butyloxycarbonyl glycine 1a (5 g, 28.56 mmol) and L-prolinamide (3.25 g, 28.50 mmol) were dissolved in 75 mL of N,N-dimethylformamide and the mixture was cooled to 0° C. Then 1-hydroxybenzotriazole (11.8 g, 87.3 mmol), N-ethyl-N'-(dimethylaminopropyl)-carbodiimide (11.3 g, 59 mmol) and triethylamine (12.1 mL, 87.3 mmol) were added with stirring. The reaction mixture was warmed up to room temperature and stirred overnight. The reaction was monitored by thin layer chromatography (TLC) until the disappearance of the starting materials. N,N-dimethylformamide was evaporated below 50° C. The resulting mixture was extracted with ethyl acetate (200 mL×3). The combined organic extracts were washed with 50 mL of saturated brine, dried over anhydrous sodium sulfate, filtered and concentrated under reduced pressure. The residue was recrystallized from ethyl acetate to obtain the title compound (S)-[2-(2-carbamoyl-pyrrolidin-1-yl)-2-oxo-ethyl]-carbamic acid tert-butyl ester 1b (7.42 g, yield 95.8%) as a white powder.

MS m/z (ESI): 272.1 [M+1]

Step 2

Preparation of (S)-[2-(2-cyano-pyrrolidin-1-yl)-2-oxo-ethyl]-carbamic acid tert-butyl ester 1c In a dry three-necked flask, 286 mL of pyridine, (S)-[2-(2-carbamoyl-pyrrolidin-1-yl)-2-oxo-ethyl]-carbamic acid tert-butyl ester 1b (13.5 g, 49.8 mmol) and imidazole (7.11 g, 104.6 mmol) were added successively under nitrogen atmosphere. Then the reaction system was cooled to −35° C. followed by dropwise addition of phosphorus oxychloride (19 mL, 204.2 mmol) with stirring. The reaction mixture was stirred for 1 hour at the same temperature. After warmed up to room temperature, the reaction mixture was stirred for another 30 minutes. The mixture was evaporated to remove pyridine and the resulting mixture was diluted with ethyl acetate followed by addition of water. The mixture was extracted with ethyl acetate (200 mL×3). The combined organic extracts were washed with 50 mL of saturated brine, dried over anhydrous sodium sulfate, filtered and concentrated under reduced pressure. The resulting residue was purified by silica gel column chromatography to obtain the title compound (S)-[2-(2-cyano-pyrrolidin-1-yl)-2-oxo-ethyl]-carbamic acid tert-butyl ester 1c (10.7 g, yield 84.9%) as a white powder.

MS m/z (ESI): 254.3 [M+1]

Step 3

Preparation of (S)-1-(2-amino-acetyl)-pyrrolidine-2-carbonitrile hydrochloride 1d (S)-[2-(2-Cyano-pyrrolidin-1-yl)-2-oxo-ethyl]-carbamic acid tert-butyl ester 1c (13.7 g, 54.2 mmol) was dissolved in 140 mL of ether and 40 mL of water with stirring. Upon cooling by an ice-water bath, 37% hydrochloric acid (90 mL) was dropwise added and the reaction mixture was stirred for 1 hour at the same temperature. The mixture was concentrated under reduced pressure and the residue diluted with ether was filtered with a filtering centrifuge to obtain the title compound (S)-1-(2-amino-acetyl)-pyrrolidine-2-carbonitrile hydrochloride 1d (10 g, yield 98%) as a white powder.

MS m/z (ESI): 154.4 [M+1]

Step 4

Preparation of hexahydro-cyclopenta[c]pyrrol-5-one trifluoroacetate 1f tert-Butyl 5-oxo-hexahydro-cyclopenta[c]pyrrole-2-carboxylate 1e (0.32 g, 1.42 mmol) was dissolved in 10 mL of dichloromethane with stirring. Upon cooling by an ice-water bath, trifluoroacetic acid (3.27 mL, 42.7 mmol) was added and the reaction mixture was reacted for 30 minutes at 0° C. The mixture was concentrated under reduced pressure to obtain the crude title compound hexahydro-cyclopenta[c]pyrrol-5-one trifluoroacetate 1f, which was directly used in the next step.

MS m/z (ESI): 126.4 [M+1]

Step 5

Preparation of N,N-dimethyl-5-oxo-hexahydro-cyclopenta[c]pyrrole-2-carboxamide 1g Hexahydro-cyclopenta[c]pyrrol-5-one trifluoroacetate 1f obtained from the above step was dissolved in 15 mL of acetonitrile with stirring. Upon cooling by an ice-water bath, potassium carbonate (0.24 g, 1.71 mmol) was added followed by dimethylcarbamic chloride (0.14 mL, 1.56 mmol). The reaction mixture was warmed up to room temperature and reacted for 2 hours. The mixture was concentrated under reduced pressure and diluted with 50 mL of water. The mixture was extracted with ethyl acetate (50 mL×3). The combined organic extracts were washed with 50 mL of saturated brine, dried over anhydrous magnesium sulfate, filtered and concentrated under reduced pressure. The resulting residue was purified by silica gel column chromatography to obtain the title compound N,N-dimethyl-5-oxo-hexahydro-cyclopenta[c]pyrrole-2-carboxamide 1g (0.19 g, yield 68.3%) as a light yellow oil.

MS m/z (ESI): 197.4 [M+1]

$^1$H NMR (DMSO-D$_6$, 400 MHz): δ 3.56 (m, 2H), 2.85 (m, 2H), 2.7 (s, 6H), 2.81 (m, 2H), 2.5 (m, 2H), 2.01 (m, 2H).

Step 6

Preparation of cis-5-[2-((S)-2-cyano-pyrrolidin-1-yl)-2-oxo-ethylamino]-N,N-dimethyl hexahydro-cyclopenta[c]pyrrole-2-carboxamide 1 h (S)-1-(2-Amino-acetyl)-pyrrolidine-2-carbonitrile hydrochloride 1d (0.36 g, 1.91 mmol) was dissolved in 20 mL of methanol with stirring, followed by addition of N,N-dimethyl-5-oxo-hexahydro-cyclopenta[c]pyrrole-2-carboxamide 1g (0.25 g, 1.28 mmol) and sodium triacetoxyborohydride (1.22 g, 5.74 mmol). The reaction mixture was reacted for 3 hours at room temperature. The mixture was concentrated and diluted with 20 mL of saturated aqueous sodium carbonate. Then the mixture was extracted with dichloromethane (20 mL×10). The combined organic extracts were washed with 10 mL of saturated brine, dried over anhydrous sodium sulfate, filtered and concentrated under reduced pressure. The resulting residue was purified by silica gel column chromatography to obtain the title compound cis-5-[2-((S)-2-cyano-pyrrolidin-1-yl)-2-oxo-ethylamino]-N,N-dimethyl hexahydro-cyclopenta[c]pyrrole-2-carboxamide 1 h (0.3 mg, yield 53%) as a white powder.

MS m/z (ESI): 334.5 [M+1]

Step 7 cis-5-[2-((S)-2-Cyano-pyrrolidin-1-yl)-2-oxo-ethylamino]-N,N-dimethyl-hexahydro-cyclopenta[c]pyrrole-2-carboxamide hydrochloride cis-5-[2-((S)-2-Cyano-pyrrolidin-1-yl)-2-oxo-ethylamino]-N,N-dimethyl hexahydro-cyclopenta[c]pyrrole-2-carboxamide 1 h (200 mg, 0.687 mmol) was dissolved in 10 mL of dichloromethane. Upon cooling by an ice-water bath, 2 mL of hydrochloric acid in ether (0.5 N) was added. The mixture was concentrated under reduced pressure and diluted with 10 mL of ether. The resulting mixture was filtered with a filtering centrifuge to obtain the title compound cis-5-[2-(S)-2-cyano-pyrrolidin-1-yl)-2-oxo-ethylamino]-N,N-dimethyl-hexahydro-cyclopenta[c]pyrrole-2-carboxamide hydrochloride 1 (180 mg, 80%) as a white power. $^1$H NMR (CD$_3$OD, 400 MHz): δ 4.82 (dd, 1H, J$_1$=4 Hz, J$_2$=5.2 Hz), 4.02 (dd, 2H, J$_1$=J$_2$=16.4 Hz), 3.62-3.25 (m, 7H), 2.76 (s, 6H), 2.51-1.49 (m, 10H).

Example 2 cis-Methyl-5-[2-((S)-2-cyano-pyrrolidin-1-yl)-2-oxo-ethylamino]-hexahydro-cyclopenta[c]pyrrole-2-carboxamide hydrochloride

Step 1

Preparation of methyl 5-oxo-hexahydro-cyclopenta[c]pyrrole-2-carboxamide 2a

Hexahydro-cyclopenta[c]pyrrol-5-one trifluoroacetate 1f (0.559 g, 2.34 mmol) was dissolved in 20 mL of acetonitrile. Upon cooling by an ice-water bath, potassium carbonate (0.646 g, 4.68 mmol) and methyl 2-chloroacetate (0.22 mL, 2.8 mmol) added successively. The reaction mixture was warmed up to room temperature and stirred overnight. The mixture was concentrated under reduced pressure and diluted with 50 mL of water. The mixture was extracted with ethyl acetate (50 mL×3). The combined organic extracts were washed with 50 mL of saturated brine and 50 mL of water successively, dried over anhydrous magnesium sulfate, filtered and concentrated under reduced pressure. The resulting residue was purified by silica gel column chromatography to obtain the title compound methyl 5-oxo-hexahydro-cyclopenta[c]pyrrole-2-carboxamide 2a (0.25 g, yield 58.4%) as a colorless oil.

MS m/z (ESI): 184 [M+1]

Step 2

Preparation of cis-Methyl-5-[2-((S)-2-cyano-pyrrolidin-1-yl)-2-oxo-ethylamino]-hexahydro-cyclopenta[c]pyrrole-2-carboxamide 2b (S)-1-(2-Amino-acetyl)-pyrrolidine-2-carbonitrile hydrochloride 1d (0.43 g, 2.29 mmol) was dissolved in 20 mL of methanol with stirring followed by addition of methyl 5-oxo-hexahydro-cyclopenta[c]pyrrole-2-carboxamide 2a (0.28 g, 1.53 mmol) and sodium triacetoxyborohydride (1.46 g, 6.88 mmol). The reaction mixture was reacted for 3 hours at room temperature. The mixture was concentrated and diluted with 20 mL of saturated aqueous sodium carbonate. The mixture was extracted with dichloromethane (20 mL×3). The combined organic extracts were washed with 10 mL of saturated brine, dried over anhydrous sodium sulfate, filtered and concentrated under reduced pressure. The resulting residue was purified by silica gel column chromatography to obtain the title compound cis-methyl-5-[2-((S)-2-cyano-pyrrolidin-1-yl)-2-oxo-ethylamino]-hexahydro-cyclopenta[c]pyrrole-2-carboxamide 2b (0.22 g, yield 41%) as a white powder.

MS m/z (ESI): 357 [M+1]

Step 3 cis-Methyl-5-[2-(2-cyano-pyrrolidin-1-yl)-2-oxo-ethylamino]-hexahydro-cyclopenta[c]pyrrole-2-carboxamide hydrochloride 2 cis-Methyl-5-[2-((S)-2-cyano-pyrrolidin-1-yl)-2-oxo-ethylamino]-hexahydro-cyclopenta[c]pyrrole-2-carboxamide 2b was dissolved in 10 mL of ether. Upon cooling by an ice-water bath, 2 mL of hydrochloric acid in ether (0.5 N) was added. The resulting mixture was filtered with a filtering centrifuge to obtain the title compound cis-methyl-5-[2-((S)-2-cyano-pyrrolidin-1-yl)-2-oxo-ethylamino]-hexahydro-cyclopenta[c]pyrrole-2-carboxamide hydrochloride 2 (200 mg) as a white powder.

$^1$H NMR (CD$_3$OD, 400 MHz): δ 4.71 (m, 1H), 3.93 (m, 2H), 3.59-3.28 (m, 10H), 2.64 (m, 2H), 2.34 (m, 2H), 2.17 (m, 2H), 2.08 (m, 2H).

Example 3 cis-(S)-1-{2-[2-(2-Hydroxy-acetyl)-octahydro-cyclopenta[c]pyrrol-5-ylamino]-acetyl}-pyrrolidine-2-carbonitrile hydrochloride

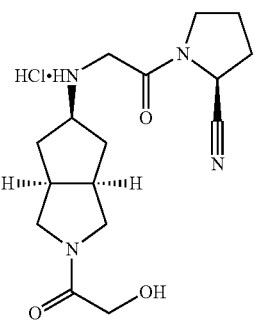

3

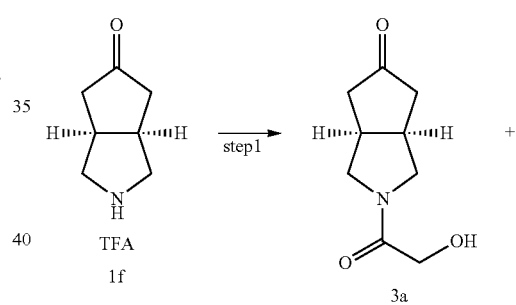

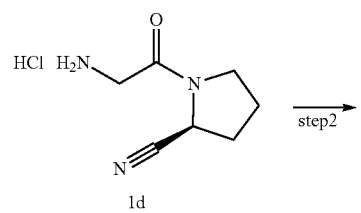

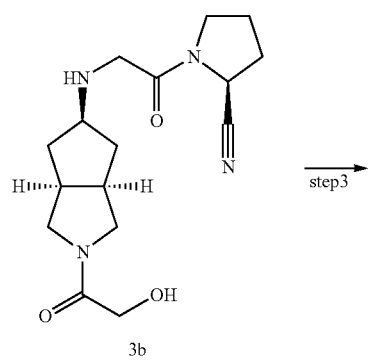

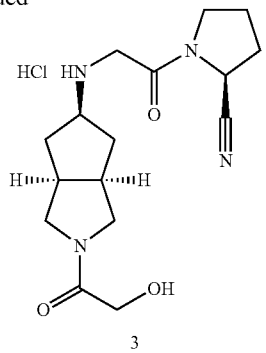

Step 1

Preparation of 2-(2-hydroxy-acetyl)-hexahydro-cyclopenta[c]pyrrol-5-one 3a

Hexahydro-cyclopenta[c]pyrrol-5-one trifluoroacetate 1f (764.8 mg, 3.2 mmol) and 2-hydroxyl ethanoic acid (267.5 mg, 3.52 mmol) were dissolved in 10 mL of acetonitrile. Upon cooling by an ice-water bath, hydroxyacetic acid (1.3 g, 9.6 mmol), 1-ethyl-3-dimethylaminopropyl-carbodiimide hydrochloride (1.23 g, 6.4 mmol) and triethylamine (1.3 mL, 9.6 mmol) were added. The ice-water bath was removed and the reaction mixture was reacted overnight at 25° C. The mixture was concentrated and diluted with 20 mL of ethyl acetate. The mixture was filtered under reduced pressure and the filtrate was washed with 20 mL of water. The organic phase was dried over anhydrous magnesium sulfate, filtered under reduced pressure and concentrated under reduced pressure. The resulting residue was purified by silica gel column chromatography to obtain the title compound 2-(2-hydroxy-acetyl)-hexahydro-cyclopenta[c]pyrrol-5-one 3a (0.375 g, yield 64%) as a colorless oil.

MS m/z (ESI): 184 [M+1]

Step 2

Preparation of cis-(S)-1-{2-[2-(2-hydroxy-acetyl)-octahydro-cyclopenta[c]pyrrol-5-ylamino]-acetyl}-pyrrolidine-2-carbonitrile 3b 2-(2-Hydroxy-acetyl)-hexahydro-cyclopenta[c]pyrrol-5-one 3a (0.375 g, 2.05 mmol) and (S)-1-(2-amino-acetyl)-pyrrolidine-2-carbonitrile hydrochloride 1d (0.78 g, 4.1 mmol) were dissolved in 5 mL of methanol and 10 mL of tetrahydrofuran. After the mixture was reacted at room temperature for 30 minutes, sodium triacetoxyborohydride (0.87 g, 4.1 mmol) was added. Then the reaction mixture was reacted overnight at room temperature. The mixture was concentrated under reduced pressure and diluted with 50 mL of methanol followed by addition of potassium carbonate (2 g, 7 mmol). After stirred for 30 minutes, the mixture was filtered and the filtrate was concentrated under reduced pressure. The resulting residue was purified by silica gel column chromatography to obtain the title compound cis-(S)-1-{2-[2-(2-hydroxy-acetyl)-octahydro-cyclopenta[c]pyrrol-5-ylamino]-acetyl}-pyrrolidine-2-carbonitrile 3b, which was directly used in the next step.

MS m/z (ESI): 357 [M+1]

Step 3

Preparation of cis-(S)-1-{2-[2-(2-hydroxy-acetyl)-octahydro-cyclopenta[c]pyrrol-5-ylamino]-acetyl}-pyrrolidine-2-carbonitrile hydrochloride 3 cis-(S)-1-{2-[2-(2-Hydroxy-acetyl)-octahydro-cyclopenta[c]pyrrol-5-ylamino]-acetyl}-pyrrolidine-2-carbonitrile 3b was dissolved in 10 mL of ether. Upon cooling by an ice-water bath, 2 mL of hydrochloric acid in ether (0.5 N) was added. The resulting mixture was filtered with a filtering centrifuge to obtain the title compound cis-(S)-1-{2-[2-(2-hydroxy-acetyl)-octahydro-cyclopenta[c]pyrrol-5-ylamino]-acetyl}-pyrrolidine-2-carbonitrile hydrochloride 3 (100 mg) as a white powder.

Example 4 cis-(S)-1-{2-[2-(Piperidine-1-carbonyl)-octahydro-cyclopenta[c]pyrrol-5-ylamino]-acetyl}-pyrrolidine-2-carbonitrile hydrochloride

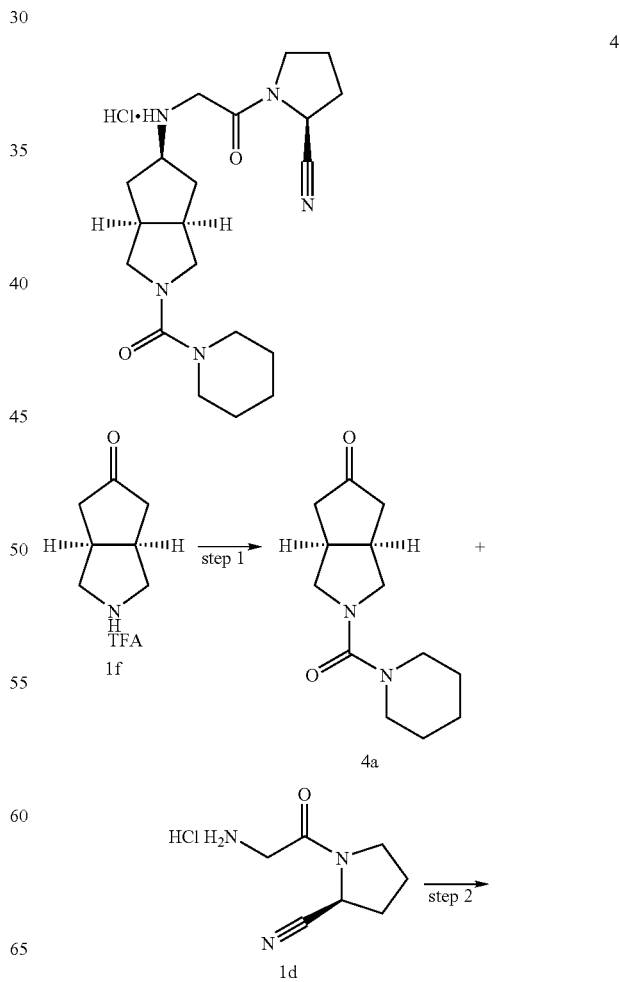

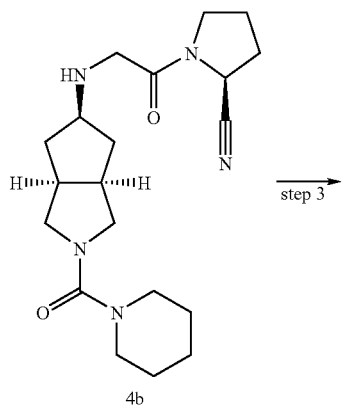

4b

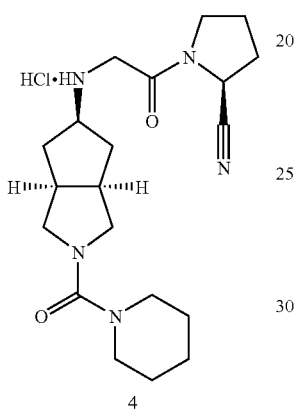

4

Step 1

Preparation of 2-(piperidine-1-carbonyl)-hexahydro-cyclopenta[c]pyrrol-5-one 4a

Hexahydro-cyclopenta[c]pyrrol-5-one trifluoroacetate 1f (478 mg, 2 mmol) was dissolved in 20 mL of dichloromethane with stirring followed by addition of ido[3-(1-piperidine-formyl)imidazole-1-methyl] (0.96 g, 3 mmol) and triethylamine (0.84 mL, 6 mmol). The reaction mixture was stirred overnight at room temperature. The reaction was quenched with 20 mL of water and the mixture was extracted with dichloromethane (50 mL×3). The combined organic extracts were washed with 50 mL of 10% citric acid solution and 50 mL of saturated brine successively, dried over anhydrous magnesium sulfate, filtered and concentrated under reduced pressure. The resulting residue was purified by silica gel column chromatography to obtain the title compound 2-(piperidine-1-carbonyl)-hexahydro-cyclopenta[c]pyrrol-5-one 4a (0.41 g, yield 87%) as a colorless oil.

MS m/z (ESI): 237 [M+1]

Step 2

Preparation of cis-(S)-1-{2-[2-(piperidine-1-carbonyl)-octahydro-cyclopenta[c]pyrrol-5-ylamino]-acetyl}-pyrrolidine-2-carbonitrile 4b 2-(Piperidine-1-carbonyl)-hexahydro-cyclopenta[c]pyrrol-5-one 4a (0.41 g, 1.74 mmol) and (S)-1-(2-amino-acetyl)-pyrrolidine-2-carbonitrile hydrochloride 1d (0.5 g, 2.6 mmol) were dissolved in 50 mL of tetrahydrofuran followed by addition of sodium sulfate (5 g) and 0.05 mL of acetic acid. After the mixture was stirred at room temperature for 30 minutes, sodium triacetoxyborohydride (1.1 g, 5.2 mmol) was added. The reaction mixture was reacted at room temperature for 3 hours and concentrated under reduced pressure. The mixture was diluted with 50 mL of saturated aqueous sodium carbonate and extracted with ethyl acetate (50 mL×3). The combined organic extracts were washed with 50 mL of saturated brine and 50 mL of water successively, dried over anhydrous sodium sulfate, filtered and concentrated under reduced pressure. The resulting residue was purified by silica gel column chromatography to obtain the title compound cis-(S)-1-{2-[2-(piperidine-1-carbonyl)-octahydro-cyclopenta[c]pyrrol-5-ylamino]-acetyl}-pyrrolidine-2-carbonitrile 4b which was directly used in the next step.

MS m/z (ESI): 410 [M+1]

Step 3

Preparation of cis-(S)-1-{2-[2-(piperidine-1-carbonyl)-octahydro-cyclopenta[c]pyrrol-5-ylamino]-acetyl}-pyrrolidine-2-carbonitrile hydrochloride 4 cis-(S)-1-{2-[2-(Piperidine-1-carbonyl)-octahydro-cyclopenta[c]pyrrol-5-ylamino]-acetyl}-pyrrolidine-2-carbonitrile 4b was dissolved in 10 mL of ether. Upon cooling by an ice-water bath, 2 mL of hydrochloric acid in ether (0.5 N) was added. The resulting mixture was filtered with a filtering centrifuge to obtain the title compound cis-(S)-1-{2-[2-(piperidine-1-carbonyl)-octahydro-cyclopenta[c]pyrrol-5-ylamino]-acetyl}-pyrrolidine-2-carbonitrile hydrochloride 4 (0.16 g) as a white solid.

$^{1}$H NMR (CD$_3$OD, 400 MHz): δ 4.83 (dd, 1H, J$_1$=3.0 Hz, J$_2$=5.8 Hz), 4.09 (dd, 2H, J$_1$=J$_2$=13.1 Hz), 3.70-3.30 (m, 10H), 2.72 (m, 2H), 2.47 (m, 2H), 2.31-2.00 (m, 5H), 1.66-1.52 (m, 8H).

Example 5 cis-(S)-1-[2-(2-Acetyl-octahydro-cyclopenta[c]pyrrol-5-ylamino)-acetyl]-pyrrolidine-2-carbonitrile hydrochloride

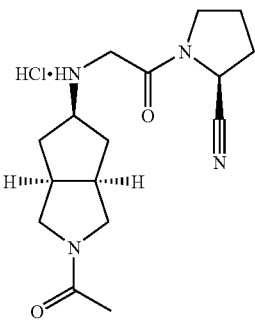

5

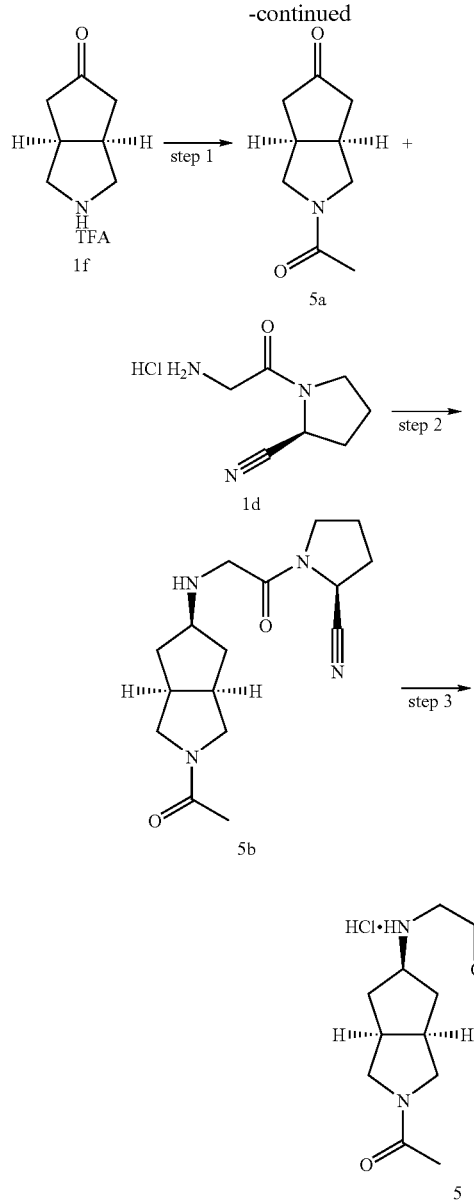

Step 2

Preparation of cis-(S)-1-[2-(2-acetyl-octahydro-cyclopenta[c]pyrrol-5-ylamino)-acetyl]-pyrrolidine-2-carbonitrile 5b 2-Acetyl-hexahydro-cyclopenta[c]pyrrol-5-one 5a (0.36 g, 2.15 mmol) and (S)-1-(2-amino-acetyl)-pyrrolidine-2-carbonitrile hydrochloride 1d (0.614 g, 3.23 mmol) were dissolved in 50 mL of tetrahydrofuran followed by addition of 5 g of sodium sulfate and 0.05 mL of acetic acid. After the mixture was stirred at room temperature for 30 minutes, sodium triacetoxyborohydride (1.37 g, 6.46 mmol) was added and the mixture was reacted for another 3 hours. The mixture was concentrated under reduced pressure and diluted with 50 mL of saturated aqueous sodium carbonate. The reaction mixture was extracted with ethyl acetate (50 mL×3). The combined organic extracts were washed with 50 mL of saturated brine and 50 mL of water successively, dried over anhydrous magnesium sulfate, filtered and concentrated under reduced pressure. The resulting residue was purified by silica gel column chromatography to obtain the title compound cis-(S)-1-[2-(2-acetyl-octahydro-cyclopenta[c]pyrrol-5-ylamino)-acetyl]-pyrrolidine-2-carbonitrile 5b which was directly used in the next step.

MS m/z (ESI): 305.5 [M+1]

Step 3

Preparation of cis-(S)-1-[2-(2-acetyl-octahydro-cyclopenta[c]pyrrol-5-ylamino)-acetyl]-pyrrolidine-2-carbonitrile hydrochloride 5 cis-(S)-1-[2-(2-Acetyl-octahydro-cyclopenta[c]pyrrol-5-ylamino)-acetyl]-pyrrolidine-2-carbonitrile 5b obtained from the above step was dissolved in 20 mL of ether. Upon cooling by an ice-water bath, 4 mL of hydrochloric acid in ether (0.5 N) was added. The resulting mixture was filtered with filtering centrifuge to obtain the title compound cis-(S)-1-[2-(2-acetyl-octahydro-cyclopenta[c]pyrrol-5-ylamino)-acetyl]-pyrrolidine-2-carbonitrile hydrochloride 5 (0.23 g) as a white powder.

$^1$H NMR (CD$_3$OD, 400 MHz): δ 4.71 (m, 1H), 3.92 (m, 2H), 3.69-3.37 (m, 7H), 2.69 (m, 2H), 2.33 (m, 2H), 2.13 (m, 2H), 2.04-2.00 (m, 5H), 1.48 (m, 2H).

Example 6 cis-5-[2-((S)-2-Cyano-pyrrolidin-1-yl)-2-oxo-ethylamino]-hexahydro-cyclopenta[c]pyrrole-2-carboxylic acid isopropylamide hydrochloride

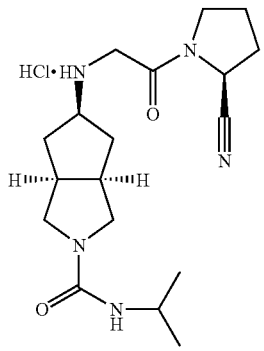

6

Step 1

Preparation of 2-acetyl-hexahydro-cyclopenta[c]pyrrol-5-one 5a

Hexahydro-cyclopenta[c]pyrrol-5-one trifluoroacetate 1f (717 mg, 3 mmol) was dissolved in 20 mL of acetonitrile followed by addition of di-tert-butyl dicarbonate (0.42 mL, 4.5 mmol) and triethylamine (0.98 mL, 9 mmol) upon cooling by an ice-water bath. The reaction mixture was stirred overnight at the same temperature. The mixture was concentrated and diluted with 50 mL of water. The mixture was extracted with ethyl acetate (50 mL×3). The combined organic extracts were washed with 50 mL of saturated brine, dried over anhydrous magnesium sulfate, filtered and concentrated under reduced pressure. The resulting residue was purified by silica gel column chromatography to obtain the title compound 2-acetyl-hexahydro-cyclopenta[c]pyrrol-5-one 5a (0.36 g, yield 72%) as a colorless oil MS m/z (ESI): 168.4 [M+1]

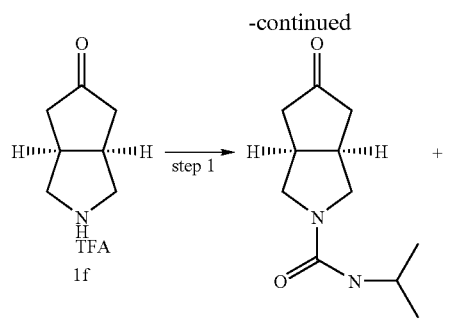

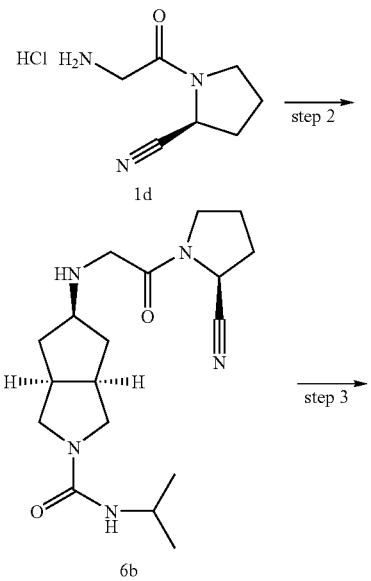

Step 1

Preparation of N-isopropyl-5-oxo-hexahydro-cyclopenta[c]pyrrole-2-carboxamide 6a Hexahydro-cyclopenta[c]pyrrol-5-one trifluoroacetate 1f (717 mg, 3 mmol) was dissolved in 20 mL of dichloromethane with stirring upon cooling by an ice-water bath, followed by addition of isocyanate (9 mL, 9 mmol) and triethylamine (1.7 mL, 12 mmol). The reaction mixture was reacted overnight at room temperature and diluted with 50 mL of water. The mixture was extracted with dichloromethane (50 mL×3). The combined organic extracts were washed with 10% citric acid solution (50 mL) and 50 mL of saturated brine successively, dried over anhydrous magnesium sulfate, filtered and concentrated under reduced pressure. The resulting residue was purified by silica gel column chromatography to obtain N-isopropyl-5-oxo-hexahydro-cyclopenta[c]pyrrole-2-carboxylic acid isopropylamide 6a (0.3 g, yield 47.6%) as a colorless oil.

MS m/z (ESI): 211 [M+1]

Step 2

Preparation of cis-5-[2-((S)-2-cyano-pyrrolidin-1-yl)-2-oxo-ethylamino]-hexahydro-cyclopenta[c]pyrrole-2-carboxylic acid isopropylamide 6b N-isopropyl-5-oxo-hexahydro-cyclopenta[c]pyrrole-2-carboxylic acid isopropylamide 6a (0.3 g, 1.43 mmol) and (S)-1-(2-amino-acetyl)-pyrrolidine-2-carbonitrile hydrochloride 1d (0.407 g, 2.14 mmol) were dissolved in 50 mL of tetrahydrofuran followed by addition of 5 g of sodium sulfate and 0.05 mL of acetic acid. After the reaction mixture was stirred at room temperature for 30 minutes, sodium triacetoxyborohydride (0.9 g, 4.3 mmol) was added and the mixture was stirred for 3 hours. The mixture was concentrated under reduced pressure and diluted with 50 mL of saturated aqueous sodium carbonate. The reaction mixture was extracted with ethyl acetate (50 mL×3). The combined organic extracts were washed with 50 mL of saturated brine and 50 mL of water successively, dried over anhydrous magnesium sulfate, filtered and concentrated under reduced pressure. The residue was purified by silica gel column chromatography to obtain the title compound cis-5-[2-((S)-2-cyano-pyrrolidin-1-yl)-2-oxo-ethylamino]-hexahydro-cyclopenta[c]pyrrole-2-carboxylic acid isopropylamide 6b, which was directly used in the next step.

MS m/z (ESI): 384 [M+1]

Step 3

Preparation of cis-5-[2-((S)-2-cyano-pyrrolidin-1-yl)-2-oxo-ethylamino]-hexahydro-cyclopenta[c]pyrrole-2-carboxylic acid isopropylamide hydrochloride 6 cis-5-[2-((S)-2-Cyano-pyrrolidin-1-yl)-2-oxo-ethylamino]-hexahydro-cyclopenta[c]pyrrole-2-carboxylic acid isopropylamide 6b obtained from the above step was dissolved in 10 mL of ether. Upon cooling by an ice-water bath, 2 mL of hydrochloric acid in ether (0.5 N) was added. The resulting mixture was filtered with filtering centrifuge to obtain the title compound cis-5-[2-((S)-2-cyano-pyrrolidin-1-yl)-2-oxo-ethylamino]-hexahydro-cyclopenta[c]pyrrole-2-carboxylic acid isopropylamide hydrochloride 6 (80 mg) as a white powder.

¹H NMR (CD₃OD, 400 MHz): δ 4.70 (m, 1H), 3.92 (m, 2H), 3.76-3.32 (m, 8H), 2.63-1.41 (m, 10H), 1.01 (d, 6H, J=6 Hz).

Example 7 cis-(S)-1-{2-[2-(Morpholine-4-carbonyl)-octahydro-cyclopenta[c]pyrrol-5-ylamino]-acetyl}-pyrrolidine-2-carbonitrile hydrochloride

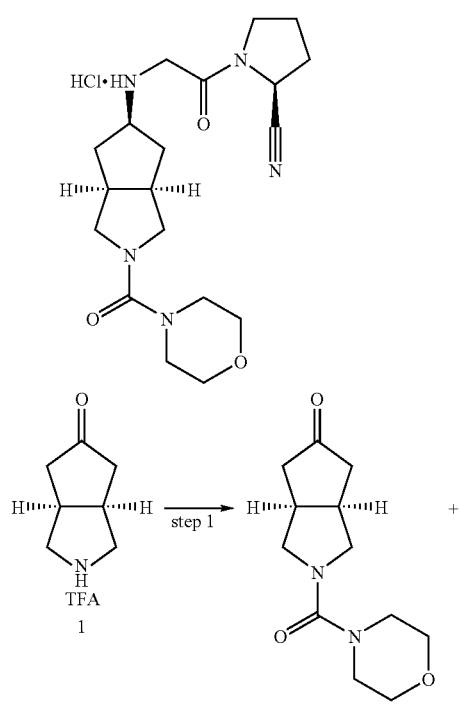

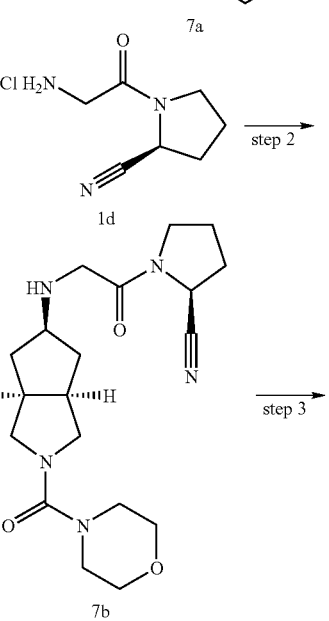

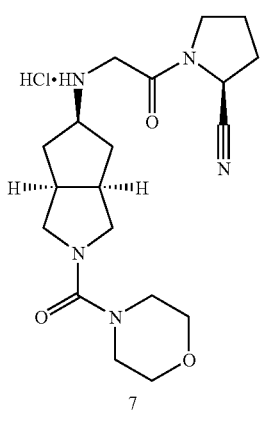

Step 1

Preparation of 2-(morpholine-4-carbonyl)-hexahydro-cyclopenta[c]pyrrol-5-one 7a

Hexahydro-cyclopenta[c]pyrrol-5-one trifluoroacetate 1f (574 mg, 2.4 mmol) was dissolved in 20 mL of acetonitrile with stirring followed by addition of potassium carbonate (0.397 g, 2.88 mmol), and morpholine-4-carbonyl chloride (0.323 mL, 2.64 mmol) upon cooling by an ice-water bath. The reaction mixture was reacted overnight at the same temperature. The mixture was concentrated under reduced pressure and diluted with 50 mL of water. The mixture was extracted with ethyl acetate (50 mL×3). The combined organic extracts were washed with 50 mL of saturated brine, dried over anhydrous magnesium sulfate, filtered and concentrated under reduced pressure. The resulting residue was purified by silica gel column chromatography to obtain the title compound 2-(morpholine-4-carbonyl)-hexahydro-cyclopenta[c]pyrrol-5-one 7a (0.572 g, yield 77.3%) as a colorless oil.

MS m/z (ESI): 239 [M+1]

Step 2

Preparation of cis-(S)-1-{2-[2-(morpholine-4-carbonyl)-octahydro-cyclopenta[c]pyrrol-5-ylamino]-acetyl}-pyrrolidine-2-carbonitrile 7b 2-(Morpholine-4-carbonyl)-hexahydro-cyclopenta[c]pyrrol-5-one 7a (0.64 g, 2.69 mmol) and (S)-1-(2-amino-acetyl)-pyrrolidine-2-carbonitrile hydrochloride 1d (0.764 g, 4.03 mmol) were dissolved in 50 mL of tetrahydrofuran followed by addition of 5 g of sodium sulfate and 0.05 mL of acetic acid. After the mixture was stirred at room temperature for 30 minutes, sodium triacetoxyborohydride (1.71 g, 8.07 mmol) was added and the mixture was reacted for another 3 hours. The mixture was concentrated under reduced pressure and diluted with 50 mL of saturated aqueous sodium carbonate. The reaction mixture was extracted with ethyl acetate (50 mL×3). The combined organic extracts were washed with 50 mL of saturated brine and 50 mL of water successively, dried over anhydrous magnesium sulfate, filtered and concentrated under reduced pressure. The resulting residue was purified by silica gel column chromatography to obtain the title compound cis-(S)-1-{2-[2-(morpholine-4-carbonyl)-octahydro-cyclopenta[c]pyrrol-5-ylamino]-acetyl}-pyrrolidine-2-carbonitrile 7b which was directly used in the next step.

MS m/z (ESI): 376.7 [M+1]

Step 3

Preparation of cis-1-{2-[(S)-2-(morpholine-4-carbonyl)-octahydro-cyclopenta[c]pyrrol-5-ylamino]-acetyl}-pyrrolidine-2-carbonitrile hydrochloride 7 cis-1-{2-[(S)-2-(Morpholine-4-carbonyl)-octahydro-cyclopenta[c]-pyrrol-5-ylamino]-acetyl}-pyrrolidine-2-carbonitrile 7b obtained from the above step was dissolved in 10 mL of ether. Upon cooling by an ice-water bath, 2 mL of hydrochloric acid in ether (0.5 N) was added. The resulting mixture was filtered with a filtering centrifuge to obtain the title compound cis-1-{2-[(S)-2-(morpholine-4-carbonyl)-octahydro-cyclopenta[c]pyrrol-5-ylamino]-acetyl}-pyrrolidine-2-carbonitrile hydrochloride 7 (30 mg, yield 3%) as a white powder.

Example 8 cis-(S)-1-{2-[2-(Pyrrolidine-1-carbonyl)-octahydro-cyclopenta[c]pyrrol-5-ylamino]-acetyl}-pyrrolidine-2-carbonitrile hydrochloride

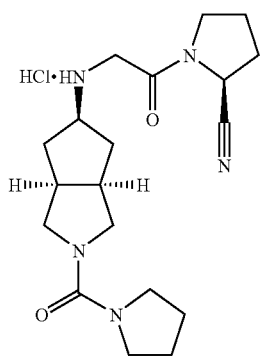

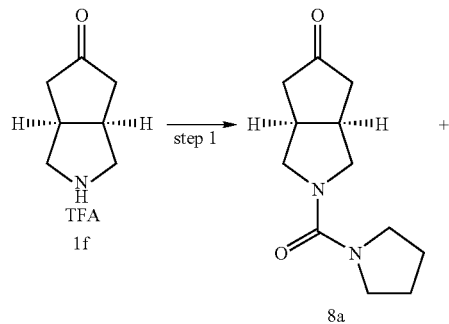

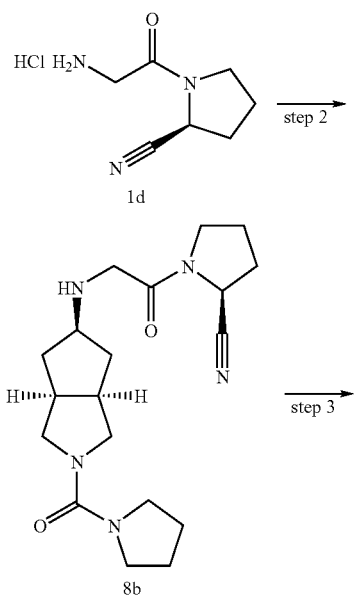

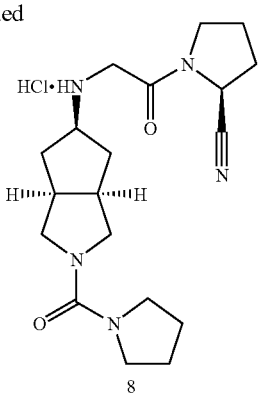

Step 1

Preparation of 2-(pyrrolidine-1-carbonyl)-hexahydro-cyclopenta[c]pyrrol-5-one 8a Hexahydro-cyclopenta[c]pyrrol-5-one trifluoroacetate 1f (478 mg, 2 mmol) was dissolved in 20 mL of dichloromethane followed by addition of pyrrolidine-1-carbonyl chloride (0.276 mL, 2.5 mmol) and triethylamine (0.84 mL, 6 mmol). The reaction mixture was reacted overnight at room temperature. The mixture was adjusted to pH 4 with a solution of 10% citric acid. The mixture was extracted with dichloromethane (50 mL×3). The combined organic extracts were washed with 50 mL of saturated brine, dried over anhydrous magnesium sulfate, filtered and concentrated under reduced pressure. The resulting residue was purified by silica gel column chromatography to obtain the title compound 2-(pyrrolidine-1-carbonyl)-hexahydro-cyclopenta[c]pyrrol-5-one 8a (0.26 g, yield 58.5%) as a colorless oil.

MS m/z (ESI): 223 [M+1]

Step 2

Preparation of cis-(S)-1-{2-[2-(pyrrolidine-1-carbonyl)-octahydro-cyclopenta[c]pyrrol-5-ylamino]-acetyl}-pyrrolidine-2-carbonitrile 8b 2-(Pyrrolidine-1-carbonyl)-hexahydro-cyclopenta[c]pyrrol-5-one 8a (0.26 g, 1.17 mmol) and (S)-1-(2-amino-acetyl)-pyrrolidine-2-carbonitrile hydrochloride 1d (0.33 g, 1.75 mmol) were dissolved in 50 mL of tetrahydrofuran followed by addition of 5 g of sodium sulfate and 0.05 mL of acetic acid. After the mixture was reacted at room temperature for 30 minutes, sodium triacetoxyborohydride (0.75 g, 3.5 mmol) was added and the reaction mixture was reacted for 3 hours. The mixture was concentrated under reduced pressure and diluted with 50 mL of saturated aqueous sodium carbonate. The reaction mixture was extracted with ethyl acetate (50 mL×3). The combined organic extracts were washed with 50 mL of saturated brine and 50 mL of water, dried over anhydrous magnesium sulfate, filtered and concentrated under reduced pressure. The resulting residue was purified by silica gel column chromatography to obtain the title compound cis-(S)-1-{2-[2-(pyrrolidine-1-carbonyl)-octahydro-cyclopenta[c]pyrrol-5-ylamino]-acetyl}-pyrrolidine-2-carbonitrile 8b, which was directly used in the next step.

MS m/z (ESI): 396 [M+1]

Step 3

Preparation of cis-(S)-1-{2-[2-(pyrrolidine-1-carbonyl)-octahydro-cyclopenta[c]pyrrol-5-ylamino]-acetyl}-pyrrolidine-2-carbonitrile hydrochloride cis-(S)-1-{2-[2-(Pyrrolidine-1-carbonyl)-octahydro-cyclopenta[c]pyrrol-5-ylamino]-acetyl}-pyrrolidine-2-carbonitrile 8b obtained from the above step was dissolved in 10 mL of ether. Upon cooling by an ice-water bath, 2 mL of hydrochloric acid in ether (0.5 N) was added. The resulting mixture was filtered with a filtering centrifuge to obtain the title compound cis-(S)-1-{2-[2-(pyrrolidine-1-carbonyl)-octahydro-cyclopenta[c]pyrrol-5-ylamino]-acetyl}-pyrrolidine-2-carbonitrile hydrochloride 8 (90 mg) as a white powder.

$^1$H NMR (CD$_3$OD, 400 MHz): δ 4.72 (m, 1H), 4.09 (m, 2H), 3.43-3.30 (m, 11H), 2.62 (m, 2H), 2.35 (m, 2H), 2.18 (m, 2H), 2.08 (m, 2H), 1.77 (m, 4H).

Example 9 cis-5-[2-((S)-2-Cyano-pyrrolidin-1-yl)-2-oxo-ethylamino]-N,N-dimethyl-hexahydro-cyclopenta[c]pyrrole-2-carboxamide trifluoroacetate

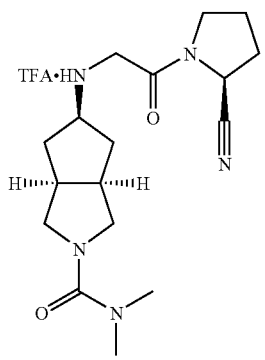

9

5-[2-((S)-2-Cyano-pyrrolidin-1-yl)-2-oxo-ethylamino]-N,N-dimethyl-hexahydro-cyclopenta[c]pyrrole-2-carboxylic acid dimethylamide 1h obtained from Example 1 was dissolved in 10 mL of dichloromethane followed by addition of 2 mL of trifluoroacetic acid upon cooling by an ice-water bath. The reaction mixture was stirred for 30 minutes. The resulting mixture was filtered with a filtering centrifuge to obtain the title compound cis-5-[2-((S)-2-cyano-pyrrolidin-1-yl)-2-oxo-ethylamino]-N,N-dimethyl-hexahydro-cyclopenta[c]pyrrole-2-carboxamide trifluoroacetate 9 (201 mg) as a white powder.

$^1$H NMR (CDCl$_3$, 400 MHz): δ 4.74 (t, 1H, J=5.2 Hz), 3.98 (d, 1H, J=15.6 Hz), 3.79 (d, 1H, J=15.6 Hz), 3.57-3.25 (m, 7H), 2.75 (s, 6H), 2.55 (m, 2H), 2.33 (m, 2H), 2.20-2.08 (m, 4H), 1.74 (m, 2H).

Example 10 trans-5-[2-((S)-2-Cyano-pyrrolidin-1-yl)-2-oxo-ethylamino]-N,N-dimethyl-hexahydro-cyclopenta[c]pyrrole-2-carboxamide trifluoroacetate

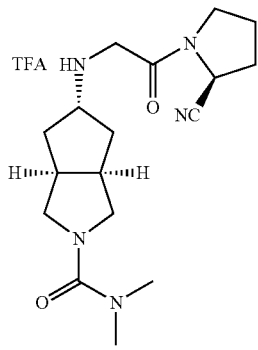

10

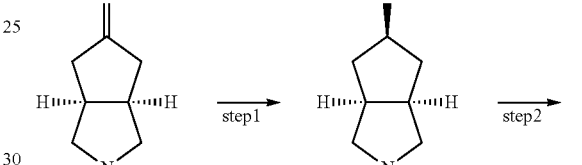

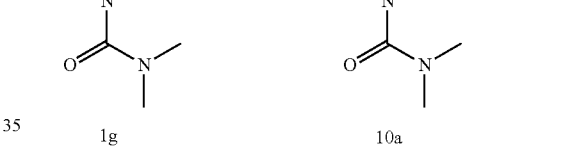

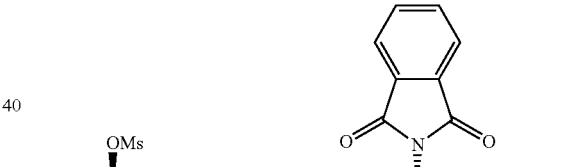

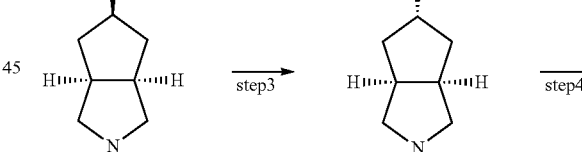

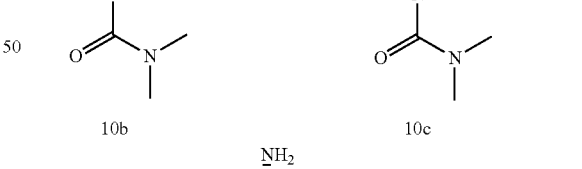

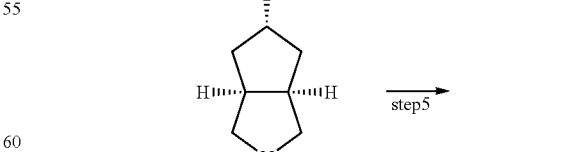

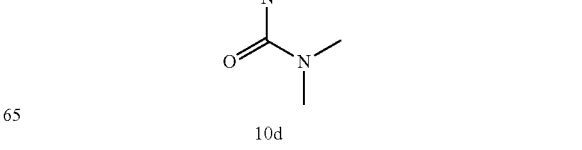

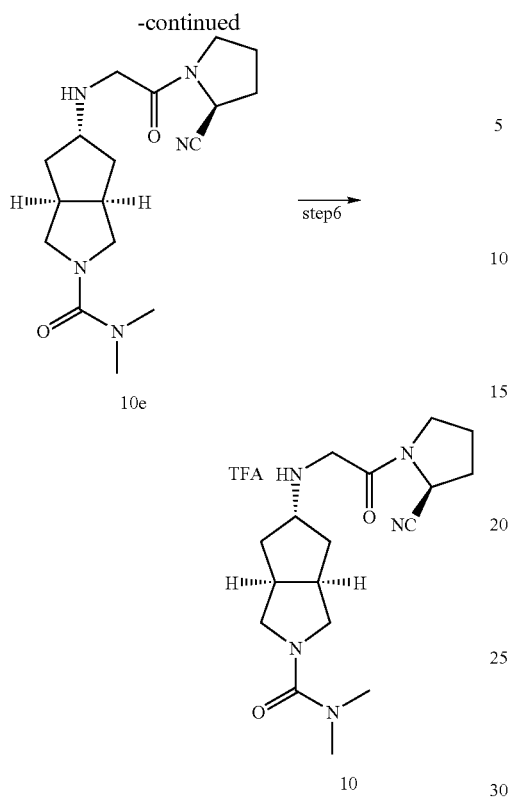

Step 1

Preparation of cis-5-hydroxy-hexahydro-cyclopenta[c]pyrrole-2-carboxamide N,N-dimethylamide 10a In a dry three-necked flask, N,N-dimethyl-5-oxo-hexahydro-cyclopenta[c]pyrrole-2-carboxamide 1g (1.58 g, 8.06 mmol) was dissolved in 30 mL of tetrahydrofuran with stirring under nitrogen atmosphere. The mixture was cooled to −25° C. followed by dropwise addition of a solution of lithium tri-tert-butoxyaluminium hydride (2.45 g, 9.6 mmol) in 30 mL of tetrahydrofuran. After the reaction mixture was reacted for 2.5 hours at the same temperature, the reaction was quenched with water. The mixture was diluted with 20 mL of saturated aqueous ammonium chloride and warmed up to room temperature. The layers were separated and then the aqueous layer was extracted with dichloromethane (50 mL×3). The combined organic extracts were washed with 50 mL of saturated brine, dried over anhydrous magnesium sulfate, filtered and concentrated under reduced pressure. The resulting residue was purified by silica gel column chromatography to obtain the title compound cis-5-hydroxy-hexahydro-cyclopenta[c]pyrrole-2-carboxylic acid N,N-dimethylamide 10a (1.27 g, yield 80%) as a colorless oil.

MS m/z (ESI): 199 [M+1]

Step 2

Preparation of cis-methanesulfonic acid 2-dimethylcarbamoyl-octahydro-cyclopenta[c]pyrrol-5-yl ester 10b In a dry one-necked flask, cis-5-hydroxy-hexahydro-cyclopenta[c]pyrrole-2-carboxylic acid dimethylamide 10a (1.69 g, 8.5 mmol) was dissolved in 30 mL of dichloromethane with stirring under nitrogen atmosphere. Upon cooling by an ice-salt bath to −5° C.~0° C., triethylamine (1.66 mL, 14.45 mmol) and methanesulfonyl chloride (2.2 g, 21.74 mmol) were added successively. The reaction mixture was stirred for 30 minutes and warmed up to room temperature. After the reaction mixture was reacted for 2 hours, the mixture was concentrated under reduced pressure and diluted with 20 mL of water. The reaction mixture was extracted with ethyl acetate (50 mL×6). The combined organic extracts were washed with 50 mL of saturated brine, dried over anhydrous magnesium sulfate, filtered and concentrated under reduced pressure. The resulting residue was purified by silica gel column chromatography to obtain the title compound cis-methanesulfonic acid 2-dimethylcarbamoyl-octahydro-cyclopenta[c]pyrrol-5-yl ester 10b (1.94 g, yield 83%) as a white solid.

MS m/z (ESI): 277 [M+1]

Step 3

Preparation of trans-5-(1,3-dioxo-1,3-dihydro-isoindol-2-yl)-hexahydro-cyclopenta[c]pyrrole-2-carboxylic acid dimethylamide 10c In a dry one-necked flask, methanesulfonic acid 2-dimethylcarbamoyl-octahydro-cyclopenta[c]pyrrol-5-yl ester 10b (1 g, 3.6 mmol) was added in 20 mL of N,N-dimethylformamide and phthalimide potassium salt (993 mg, 5.4 mmol) with stirring under nitrogen atmosphere. The reaction mixture was warmed up to 70° C. and reacted for 3 hours. The mixture was concentrated under reduced pressure to remove N,N-dimethylformamide and the residue was diluted with 20 mL of water. The mixture was extracted with ethyl acetate (50 mL×3). The combined organic extracts were washed with 50 mL of saturated brine, dried over anhydrous magnesium sulfate, filtered and concentrated under reduced pressure to obtain the title compound trans-5-(1,3-dioxo-1,3-dihydro-isoindol-2-yl)-hexahydro-cyclopenta[c]pyrrole-2-carboxylic acid dimethylamide 10c (1.06 g, yield 90%) as a white solid which was directly used in the next step.

MS m/z (ESI): 328 [M+1]

Step 4

Preparation of trans-5-amino-hexahydro-cyclopenta[c]pyrrole-2-carboxylic acid N,N-dimethylamide 10d In a one-necked flask, trans-5-(1,3-Dioxo-1,3-dihydro-isoindol-2-yl)-hexahydro-cyclopenta[c]pyrrole-2-carboxylic acid dimethylamide 10c was dissolved in 20 mL of ethanol (95%) with stirring followed by addition of hydrazine (490 mg, 15.3 mmol). The reaction mixture was heated to reflux for 8 hours, and then cooled to room temperature. The mixture was filtered and the filtrate was concentrated under reduced pressure to obtain a white solid. The resulting solid was dissolved in 25 mL of methanol, filtered and then the filtrate was concentrated under reduced pressure. The resulting residue was purified by alumina base column chromatography to obtain the title compound trans-5-amino-hexahydro-cyclopenta[c]pyrrole-2-carboxylic acid N,N-dimethylamide 10d (290 mg, yield 48%) as a colorless oil.

MS m/z (ESI): 198 [M+1]

Step 5

Preparation of trans-5-[2-((S)-2-cyano-pyrrolidin-1-yl)-2-oxo-ethylamino]-N,N-dimethyl-hexahydro-cyclopenta[c]pyrrole-2-carboxamide 10e In a dry one-necked flask, trans-1-(2-chloro-ethyl)-pyrrole-2-cyano (334 mg, 1.94 mmol) and a solution of trans-5-amino-hexahydro-cyclopenta[c]pyrrole-2-carboxylic acid N,N-dimethylamide 10d (290 mg, 1.46 mmol) was dissolved in 20 mL of dichloromethane. The reaction mixture was heated to reflux for 48 hours. The mixture was concentrated under reduced pressure. The resulting residue was purified by silica gel column chromatography to obtain the title compound trans-5-[2-((S)-2-cyano-pyrrolidin-1-yl)-2-oxo-ethylamino]-N,N-dimethyl-hexahydro-cyclopenta[c]pyrrole-2-carboxamide 10e, which was directly used in the next step.

Step 6

Preparation of trans-5-[2-((S)-2-cyano-pyrrolidin-1-yl)-2-oxo-ethylamino]-N,N-dimethyl-hexahydro-cyclopenta[c]pyrrole-2-carboxamide trifluoroacetate 10 trans-5-[2-((S)-2-Cyano-pyrrolidin-1-yl)-2-oxo-ethylamino]-N,N-dimethyl-hexahydro-cyclopenta[c]pyrrole-2-carboxamide 10e obtained from the above step was dissolved in 10 mL of dichloromethane with stirring followed by addition of 2 mL of trifluoroacetic acid. The reaction mixture was stirred for 30 minutes to obtain the title compound trans-5-[2-((S)-2-cyano-pyrrolidin-1-yl)-2-oxo-ethylamino]-N,N-dimethyl-hexahydro-cyclopenta[c]pyrrole-2-carboxamide trifluoroacetate 10 (201 mg) as a white solid.

MS m/z (ESI): 334 [M+1]

$^1$H NMR (CDCl$_3$, 400 MHz): δ 4.65 (m, 1H), 3.93 (d, 1H, J=15.2 Hz), 3.74 (d, 1H, J=15.2 Hz), 3.69-3.19 (m, 7H), 2.77 (s, 6H), 2.18-1.96 (m, 10H).

Example 11

5-[2-((S)-2-Cyano-pyrrolidin-1-yl)-2-oxo-ethylamino]-5-methyl-hexahydro-cyclopenta[c]pyrrole-2-carboxylic acid dimethylamide p-toluenesulfonate

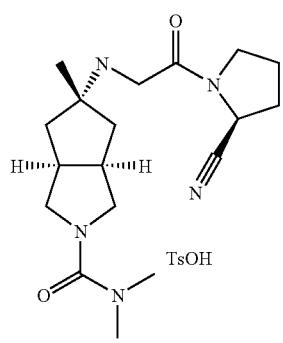

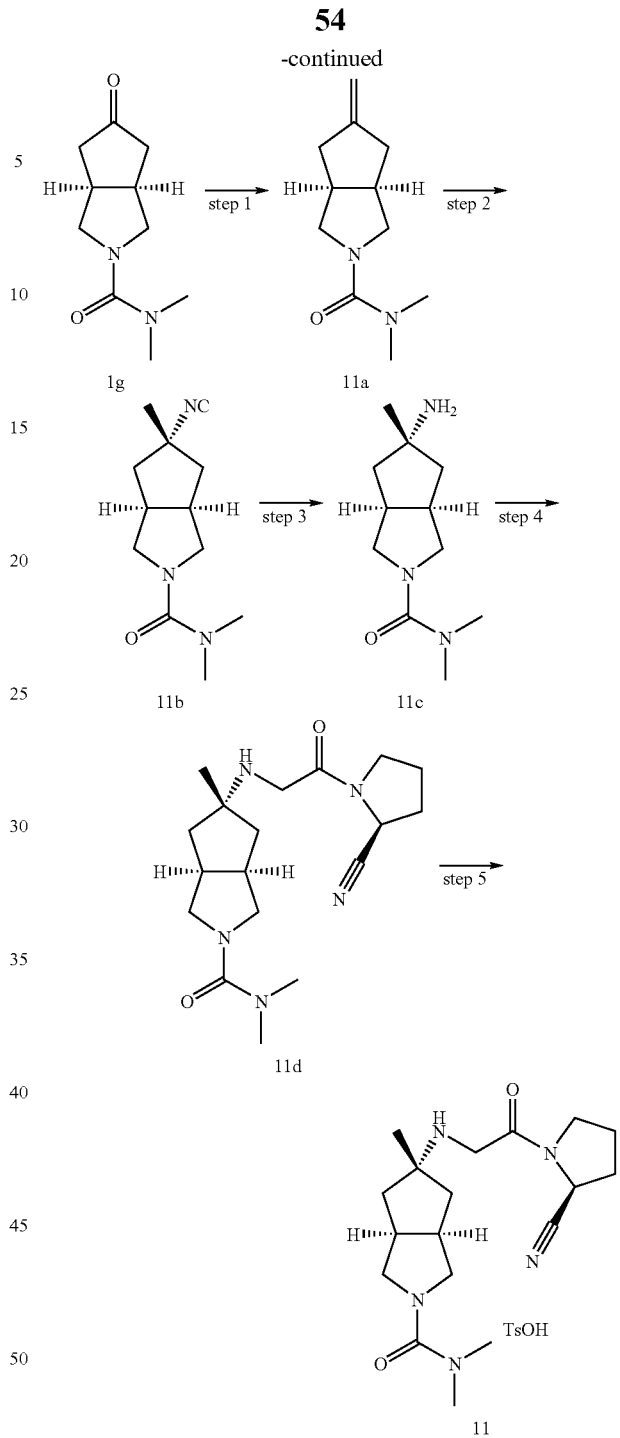

Step 1

Preparation of 5-methylene-hexahydro-cyclopenta[c]pyrrole-2-carboxylic acid dimethylamide Potassium tert-butoxide (7.17 g, 0.064 mol) and methyltriphenylphosphonium iodide (25.8 g, 0.064 mol) were dissolved in 150 mL of toluene under nitrogen atmosphere. The reaction mixture was heated to reflux for 3 hours, and cooled to room temperature. A solution of N,N-dimethyl-5-oxo-hexahydro-cyclopenta[c]pyrrole-2-carboxylate 1g (5.0 g, 0.0255 mol) in toluene was added. The reaction mixture was stirred for 30 minutes. The reaction was monitored by TLC until the disappearance of the starting materials. The mixture was diluted with 30 mL of water and 30 mL of saturated brine and extracted with ethyl acetate (200 mL×4). The combined organic extracts were dried over anhydrous magnesium sulfate, filtered and concentrated under reduced pressure. The resulting residue was purified by silica gel column chromatography to obtain the title compound 5-methylene-hexahydro-cyclopenta[c]pyrrole-2-carboxylic acid dimethylamide 11a (4.0 g, yield 80%) as a light yellow oil.

MS m/z (ESI): 195.2 [M+1]

Step 2

Preparation of 5-isocyano-5-methyl-hexahydro-cyclopenta[c]pyrrole-2-carboxylic acid dimethylamide 5-Methylene-hexahydro-cyclopenta[c]pyrrole-2-carboxylic acid dimethylamide 11a (1.6 g, 8.23 mmol) was dissolved in 30 mL of dichloromethane with stirring followed by addition of trimethylsilyl cyanide (4.08 g, 41.2 mmol) and silver perchlorate (5.12 g, 24.7 mmol) under nitrogen atmosphere. The reaction mixture was stirred overnight at room temperature and then some of the reaction mixture was treated with saturated aqueous sodium carbonate. The reaction was monitored by TLC, which showed that there remained most of the starting materials. Then the mixture was treated with 20 mL of saturated aqueous sodium carbonate upon cooling by an ice-water bath, and the reaction released heat. After 10 minutes, the mixture was filtered to remove the residue. The separated aqueous phase was extracted with ethyl acetate (50 mL×4). The combined organic extracts were dried over anhydrous magnesium sulfate, filtered and concentrated under reduced pressure. The resulting residue was purified by silica gel column chromatography to obtain 5-isocyano-5-methyl-hexahydro-cyclopenta[c]pyrrole-2-carboxylic acid dimethylamide 11b (0.33 g, yield 18.1%) as a light yellow oil.

GC-MS: 221.1 [M$^+$]
$^1$H NMR (CDCl$_3$, 400 MHz): δ 3.31 (m, 4H), 2.97 (m, 2H), 2.84 (s, 6H), 2.32 (m, 2H), 1.52 (s, 3H), 1.46 (m, 2H).

Step 3

Preparation of 5-amino-5-methyl-hexahydro-cyclopenta[c]pyrrole-2-carboxylic acid dimethylamide To a solution of 5-isocyano-5-methyl-hexahydro-cyclopenta[c]pyrrole-2-carboxylic acid dimethylamide 11b (0.388 g, 1.75 mmol) in 15 mL of ethanol was added 0.38 mL of hydrochloric acid (6 N) upon cooling by an ice-water bath. The reaction mixture was warmed up to room temperature and stirred for 1.5 hours. The reaction was monitored by TLC until the disappearance of the starting materials. The mixture was quenched with 20 mL of saturated aqueous sodium carbonate. The mixture was extracted with dichloromethane (50 mL×3). The combined organic extracts were evaporated to dryness. The resulting residue was purified by silica gel column chromatography to obtain the title compound 5-amino-5-methyl-hexahydro-cyclopenta[c]pyrrole-2-carboxylic acid dimethylamide 11c (0.28 g, yield 75.7%) as a yellow oil.

MS m/z (ESI): 212.2 [M+1]

Step 4

Preparation of 5-[2-((S)-2-cyano-pyrrolidin-1-yl)-2-oxo-ethylamino]-5-methyl-hexahydro-cyclopenta[c]pyrrole-2-carboxylic acid dimethylamide 5-Amino-5-methyl-hexahydro-cyclopenta[c]pyrrole-2-carboxylic acid dimethylamide 11c (200 mg, 0.92 mmol) was dissolved in 8 mL of N,N-dimethylformamide, followed by addition of 1-(2-chloro-acetyl)-pyrrolidine-2-cyano (175 mg, 1.02 mmol). The reaction mixture was reacted overnight at room temperature. The mixture was concentrated under reduced pressure at 40~50° C. to remove N,N-dimethylformamide. The resulting residue was purified by silica gel column chromatography to obtain the title compound 5-[2-((S)-2-cyano-pyrrolidin-1-yl)-2-oxo-ethylamino]-5-methyl-hexahydro-cyclopenta[c]pyrrole-2-carboxylic acid dimethylamide 11d (0.135 g, yield 42.3%) as a colorless oil. And 5-amino-5-methyl-hexahydro-cyclopenta[c]pyrrole-2-carboxylic acid dimethylamide 11c (130 mg) was recovered.

MS m/z (ESI): 348.2 [M+1]

Step 5

Preparation of 5-[2-((S)-2-cyano-pyrrolidin-1-yl)-2-oxo-ethylamino]-5-methyl-hexahydro-cyclopenta[c]pyrrole-2-carboxylic acid dimethylamide p-toluenesulfonate 5-[2-((S)-2-Cyano-pyrrolidin-1-yl)-2-oxo-ethylamino]-5-methyl-hexahydro-cyclopenta[c]pyrrole-2-carboxylic acid dimethylamide 11d (20 mg, 0.057 mmol) and p-toluenesulfonic acid monohydrate (12 mg, 0.063 mmol) were dissolved in 2 mL of dichloromethane with stirring upon cooling by an ice-water bath. The reaction mixture was stirred for 10 minutes at the same temperature and the ice-water bath was removed. The mixture was concentrated under reduced pressure to obtain an oil. The mixture was treated with 5 mL of ethyl acetate with stirring to produce a white precipitate. The mixture was filtered under reduced pressure to obtain the title compound 5-[2-((S)-2-cyano-pyrrolidin-1-yl)-2-oxo-ethylamino]-5-methyl-hexahydro-cyclopenta[c]pyrrole-2-carboxylic acid dimethylamide p-toluenesulfonate 11 (0.026 g, yield 86.8%) as a white solid.

MS m/z (ESI): 348.2 [M+1]
$^1$H NMR (CDCl$_3$, 400 MHz): δ 7.68 (d, 2H), 7.17 (d, 2H), 3.72 (m, 1H), 3.68 (m, 1H), 3.58 (m, 1H), 3.30 (m, 4H), 2.98 (s, 2H), 2.81 (s, 6H), 2.55 (m, 2H), 2.22 (m, 4H), 2.05 (m, 2H), 1.62 (m, 2H), 1.56 (s, 3H).

Example 12

5-[2-((S)-2-Cyano-pyrrolidin-1-yl)-2-oxo-ethylamino]-5-methyl-hexahydro-cyclopenta[c]pyrrole-2-carboxylic acid dimethylamide p-toluenesulfonate

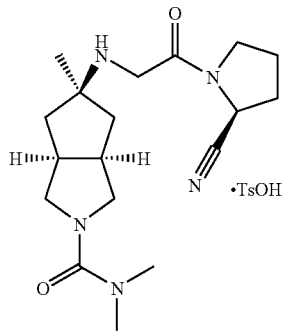

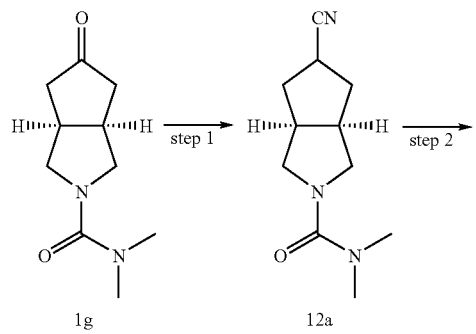
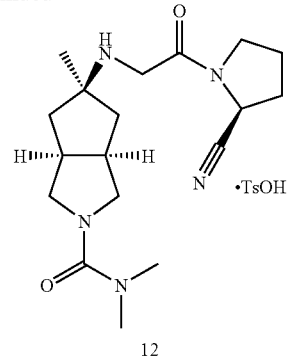

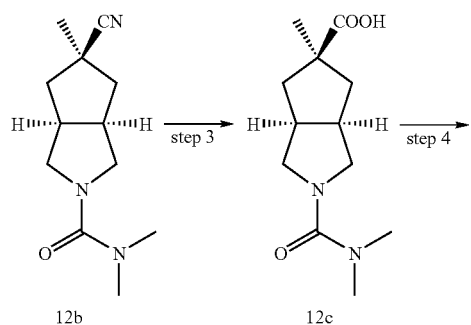

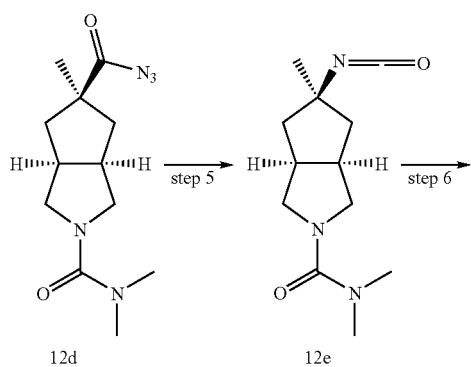

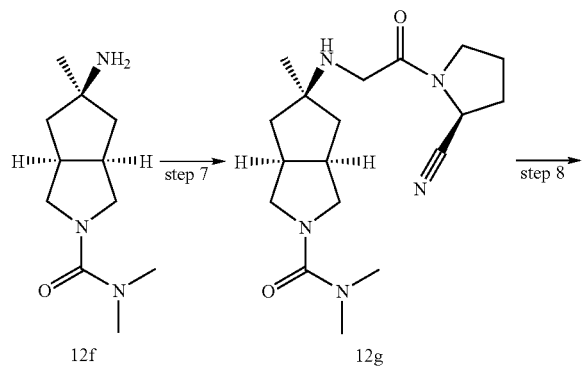

Step 1

Preparation of 5-cyano-hexahydro-cyclopenta[c]pyrrole-2-carboxylic acid dimethylamide N,N-dimethyl-5-oxo-hexahydro-cyclopenta[c]pyrrole-2-carboxamide 1g (12.9 g, 0.066 mol) and 4-toluenesulfonylmethyl isocyanide (14.2 g, 0.0727 mol) were dissolved in 240 mL of 1,2-dimethoxyethane with stirring upon cooling by an ice-water bath, followed by dropwise addition of a solution of potassium tert-butoxide (14.8 g, 0.132 mol) in tent-butanol. Upon completion of the addition, the ice-water bath was removed. The reaction mixture was warmed up to room temperature and reacted overnight. The reaction was monitored by TLC until the disappearance of the starting materials. The mixture was diluted with 100 mL of water and 50 mL of saturated brine and extracted with ethyl acetate (200 mL×3). The combined organic extracts were dried over anhydrous magnesium sulfate, filtered and concentrated under reduced pressure. The resulting residue was purified by silica gel column chromatography to obtain the title compound 5-cyano-hexahydro-cyclopenta[c]pyrrole-2-carboxylic acid dimethylamide 12a (7.0 g, yield 51%) as a light yellow oil.

MS m/z (ESI): 208.1 [M+1]

$^1$H NMR (DMSO-D$_6$, 400 MHz): δ 3.5-3.0 (m, 4H), 2.75 (s, 6H), 2.6 (m, 1H), 2.1-1.5 (m, 6H).

Step 2

5-Cyano-5-methyl-hexahydro-cyclopenta[c]pyrrole-2-carboxylic acid dimethylamide

5-Cyano-hexahydro-cyclopenta[c]pyrrole-2-carboxylic acid dimethylamide 12a (4.2 g, 20.2 mmol) and iodomethane (11.5 g, 80.8 mmol) were dissolved in 100 mL of tetrahydrofuran followed by dropwise addition of lithium hexamethyldisilazide (80.8 mL, 80.8 mmol) at room temperature under nitrogen atmosphere. The reaction mixture was reacted for 2 hours until MS showed the disappearance of the starting materials. The mixture was diluted with 100 mL of water and extracted with ethyl acetate (200 mL×3). The combined organic extracts were dried over anhydrous sodium sulfate, filtered and concentrated under reduced pressure to obtain an oil. TLC showed that there are two adjacent spots, and then the oil was purified by silica gel column chromatography to obtain the bottom spot compound 5-cyano-5-methyl-hexahydro-cyclopenta[c]pyrrole-2-carboxylic acid dimethylamide 12b (2.411 g) as a light yellow oil.

MS m/z (ESI): 222.2 [M+1]

¹H NMR (CDCl$_3$, 400 MHz): δ 3.44 (m, 2H), 3.3 (m, 2H), 2.85 (s, 6H), 2.77 (m, 2H), 2.06 (m, 2H), 2.00 (m, 2H), 1.36 (s, 3H).

Step 3

Preparation of 2-dimethylcarbamoyl-5-methyl-octahydro-cyclopenta[c]pyrrole-5-carboxylic acid 5-Cyano-5-methyl-hexahydro-cyclopenta[c]pyrrole-2-carboxylic acid dimethylamide 12b (6.99 g, 31.6 mmol) was dissolved in 90 mL of hydrochloric acid (36%). The reaction mixture was heated at 50° C. in an oil bath and stirred for 48 hours. The reaction was monitored by TLC until the disappearance of the starting materials. The reaction mixture was diluted with 100 mL of water. Upon cooling by an ice-water bath, the mixture was adjusted to pH 6 with potassium carbonate and extracted with ethyl acetate (1500 mL×3) and dichloromethane (150 mL×3) successively. The combined organic extracts were dried over anhydrous sodium sulfate, filtered and concentrated under reduced pressure to obtain the title compound 2-dimethylcarbamoyl-5-methyl-octahydro-cyclopenta[c]pyrrole-5-carboxylic acid 12c (7.0 g, yield 92%) as a yellow liquid, which was directly used in the next step.

MS m/z (ESI): 241.2 [M+1]

Step 4

Preparation of 2-dimethylcarbamoyl-5-methyl-hexahydro-cyclopenta[c]pyrrole-5-carbonylazide Upon cooling by an ice-water bath, 2-dimethylcarbamoyl-5-methyl-octahydro-cyclopenta[c]pyrrole-5-carboxylic acid 12c (1.0 g, 4.2 mmol) was dissolved in 25 mL of acetone with stirring, followed by dropwise addition of a solution of triethylamine (463.5 mg, 4.58 mmol) and ethyl chloroformate (497 mg, 4.58 mmol) in 10 mL of acetone at −5° C. The reaction mixture was reacted for 15 minutes at −5° C. followed by addition of a solution of sodium azide (546 mg, 8.4 mmol) in 10 mL of water. Then the reaction mixture was stirred for another 30 minutes at −5° C., and quenched with 25 mL of water and extracted with ethyl acetate (50 mL×3). The combined organic extracts were dried over anhydrous sodium sulfate, filtered and concentrated under reduced pressure to obtain the crude compound 2-dimethylcarbamoyl-5-methyl-hexahydro-cyclopenta[c]pyrrole-5-carbonylazide 12d (700 mg) as a yellow oil.

Step 5 to Step 6

2-Dimethylcarbamoyl-5-methyl-hexahydro-cyclopenta[c]pyrrole-5-carbonylazide 12d (700 mg) was added to 20 mL of toluene and the reaction mixture was heated to reflux for 2 hours. The toluene was evaporated resulting in the formation of (3aS,5r,6aR)-5-isocyanato-5-methyl-N,N,5-trimethyl-hexahydro-cyclopenta[c]pyrrole-2(1H)-2-carboxamide 12e. Upon cooling by an ice-water bath, to a solution of 8 mL of hydrochloric acid (8 N) was added the above mentioned mixture. The reaction mixture was stirred for 30 minutes and the reaction was monitored by TLC until the disappearance of the starting materials. Upon cooling by an ice-water bath, the mixture was adjusted to pH>12 with a 3 N aqueous sodium hydroxide solution and extracted with ethyl acetate (15 mL×3). The combined organic extracts were dried over anhydrous magnesium sulfate, filtered and concentrated under reduced pressure. The residue was purified by silica gel column chromatography to obtain the title compound 5-amino-5-methyl-hexahydro-cyclopenta[c]pyrrole-2-carboxylic acid dimethylamide 12f (500 mg) as a light yellow oil.

MS m/z (ESI): 212.2 [M+1]

¹H NMR (DMSO-D$_6$, 400 MHz): δ 3.5-3.0 (m, 4H), 2.72 (s, 6H), 1.7-1.3 (m, 6H), 1.04 (s, 3H).

Step 7

Preparation of 5-[2-((S)-2-cyano-pyrrolidin-1-yl)-2-oxo-ethylamino]-5-methyl-hexahydro-cyclopenta[c]pyrrole-2-carboxylic acid dimethylamide 5-Amino-5-methyl-hexahydro-cyclopenta[c]pyrrole-2-carboxylic acid dimethylamide 12f (332 mg, 1.57 mmol) was dissolved in 10 mL of a solvent mixture of N,N-dimethylformamide/dichloromethane (1:1) followed by addition of 1-(2-chloro-acetyl)-pyrrolidine-2-cyano (217 mg, 1.26 mmol). The reaction mixture was reacted overnight at room temperature and concentrated under reduced pressure. The resulting residue was purified by silica gel column chromatography to obtain the title compound 5-[2-((S)-2-cyano-pyrrolidin-1-yl)-2-oxo-ethylamino]-5-methyl-hexahydro-cyclopenta[c]pyrrole-2-carboxylic acid dimethylamide 12g (240 mg, yield 55%) as a colorless oil.

MS m/z (ESI): 348.2 [M+1]

Step 8

Preparation of 5-[2-((S)-2-cyano-pyrrolidin-1-yl)-2-oxo-ethylamino]-5-methyl-hexahydro-cyclopenta[c]pyrrole-2-carboxylic acid dimethylamide p-toluenesulfonate 5-[2-(2-Cyano-pyrrolidin-1-yl)-2-oxo-ethylamino]-5-methyl-hexahydro-cyclopnta[c]pyrrole-2-carboxylic acid dimethylamide 12g (150 mg, 0.43 mmol) and p-toluenesulfonic acid monohydrate (82 mg, 0.43 mmol) were dissolved in 4 mL of dichloromethane with stirring. The reaction mixture was stirred for 10 minutes and concentrated under reduced pressure to obtain the title compound 5-[2-((S)-2-cyano-pyrrolidin-1-yl)-2-oxo-ethylamino]-5-methyl-hexahydro-cyclopenta[c]pyrrole-2-carboxylic acid dimethylamide p-toluenesulfonate 12 (0.022 g, yield 95.3%) as a light yellow solid.

MS m/z (ESI): 348.2 [M+1]

¹H NMR (DMSO-D$_6$, 400 MHz): δ 4.82 (m, 1H), 3.97 (s, 2H), 3.79 (m, 2H), 3.49 (m, 2H), 3.21 (m, 4H), 2.75 (s, 6H), 2.62 (m, 2H), 2.19 (m, 2H), 1.92-1.61 (m, 3H), 2.06 (m, 3H), 1.2 (s, 3H).

Example 13

5-[2-((2S,4S)-2-Cyano-4-fluoro-pyrrolidin-1-yl)-2-oxo-ethylamino]-N,N,5-trimethyl-hexahydro-cyclopenta[c]pyrrole-2-carboxamide tartrate

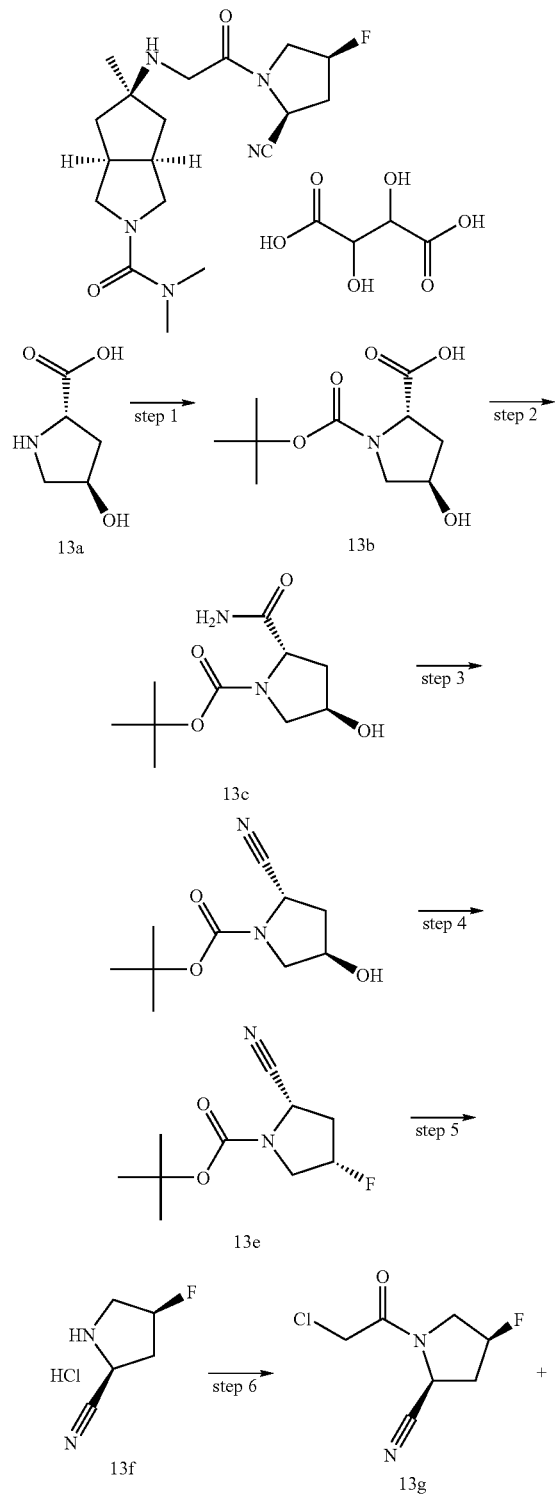

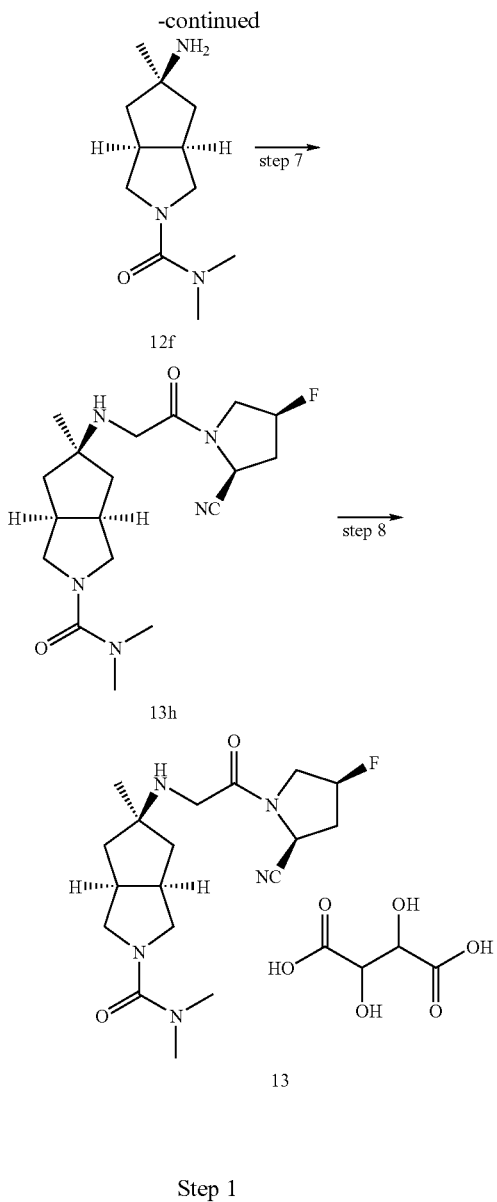

Step 1

Preparation of (2S,4R)-1-(tert-butoxycarbonyl)-4-hydroxypyrrolidine-2-carboxylic acid L-Hydroxyproline 13a (60 g, 0.458 mol) was added to a solution of 750 mL of solvent mixture of tetrahydrofuran/water (2:1) followed by 252 mL of aqueous sodium hydroxide (10%) and a solution of di-tent-butyl dicarbonate (136 g, 0.624 mol) in 750 mL of solvent mixture of tetrahydrofuran/water (2:1). The reaction mixture was reacted overnight at room temperature and diluted with 500 mL of ethyl acetate. The layers were separated and then the organic layer was discarded, and the aqueous layer was adjusted to pH 2 with concentrated hydrochloric acid. The mixture was extracted with 1.5 L of ethyl acetate. The combined organic extracts were washed with saturated brine, dried over anhydrous sodium sulfate, filtered and concentrated under reduced pressure to obtain the title compound (2S,4R)-1-(tert-butoxycarbonyl)-4-hydroxypyrrolidine-2-carboxylic acid 13b (86.4 g, yield 80%) as a colorless oil.

Step 2

Preparation of (2S,4R)-tert-butyl
2-carbamoyl-4-hydroxypyrrolidine-1-carboxylate (2S,4R)-1-(tert-Butoxycarbonyl)-4-hydroxypyrrolidine-2-carboxylic acid 13b (86.4 g, 0.374 mol) was dissolved in 1.2 L of tetrahydrofuran followed by addition of triethylamine (41 g, 0.411 mol) under argon atmosphere. The reaction mixture was cooled to −15° C., ethyl chlorformate (43.84 g, 0.411 mol) was added. After the mixture was stirred for 10 minutes, aqueous ammonia (236.8 mL) was added. The reaction mixture was slowly warmed up to 5° C. during 2 hours followed by addition of ammonium chloride (32 g). The reaction mixture was stirred for 30 minutes and separated. The separated organic phase was dried over anhydrous sodium sulfate, and the aqueous phase was extracted with ethyl acetate (100 mL×2). The combined organic extracts were concentrated under reduced pressure to obtain the title compound (2S,4R)-tert-butyl 2-carbamoyl-4-hydroxypyrrolidine-1-carboxylate 13c (74 g, yield 86%) as a white solid.

Step 3

Preparation of (2S,4R)-tert-butyl
2-cyano-4-hydroxypyrrolidine-1-carboxylate (2S,4R)-tert-Butyl 2-carbamoyl-4-hydroxypyrrolidine-1-carboxylate 13c (74 g, 0.3217 mol) was dissolved in 740 mL of pyridine with stirring under argon atmosphere. The mixture was cooled to −20° C. followed by dropwise addition of trifluoroacetic anhydride (169 g, 0.804 mol). Upon completion of the addition, the reaction mixture was warmed up to room temperature. The reaction was monitored by TLC until the disappearance of the starting materials. The mixture was quenched with water and diluted with 0.8 L of ethyl acetate. The separated organic phase was washed with 500 mL of saturated brine and neutralized with 400 mL of concentrated hydrochloric acid to slight acidity. The resulting mixture was washed with 300 mL of aqueous sodium hydroxide solution (2 M) and 500 mL saturated brine successively, dried over anhydrous sodium sulfate, filtered and concentrated under reduced pressure to obtain the title compound (2S,4R)-tert-butyl 2-cyano-4-hydroxypyrrolidine-1-carboxylate 13d (49.7 g, yield 73%) as a brown oil.

Step 4

Preparation of (2S,4S)-tert-butyl
2-cyano-4-fluoropyrrolidine-1-carboxylate (2S,4R)-tert-Butyl 2-cyano-4-hydroxypyrrolidine-1-carboxylate 13d (49.7 g, 0.2344 mol) was dissolved in 1130 mL of dichloromethane with stirring under argon atmosphere. The mixture was cooled to −30° C. followed by addition of diethylaminosulfur trifluoride (56.7 g, 0.3516 mol). After stirred for 45 minutes, the reaction mixture was warmed up to −5° C. Then the mixture was reacted overnight at room temperature. The reaction was monitored by TLC until the disappearance of the starting materials. The reaction mixture was neutralized with saturated aqueous sodium carbonate solution to pH >7 at such a rate that the reaction temperature was kept below 20° C. Then ice water and 500 mL of dichloromethane were added. The separated organic phase was washed with 500 mL of saturated aqueous sodium hydrogen sulfate and 500 mL of saturated brine successively, dried over anhydrous sodium sulfate, filtered and concentrated under reduced pressure in which the concentration temperature was kept below 38° C. to obtain the title compound (2S,4S)-tent-butyl 2-cyano-4-fluoropyrrolidine-1-carboxylate 13e (50 g, yield 100%) as a light yellow solid.

Step 5

Preparation of
(2S,4S)-4-fluoropyrrolidine-2-carbonitrile (2S,4S)-tert-Butyl 2-cyano-4-fluoropyrrolidine-1-carboxylate 13e (1 g, 4.6 mmol) was dissolved in 2 mL of ethyl acetate with stirring under argon atmosphere. The mixture was cooled to 15° C. followed by addition of a solution of hydrogen chloride in 2.5 mL of 1,4-dioxane (3 M). The reaction mixture was stirred at room temperature for 2 hours. Then the mixture was reacted for another 5 hours at 25° C. The reaction was monitored by TLC, which indicated the presence of the starting materials. The reaction mixture was filtered and the filtrate was stirred at room temperature for 2 hours resulting in the formation of a white precipitate. The mixture was filtered again and the filtrate was stirred for another 2 hours, then filtered. The filter cakes were combined to obtain the title compound (2S,4S)-4-fluoropyrrolidine-2-carbonitrile 13f (15.6 g, yield 76.6%) as a white solid.

Step 6

Preparation of (2S,4S)-1-(2-chloroacetyl)-4-fluoro-pyrrolidine-2-carbonitrile

Chloroacetyl chloride (11.13 g, 98.5 mmol) was dissolved in 120 mL of dichloromethane with stirring under argon atmosphere. Upon cooling to 0° C., (2S,4S)-4-fluoropyrrolidine-2-carbonitrile 13f (11.4 g, 75.7 mmol) was dissolved in 400 mL of dichloromethane followed by addition of triethylamine (16.1 g, 158.97 mmol). To a solution of chloroacetyl chloride in dichloromethane was added the above mentioned mixture in 30 minutes. The reaction mixture was reacted at 0° C. for 2 hours and diluted with 200 mL of ice water and 150 mL of dichloromethane. The separated organic phase was neutralized with saturated sodium bisulfate, washed with 300 mL of water and 300 mL of saturated brine successively, dried over anhydrous sodium sulfate, filtered and concentrated under reduced pressure. The resulting residue was purified by silica gel column chromatography to obtain the title compound (2S,4S)-1-(2-chloroacetyl)-4-fluoropyrrolidine-2-carbonitrile 13g (8 g, yield 60%) as a white crystal.

Reference: WO2003002553.

Step 7

Preparation of 5-[2-((2S,4S)-2-cyano-4-fluoro-pyrrolidin-1-yl)-2-oxo-ethylamino]-N,N,5-trimethyl-hexahydro-cyclopenta[c]pyrrole-2(1H)-carboxamide 5-Amino-5-methyl-hexahydro-cyclopenta[c]pyrrole-2-carboxylic acid dimethylamide 12f (130 mg, 0.616 mmol), (2S,4S)-1-(2-chloroacetyl)-4-fluoropyrrolidine-2-carbonitrile 13g (117.4 mg, 0.616 mmol) and potassium carbonate (85 mg, 0.616 mmol) were dissolved in the solvent mixture of 2 mL of dichloromethane and 2 mL of N,N-dimethylformamide with stirring under nitrogen atmosphere. The reaction mixture was reacted overnight at room temperature. The reaction was monitored by TLC until the disappearance of the starting materials. The mixture was concentrated under reduced pressure to remove N,N-dimethylformamide and dichloromethane. The resulting residue was purified by silica gel column chromatography to obtain 5-[2-((2S,4S)-2-cyano-4-fluoro-pyrrolidin-1-yl)-2-oxo-ethylamino]-N,N,5-trimethyl-hexahydro-cyclopenta[c]pyrrole-2(1H)-carboxamide 13h (0.13 g, yield 58%) as a colorless oil.

Step 8

Preparation of 5-[2-((2S,4S)-2-cyano-4-fluoro-pyrrolidin-1-yl)-2-oxo-ethylamino]-N,N,5-trimethyl-hexahydro-cyclopenta[c]pyrrole-2-carboxamide tartrate 5-[2-((2S,4S)-2-Cyano-4-fluoro-pyrrolidin-1-yl)-2-oxo-ethylamino]-N,N,5-trimethyl-hexahydro-cyclopenta[c]pyrrole-2(1H)-2-carboxamide 13h (0.16 g, 0.44 mmol) was dissolved in 5 mL of dichloromethane with stirring followed by dropwise addition of a solution of 5 mL of tartaric acid (65.6 mg, 0.44 mmol) in acetone. The reaction mixture was reacted for 30 minutes resulting in the formation of a white precipitate. The mixture was filtered and the filter cake was washed with acetone to obtain the title compound 5-[2-((2S,4S)-2-cyano-4-fluoro-pyrrolidin-1-yl)-2-oxo-ethylamino]-N,N,5-trimethyl-hexahydro-cyclopenta[c]pyrrole-2-carboxamide tartrate 13 (0.18 g, yield 82%) as a white solid.

$^1$H NMR (DMSO-D$_6$, 400 MHz): δ 5.76 (m, 1H), 5.46 (m, 1H), 5.0 (m, 1H), 4.08-4.05 (m, 4H), 3.97 (m, 2H), 3.69 (m, 2H), 2.73 (s, 6H), 2.61 (m, 2H), 1.87 (m, 3H), 1.57 (m, 3H), 1.18 (s, 3H), 1.9 (m, 2H).

Example 14

5-Benzyl-5-[2-((2S,4S)-2-cyano-4-fluoro-pyrrolidin-1-yl)-2-oxo-ethylamino]-hexahydro-cyclopenta[c]pyrrole-2-carboxylic acid dimethylamide tartrate

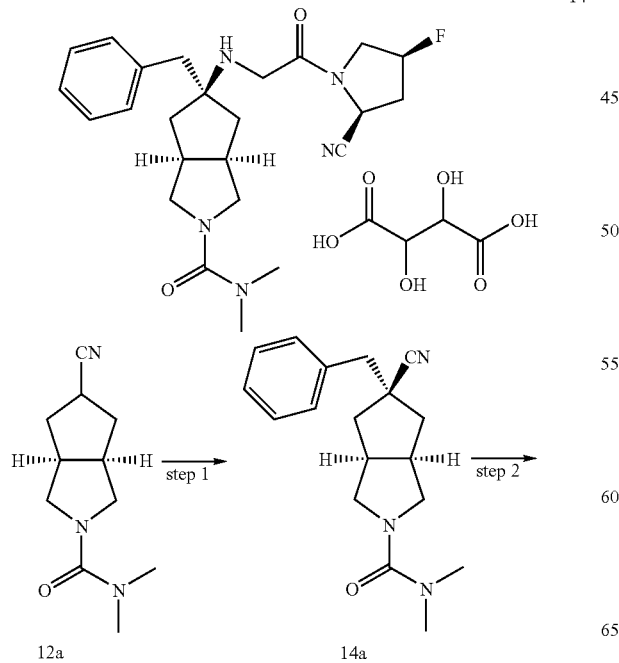

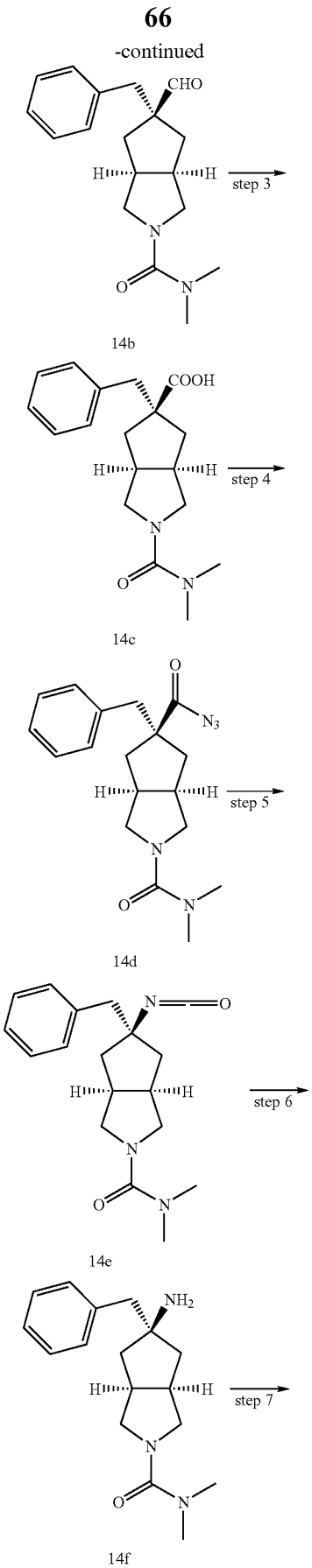

-continued

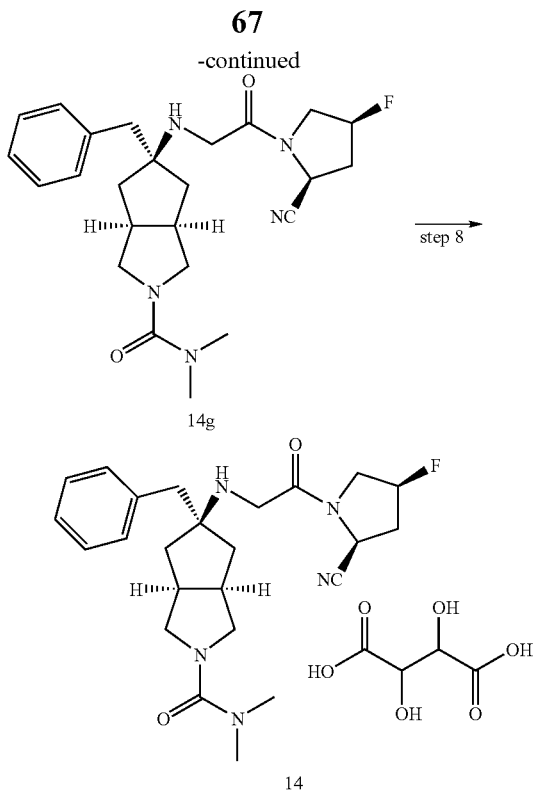

Step 1

Preparation of 5-benzyl-5-cyano-hexahydro-cyclopenta[c]pyrrole-2-carboxylic acid dimethylamide 5-Cyano-hexahydro-cyclopenta[c]pyrrole-2-carboxylic acid dimethylamide 12a (4.0 g, 19.3 mmol) was dissolved in 60 mL of tetrahydrofuran with stirring followed by addition of benzyl chloride (5.4 g, 42.5 mmol) and lithium hexamethyldisilazide (42.5 mL, 42.5 mmol) under nitrogen atmosphere. The reaction mixture was stirred at room temperature for 4 hours. The reaction was monitored by TLC until the disappearance of the starting materials and quenched with 50 mL of water. The mixture was extracted with ethyl acetate. The combined organic extracts were dried over anhydrous sodium sulfate, filtered and concentrated under reduced pressure. The resulting residue was purified by silica gel column chromatography to obtain the title compound 5-benzyl-5-cyano-hexahydro-cyclopenta[c]pyrrole-2-carboxylic acid dimethylamide 14a (2.6 g, yield 46%) as a light yellow solid.

Step 2

Preparation of 5-benzyl-5-formyl-hexahydro-cyclopenta[c]pyrrole-2-carboxylic acid dimethylamide 5-Benzyl-5-cyano-hexahydro-cyclopenta[c]pyrrole-2-carboxylic acid dimethylamide 14a (2.0 g, 6.7 mmol) was dissolved in 100 mL of dichloromethane with stirring. Upon cooling to 0° C., diisobutylaluminium hydride (20.2 mL, 20.2 mmol) was added dropwise. The reaction was monitored by TLC until the disappearance of the starting materials and quenched with water. The mixture was extracted with ethyl acetate. The combined organic extracts were dried over anhydrous sodium sulfate, filtered and concentrated under reduced pressure. The resulting residue was purified by silica gel column chromatography to obtain the title compound 5-benzyl-5-formyl-hexahydro-cyclopenta[c]pyrrole-2-carboxylic acid dimethylamide 14b (729 mg, yield 36%) as a colorless oil.

Step 3

Preparation of 5-benzyl-2-dimethylcarbamoyl-octahydro-cyclopenta[c]pyrrole-5-carboxylic acid 5-Benzyl-5-formyl-hexahydro-cyclopenta[c]pyrrole-2-carboxylic acid dimethylamide 14b (0.729 g, 2.43 mmol) was dissolved in the solvent mixture of 28 mL of tetrahydrofuran and 14 mL of water under nitrogen atmosphere, followed by addition of sodium dihydrogenphosphate dihydrate (1.14 g, 7.29 mmol), sodium chlorite (0.66 g, 7.29 mmol) and 2-methyl-2-butene (0.513 g, 7.32 mmol) upon cooling to 0° C. The reaction mixture was stirred at 0° C. for 2 hours. The reaction was monitored by TLC until the disappearance of the starting materials. The mixture was extracted with ethyl acetate. The combined organic extracts were dried over anhydrous magnesium sulfate, filtered and concentrated under reduced pressure. The resulting residue was purified by silica gel column chromatography to obtain the title compound 5-benzyl-2-dimethylcarbamoyl-octahydro-cyclopenta[c]pyrrole-5-carboxylic acid 14c (0.76 g, yield 98%) as a colorless oil.

MS m/z (ESI): 317.3 [M+1]

$^1$H NMR (DMSO-$D_6$, 400 MHz): δ 7.5-7.0 (m, 5H), 3.24 (m, 2H), 3.1 (m, 2H), 2.76 (s, 2H), 2.7 (s, 6H), 2.68 (m, 2H), 1.99-1.55 (m, 4H).

Step 4

Preparation of 5-benzyl-2-dimethylcarbamoyl-octahydro-cyclopenta[c]pyrrole-5-carbonyl azide 5-Benzyl-2-dimethylcarbamoyl-octahydro-cyclopenta[c]pyrrole-5-carboxylic acid 14c (0.86 g, 2.72 mmol) was dissolved in 30 mL of acetone upon cooling by an ice-water bath. When the mixture was cooled to −5° C., a solution of triethylamine (0.303 g, 2.99 mmol) and ethyl chloroformate (0.325 g, 2.99 mmol) in 15 mL of acetone were added dropwise successively. The reaction mixture was stirred for 15 minutes followed by dropwise addition of a solution of sodium azide (0.353 g, 5.44 mmol) in 15 mL of water. The reaction mixture was stirred for another 30 minutes. The reaction was monitored by TLC until the disappearance of the starting materials. The mixture was concentrated under reduced pressure and extracted with ethyl acetate. The combined organic extracts were dried over anhydrous sodium sulfate, filtered and concentrated under reduced pressure to obtain the title compound 5-benzyl-2-dimethylcarbamoyl-octahydro-cyclopenta[c]pyrrole-5-carbonyl azide 14d (0.9 g, yield 97%) as a light yellow oil.

Step 5

Preparation of 5-benzyl-5-isocyanato-hexahydro-cyclopenta[c]pyrrole-2-carboxylic acid dimethylamide 5-Benzyl-2-dimethylcarbamoyl-octahydro-cyclopenta[c]pyrrole-5-carbonyl azide 14d (1.0 g, 2.72 mmol) was dissolved in 20 mL of toluene with stirring. The reaction mixture was heated to reflux for 1.5 hours and the solvent was evaporated to obtain the crude title compound 5-benzyl-5-isocyanato-hexahydro-cyclopenta[c]pyrrole-2-carboxylic acid dimethylamide 14e which was directly used in the next step.

Step 6

Preparation of 5-amino-5-benzyl-hexahydro-cyclopenta[c]pyrrole-2-carboxylic acid dimethylamide To a solution of 12 mL hydrochloric acid (8 N) was added dropwise 5-benzyl-5-isocyanato-hexahydro-cyclopenta[c]pyrrole-2-carboxylic acid dimethylamide 14e obtained from the above step at room temperature. The reaction mixture was stirred for 30 minutes and adjusted to pH 9 with a 4 N sodium hydroxide aqueous solution. The mixture was extracted with ethyl acetate. The combined organic extracts were dried over anhydrous sodium sulfate, filtered and concentrated under reduced pressure. The resulting residue was purified by silica gel column chromatography to obtain the title compound 5-amino-5-benzyl-hexahydro-cyclopenta[c]pyrrole-2-carboxylic acid dimethylamide 14f (0.55 g, yield 70%) as a colorless oil.

Step 7

Preparation of 5-benzyl-5-[2-((2S,4S)-2-cyano-4-fluoro-pyrrolidin-1-yl)-2-oxo-ethylamino]-hexahydro-cyclopenta[c]pyrrole-2-carboxylic acid dimethylamide 5-Amino-5-benzyl-hexahydro-cyclopenta[c]pyrrole-2-carboxylic acid dimethylamide 14f (0.1 g, 0.35 mmol) was dissolved in 4 mL of the solvent mixture of dichloromethane/N,N-dimethylformamide (V/V=1/1) followed by addition of (2S,4S)-1-(2-chloroacetyl)-4-fluoropyrrolidine-2-carbonitrile 13g (66.5 mg, 0.35 mmol) and potassium carbonate (49 mg, 0.35 mmol). The reaction mixture was reacted at 40° C. for 12 hours. The reaction was monitored by TLC until the disappearance of the starting materials. The mixture was concentrated, and the resulting residue was purified by silica gel column chromatography to obtain the title compound 5-benzyl-5-[2-((2S,4S)-2-cyano-4-fluoro-pyrrolidin-1-yl)-2-oxo-ethylamino]-hexahydro-cyclopenta[c]pyrrole-2-carboxylic acid dimethylamide 14g (87 mg, yield 56%) as a white solid.

MS m/z (ESI): 442.2 [M+1]

Step 8

Preparation of 5-benzyl-5-[2-((2S,4S)-2-cyano-4-fluoro-pyrrolidin-1-yl)-2-oxo-ethylamino]-hexahydro-cyclopenta[c]pyrrole-2-carboxylic acid dimethylamide tartrate 5-Benzyl-5-[2-((2S,4S)-2-cyano-4-fluoro-pyrrolidin-1-yl)-2-oxo-ethylamino]-hexahydro-cyclopenta[c]pyrrole-2-carboxylic acid dimethylamide 14g (87 mg, 0.197 mmol) was dissolved in 3 mL of dichloromethane with stirring followed by dropwise addition of a solution of 3 mL of tartaric acid in acetone. The reaction mixture was reacted at room temperature for 30 minutes and concentrated. The resulting residue was recrystallized from a solvent mixture of ethyl acetate/acetone to obtain the title compound 5-benzyl-5-[2-((2S,4S)-2-cyano-4-fluoro-pyrrolidin-1-yl)-2-oxo-ethylamino]-hexahydro-cyclopenta[c]pyrrole-2-carboxylic acid dimethylamide tartrate 14 (80 mg, yield 68%) as a white solid.

$^1$H NMR (DMSO-D$_6$, 400 MHz): δ 7.32-7.2 (m, 5H), 5.55 (d, 1H), 5.41 (d, 1H), 4.97 (m, 1H), 4.31 (s, 2H), 4.08 (m, 1H), 4.0-3.5 (m, 6H), 2.81 (s, 2H), 2.78 (s, 6H), 2.5 (m, 2H), 2.0 (m, 3H), 1.6-1.3 (m, 6H).

Example 15

5-Cyclohexylmethyl-5-[2-((S)-2-cyano-pyrrolidin-1-yl)-2-oxo-ethylamino]-hexahydro-cyclopenta[c]pyrrole-2-carboxylic acid dimethylamide tartrate

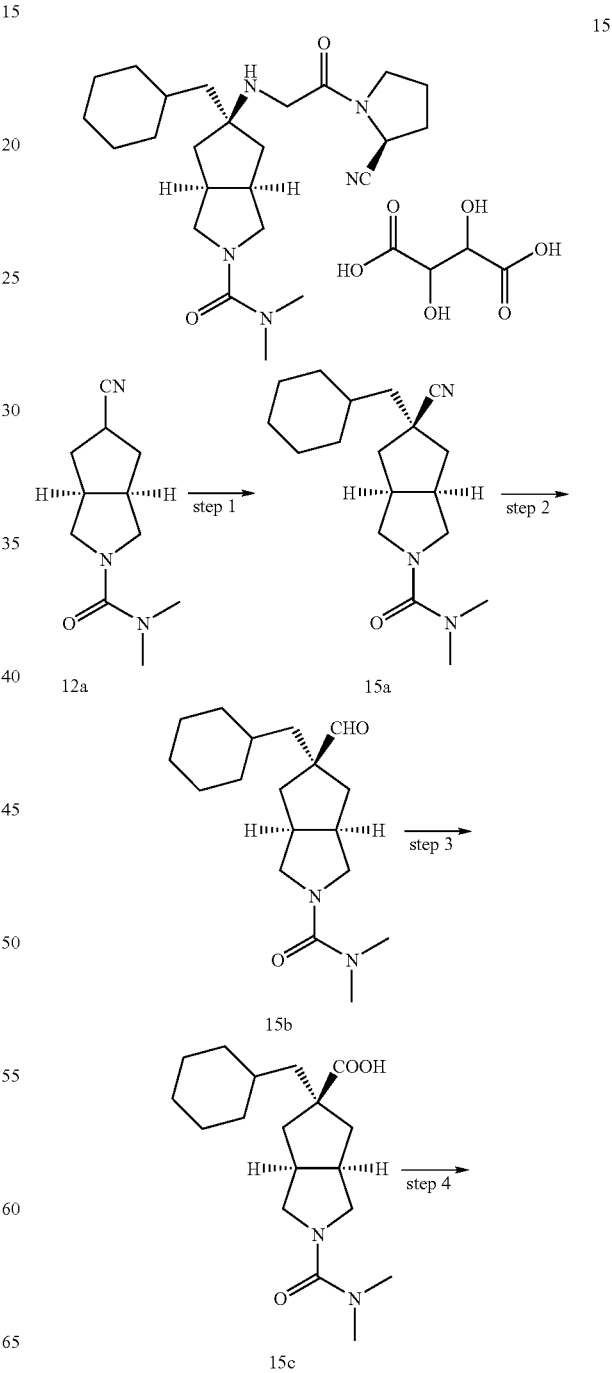

-continued

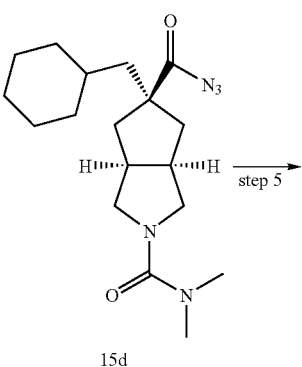
15d

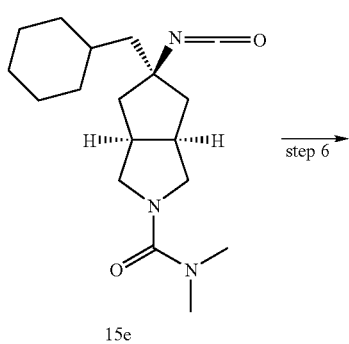
15e

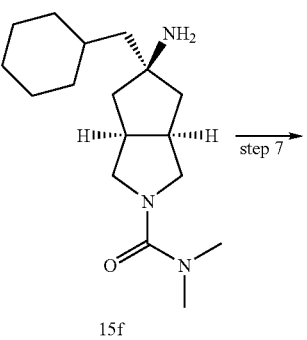
15f

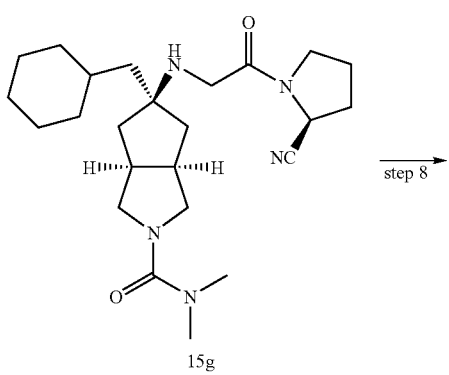
15g

-continued

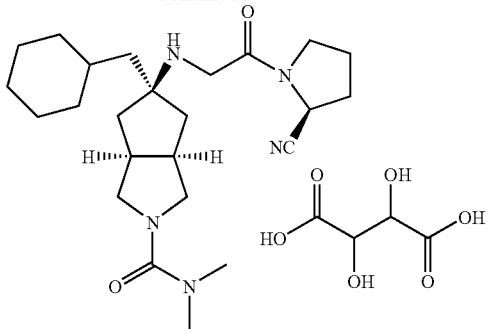
15

Step 1

Preparation of 5-cyano-5-cyclohexylmethyl-hexahydro-cyclopenta[c]pyrrole-2-carboxylic acid dimethylamide 5-Cyano-hexahydro-cyclopenta[c]pyrrole-2-carboxylic acid dimethylamide 12a (3.66 g, 17.6 mmol) was dissolved in 150 mL of tetrahydrofuran with stirring followed by dropwise addition of cyclohexylmethyl bromide (6.2 g, 35.2 mmol) and lithium hexamethyldisilazide (35.2 mL, 32.5 mmol). The reaction mixture was reacted at room temperature for 2 hours. The reaction was monitored by TLC until the disappearance of the starting materials. Then 150 mL of a saturated aqueous solution of ammonium chloride was added. The mixture was extracted with ethyl acetate (60 mL×3). The combined organic extracts were dried over anhydrous magnesium sulfate, filtered and concentrated under reduced pressure. The resulting residue was purified by silica gel column chromatography to obtain the title compound 5-cyano-5-cyclohexylmethyl-hexahydro-cyclopenta[c]pyrrole-2-carboxylic acid dimethylamide 15a (2.2 g, yield 41.5%) as a yellow solid.

MS m/z (ESI): 304.5 [M+1]

Step 2

Preparation of 5-cyclohexylmethyl-5-formyl-hexahydro-cyclopenta[c]pyrrole-2-carboxylic acid dimethylamide Upon cooling to 0° C. by an ice-water bath, 5-cyano-5-cyclohexylmethyl-hexahydro-cyclopenta[c]pyrrole-2-carboxylic acid dimethylamide 15a (1.2 g, 3.95 mmol) was dissolved in 30 mL of dichloromethane with stirring followed by dropwise addition of diisobutylaluminium hydride (11.8 mL, 11.8 mmol). The reaction mixture was reacted for 1 hour. The reaction was monitored by TLC until the disappearance of the starting materials. Then a solution of saturated aqueous potassium sodium tartrate was added. The mixture was stirred until the solution was clear and extracted with ethyl acetate (100 mL×3). The combined organic extracts were dried over anhydrous magnesium sulfate, filtered and concentrated under reduced pressure. The resulting residue was purified by silica gel column chromatography to obtain the title compound 5-cyclohexylmethyl-5-formyl-hexahydro-cyclopenta[c]pyrrole-2-carboxylic acid dimethylamide 15b (0.4 g, yield 33%) as a light yellow oil.

MS m/z (ESI): 307.4 [M+1]

Step 3

Preparation of 5-cyclohexylmethyl-2-dimethylcarbamoyl-octahydro-cyclopenta[c]pyrrole-5-carboxylic acid 5-Cyclohexylmethyl-5-formyl-hexahydro-cyclopenta[c]pyrrole-2-carboxylic acid dimethylamide 15b (0.713 g, 2.33 mmol) was dissolved in the solvent mixture of 60 mL of tetrahydrofuran and 30 mL of water. Upon cooling to 0° C., sodium dihydrogenphosphate dihydrate (1.09 g, 6.99 mmol), sodium chlorite (0.79 g, 6.99 mmol) and 2-methyl-2-butene (0.62 mL, 7.0 mmol) were added. The reaction mixture was reacted at 0° C. for 2 hours. The reaction was monitored by TLC until the disappearance of the starting materials. The mixture was concentrated to remove tetrahydrofuran and extracted with ethyl acetate. The combined organic extracts were dried over anhydrous magnesium sulfate, filtered and concentrated under reduced pressure. The resulting residue was purified by silica gel column chromatography to obtain the title compound 5-cyclohexylmethyl-2-dimethylcarbamoyl-octahydro-cyclopenta[c]pyrrole-5-carboxylic acid 15c (0.75 g, yield 100%) as a yellow solid.

MS m/z (ESI): 323.3 [M+1]

Step 4

Preparation of 5-cyclohexylmethyl-2-dimethylcarbamoyl-octahydro-cyclopenta[c]pyrrole-5-carbonyl azide Upon cooling by an ice-water bath, 5-cyclohexylmethyl-2-dimethylcarbamoyl-octahydro-cyclopenta[c]pyrrole-5-carboxylic acid 15c (0.75 g, 2.33 mmol) was dissolved in 20 mL of acetone with stirring followed by dropwise addition of triethylamine (0.36 mL, 2.56 mmol) and a solution of 2 mL of ethyl chloroformate (0.25 mL, 2.56 mmol) in acetone. The reaction mixture was stirred for 15 minutes and a solution of 2 mL of sodium azide (0.303 g, 4.66 mmol) in water was added. The reaction mixture was reacted for another 30 minutes at 0° C.~5° C. The reaction was monitored by TLC until the disappearance of the starting materials. The mixture was concentrated to remove acetone and diluted with 10 mL of water. The mixture was extracted with ethyl acetate (10 mL×5). The combined organic extracts were dried over anhydrous magnesium sulfate, filtered and concentrated under reduced pressure to obtain the title compound 5-cyclohexylmethyl-2-dimethylcarbamoyl-octahydro-cyclopenta[c]pyrrole-5-carbonyl azide 15d (0.79 g) as a yellow oil which was directly used in the next step.

Step 5

Preparation of 5-cyclohexylmethyl-5-isocyanato-hexahydro-cyclopenta[c]pyrrole-2-carboxylic acid dimethylamide 5-Cyclohexylmethyl-2-dimethylcarbamoyl-octahydro-cyclopenta[c]pyrrole-5-carbonyl azide 15d (0.79 g, 2.27 mmol) was dissolved in 20 mL of toluene and the reaction mixture was heated to reflux for 1 hour. The reaction was monitored by TLC until the disappearance of the starting materials. The mixture was concentrated to obtain the title compound 5-cyclohexylmethyl-5-isocyanato-hexahydro-cyclopenta[c]pyrrole-2-carboxylic acid dimethylamide 15e (0.65 g) as a grey solid, which was directly used in the next step.

MS m/z (ESI): 320.4 [M+1]

Step 6

Preparation of 5-amino-5-cyclohexylmethyl-hexahydro-cyclopenta[c]pyrrole-2-carboxylic acid dimethylamide Upon cooling by an ice-water bath, to a solution of 10 mL of hydrochloric acid (8 N) was added dropwise 5-cyclohexylmethyl-5-isocyanato-hexahydro-cyclopenta[c]pyrrole-2-carboxylic acid dimethylamide 15e (0.65 g, 2.03 mmol). Then the ice-water bath was removed. The reaction mixture was reacted at 50° C. for 20 minutes. The reaction was monitored by TLC until the disappearance of the starting materials. The mixture was adjusted to pH>8 with concentrated ammonia and extracted with ethyl acetate (30 mL×5). The combined organic extracts were dried over anhydrous magnesium sulfate, filtered and concentrated under reduced pressure. The resulting residue was purified by silica gel column chromatography to obtain 5-amino-5-cyclohexylmethyl-hexahydro-cyclopenta[c]pyrrole-2-carboxylic acid dimethylamide 15f (0.5 g, yield 84%) as a grey oil.

MS m/z (ESI): 294.3 [M+1]

Step 7

Preparation of 5-(cyclohexylmethyl)-5-[2-((S)-2-cyano-pyrrolidin-1-yl)-2-oxo-ethylamino]-5-cyclohexylmethyl-hexahydro-cyclopenta[c]pyrrole-2-carboxylic acid dimethylamide 5-Amino-5-cyclohexylmethyl-hexahydro-cyclopenta[c]pyrrole-2-carboxylic acid dimethylamide 15f (0.115 g, 0.39 mmol) was dissolved in 10 mL of a solvent mixture dichloromethane/N,N-dimethylformamide (V/V=1/1) with stirring, followed by addition of 1-(2-chloro-acetyl)-pyrrolidine-2-cyano (54 mg, 0.31 mmol). The reaction mixture was reacted at 50° C. for 2 hours. The reaction was monitored by TLC until the disappearance of the starting materials. The mixture was concentrated under reduced pressure to remove dichloromethane and N,N-dimethylformamide. The resulting residue was purified by silica gel column chromatography to obtain the title compound 5-(cyclohexylmethyl)-5-[2-((S)-2-cyano-pyrrolidin-1-yl)-2-oxo-ethylamino]-5-cyclohexylmethyl-hexahydro-cyclopenta[c]pyrrole-2-carboxylic acid dimethylamide 15 g (113 mg, yield 67%) as a colorless oil.

MS m/z (ESI): 430.5 [M+1].

Step 8

Preparation of 5-(cyclohexylmethyl)-5-[2-((S)-2-cyano-pyrrolidin-1-yl)-2-oxo-ethylamino]-hexahydro-cyclopenta[c]pyrrole-2-carboxylic acid dimethylamide tartrate 5-(Cyclohexylmethyl)-5-[2-((S)-2-Cyano-pyrrolidin-1-yl)-2-oxo-ethylamino]-5-cyclohexylmethyl-hexahydro-cyclopenta[c]pyrrole-2-carboxylic acid dimethylamide 15g (113 mg, 0.263 mmol) was dissolved in 10 mL of ethyl acetate followed by dropwise addition of a solution of 2 mL of tartaric acid in acetone. The reaction mixture was stirred for 30 minutes and filtered to obtain the title compound 5-(cyclohexylmethyl)-5-[2-((S)-2-cyano-pyrrolidin-1-yl)-2-oxo-ethylamino]-hexahydro-cyclopenta[c]pyrrole-2-carboxylic acid dimethylamide tartrate 15 (40 mg) as a white solid.

¹H NMR (DMSO-D₆, 400 MHz): δ 5.2 (m, 1H), 4.77 (s, 2H), 4.18 (m, 3H), 4.02 (m, 1H), 3.63 (m, 2H), 3.32 (m, 2H), 2.73 (s, 6H), 2.58 (m, 2H), 2.16-1.87 (m, 9H), 1.59-1.19 (m, 8H).
Example 16
5-Cyclopentyl-5-[2-((S)-2-Cyano-pyrrolidin-1-yl)-2-oxo-ethylamino]-hexahydro-cyclopenta[c]pyrrole-2-carboxylic acid dimethylamide tartrate
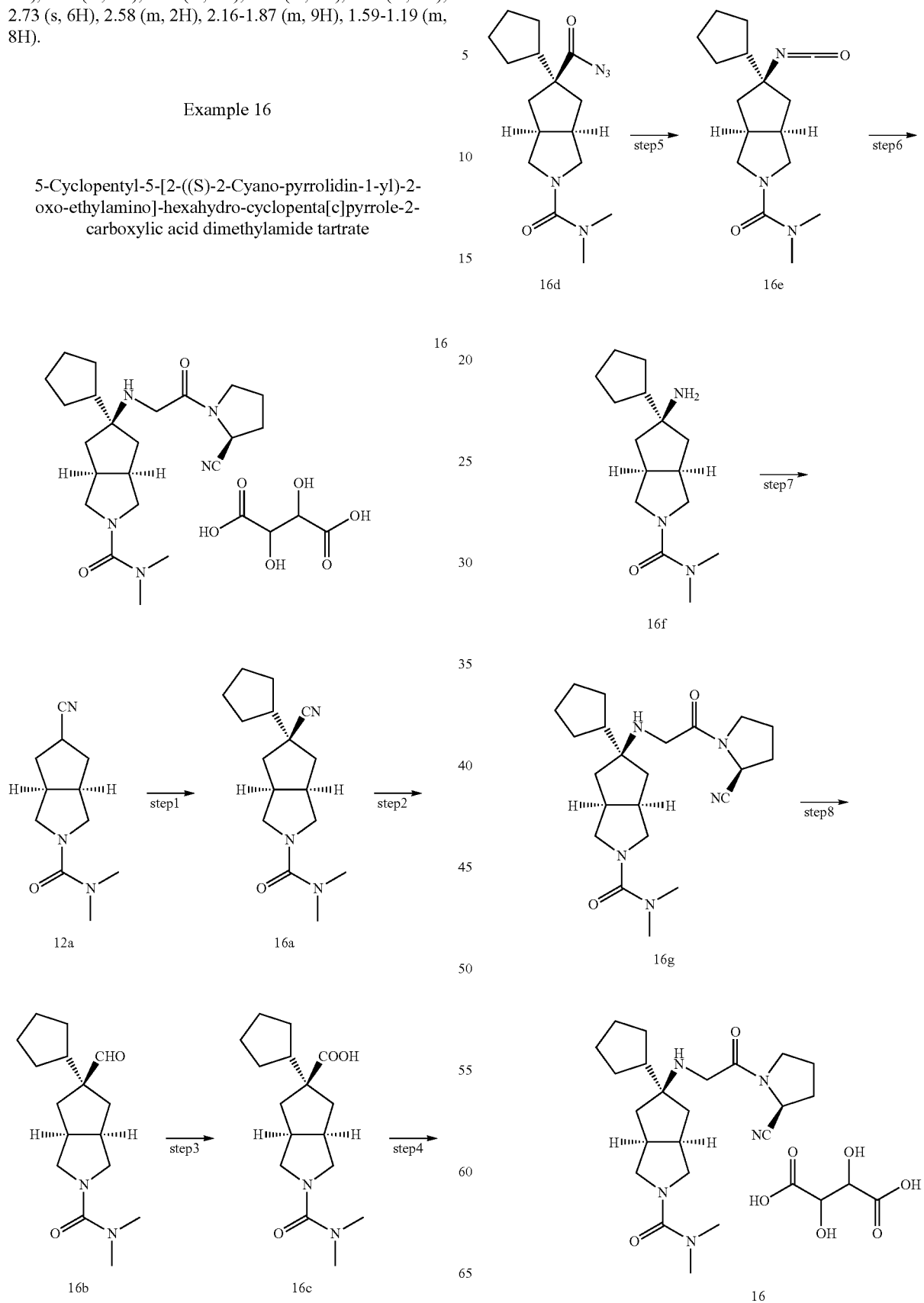

Step 1

Preparation of 5-cyano-5-cyclopentyl-hexahydro-cyclopenta[c]pyrrole-2-carboxylic acid dimethylamide 5-Cyano-hexahydro-cyclopenta[c]pyrrole-2-carboxylic acid dimethylamide 12a was dissolved in 30 mL of N,N-dimethylformamide followed by addition of iodo-cyclopentane (5.4 g, 27.5 mmol) and lithium hexamethyldisilazide (27.5 mL, 27.5 mmol) under nitrogen atmosphere. The reaction mixture was stirred at room temperature for 2 hours. The reaction was monitored by TLC until the disappearance of the starting materials. The mixture was diluted with 10 mL of water and concentrated to remove N,N-dimethylformamide and extracted with ethyl acetate. The combined organic extracts were dried over anhydrous sodium sulfate, filtered and concentrated under reduced pressure. The resulting residue was purified by silica gel column chromatography to obtain the title compound 5-cyano-5-cyclopentyl-hexahydro-cyclopenta[c]pyrrole-2-carboxylic acid dimethylamide 16a (2.6 g, yield 42%) as a light yellow solid.

MS m/z (ESI): 276.2 [M+1]

$^1$H NMR (DMSO-D$_6$, 400 MHz): δ 3.35-3.0 (m, 4H), 2.24 (s, 6H), 1.34-2.5 (m, 15H).

Step 2

Preparation of 5-cyclopentyl-5-formyl-hexahydro-cyclopenta[c]pyrrole-2-carboxylic acid dimethylamide 5-Cyano-5-cyclopentyl-hexahydro-cyclopenta[c]pyrrole-2-carboxylic acid dimethylamide 16a (0.817 g, 2.97 mmol) was dissolved in 40 mL of dichloromethane with stirring at 0° C., followed by dropwise addition of diisobutylaluminium hydride (8.9 mL, 8.9 mmol). The reaction mixture was stirred for 45 minutes. The reaction was monitored by TLC until the disappearance of the starting materials. The mixture was concentrated to remove dichloromethane and the residue was diluted with 100 mL of a saturated aqueous potassium sodium tartrate solution. The mixture was stirred until the solution was clear and extracted with ethyl acetate (100 mL×4). The combined organic extracts were dried over anhydrous magnesium sulfate, filtered and concentrated under reduced pressure. The resulting residue was purified by silica gel column chromatography to obtain the title compound 5-cyclopentyl-5-formyl-hexahydro-cyclopenta[c]pyrrole-2-carboxylic acid dimethylamide 16b (0.266 g, yield 32%) as a light yellow oil.

MS m/z (ESI): 279.3 [M+1]

Step 3

Preparation of 5-cyclopentyl-2-dimethylcarbamoyl-octahydro-cyclopenta[c]pyrrole-5-carboxylic acid 5-Cyclopentyl-5-formyl-hexahydro-cyclopenta[c]pyrrole-2-carboxylic acid dimethylamide 16b (0.266 g, 0.955 mmol) was dissolved in a solvent mixture of 20 mL of tetrahydrofuran and 10 mL of water. Then sodium dihydrogenphosphate dihydrate (0.448 g, 2.87 mmol), sodium chlorite (0.26 g, 2.87 mmol) and 2-methyl-2-butene (0.24 mL, 2.88 mmol) were added at 0° C. The reaction mixture was stirred at 0° C. for 2 hours. The reaction was monitored by TLC until the disappearance of the starting materials. The mixture was concentrated to remove tetrahydrofuran and extracted with ethyl acetate. The combined organic extracts were dried over anhydrous magnesium sulfate, filtered and concentrated under reduced pressure. The resulting residue was purified by silica gel column chromatography to obtain the title compound 5-cyclopentyl-2-dimethylcarbamoyl-octahydro-cyclopenta[c]pyrrole-5-carboxylic acid 16c (0.28 g, yield 99.6%) as a yellow solid.

MS m/z (ESI): 295.5 [M+1]

Step 4

Preparation of 5-cyclopentyl-2-dimethylcarbamoyl-octahydro-cyclopenta[c]pyrrole-5-carbonyl azide 5-Cyclopentyl-2-dimethylcarbamoyl-octahydro-cyclopenta[c]pyrrole-5-carboxylic acid 16c (0.28 g, 6.95 mmol) was dissolved in 20 mL of acetone upon cooling by an ice-water bath, followed by addition of triethylamine (0.15 mL, 1.05 mmol) and a solution of 2 mL of ethyl chloroformate (0.1 mL, 1.05 mmol) in acetone at 0° C.~−5° C. After the reaction mixture was stirred for 15 minutes, a solution of sodium azide (0.124 g, 1.9 mmol) in water was added dropwise. The reaction mixture was stirred for another 30 minutes. The reaction was monitored by TLC until the disappearance of the starting materials. The mixture was concentrated and the residue was diluted with 10 mL of water. The mixture was extracted with ethyl acetate. The combined organic extracts were dried over anhydrous magnesium sulfate, filtered and concentrated under reduced pressure to obtain the title compound 5-cyclopentyl-2-dimethylcarbamoyl-octahydro-cyclopenta[c]pyrrole-5-carbonyl azide 16d (0.287 g, yield 95%) as a yellow oil which was directly used in the next step.

Step 5

Preparation of 5-cyclopentyl-5-isocyanato-hexahydro-cyclopenta[c]pyrrole-2-carboxylic acid dimethylamide 5-Cyclopentyl-2-dimethylcarbamoyl-octahydro-cyclopenta[c]pyrrole-5-carbonyl azide 16d (0.287 g, 0.9 mmol) was dissolved in 10 mL of toluene with stirring. The reaction mixture was heated to reflux for 1 hour. The reaction was monitored by TLC until the disappearance of the starting materials. The mixture was concentrated to obtain the title compound 5-cyclopentyl-5-isocyanato-hexahydro-cyclopenta[c]pyrrole-2-carboxylic acid dimethylamide 16e which was directly used in the next step.

MS m/z (ESI): 292.3 [M+1]

Step 6

Preparation of 5-amino-5-cyclopentyl-hexahydro-cyclopenta[c]pyrrole-2-carboxylic acid dimethylamide Upon cooling by an ice-water bath, to a solution of 10 mL hydrochloric acid (8 N) was added dropwise 5-cyclopentyl-5-isocyanato-hexahydro-cyclopenta[c]pyrrole-2-carboxylic acid dimethylamide 16e obtained from the above step. Then the ice-water bath was removed and the reaction mixture was reacted at 50° C. for 15 minutes. The reaction was monitored by TLC until the disappearance of the starting materials. The mixture was adjusted to pH>8 with concentrated ammonia and extracted with ethyl acetate. The combined organic extracts were dried over anhydrous magnesium sulfate, filtered and concentrated under reduced pressure. The resulting residue was purified by silica gel column chromatography to obtain the title compound 5-amino-5-cyclopentyl-hexahydro-cyclopenta[c]pyrrole-2-carboxylic acid dimethylamide 16f (0.18 g, yield 81.8%) as a yellow oil.

MS m/z (ESI): 266.2 [M+1]

Step 7

Preparation of 5-cyclopentyl-5-[2-((S)-2-cyano-pyrrolidin-1-yl)-2-oxo-ethylamino]-hexahydro-cyclopenta[c]pyrrole-2-carboxylic acid dimethylamide 5-Amino-5-cyclopentyl-hexahydro-cyclopenta[c]pyrrole-2-carboxylic acid dimethylamide 16f (0.108 g, 0.407 mmol) and 1-(2-chloro-acetyl)-pyrrolidine-2-cyano (70 mg, 0.407 mmol) were dissolved in 3 mL of N,N-dimethylformamide with stirring followed by addition of potassium carbonate (57 mg, 0.407 mmol) under nitrogen atmosphere. The reaction mixture was reacted overnight at 80° C. upon heating by an oil bath. The reaction was monitored by TLC until the disappearance of the starting materials. The mixture was concentrated, and the resulting residue was purified by silica gel column chromatography to obtain the title compound 5-cyclopentyl-5-[2-((S)-2-cyano-pyrrolidin-1-yl)-2-oxo-ethylamino]-hexahydro-cyclopenta[c]pyrrole-2-carboxylic acid dimethylamide 16g (100 mg, yield 61.3%) as a colorless oil.

MS m/z (ESI): 402.3 [M+1]

Step 8

Preparation of 5-cyclopentyl-5-[2-((S)-2-cyano-pyrrolidin-1-yl)-2-oxo-ethylamino]-hexahydro-cyclopenta[c]pyrrole-2-carboxylic acid dimethylamide tartrate 5-Cyclopentyl-5-[2-((S)-2-cyano-pyrrolidin-1-yl)-2-oxo-ethylamino]-hexahydro-cyclopenta[c]pyrrole-2-carboxylic acid dimethylamide 16g (102 mg, 0.254 mmol) was dissolved in 2 mL of ethyl acetate followed by addition of a solution of 3 mL of tartaric acid in acetone. The reaction mixture was stirred for 30 minutes resulting in the formation of a white precipitate followed by addition of n-hexane, and stirred again. The mixture was filtered to obtain the title compound 5-cyclopentyl-5-[2-((S)-2-cyano-pyrrolidin-1-yl)-2-oxo-ethylamino]-hexahydro-cyclopenta[c]pyrrole-2-carboxylic acid dimethylamide tartrate 16 (88 mg, yield 65%) as a white solid.

Example 17

5-Benzyl-5-[2-((S)-2-cyano-pyrrolidin-1-yl)-2-oxo-ethylamino]-hexahydro-cyclopenta[c]pyrrole-2-carboxylic acid dimethylamide tartrate

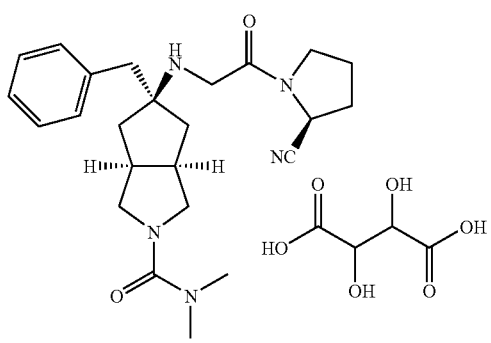

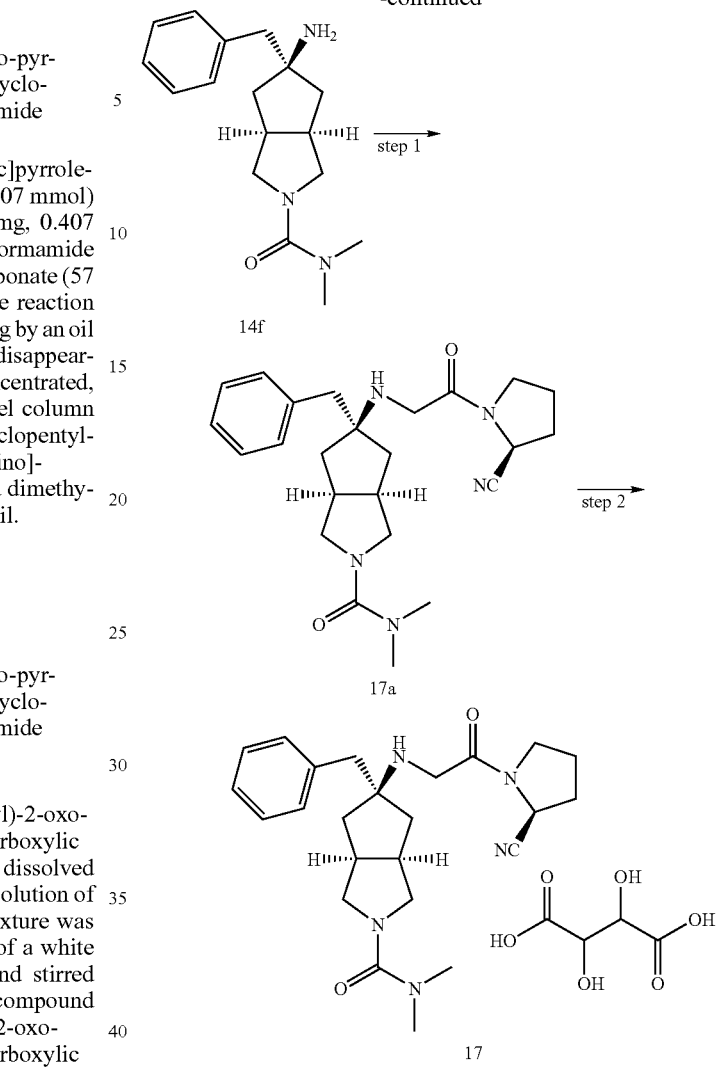

Step 1

Preparation of 5-benzyl-5-[2-((S)-2-cyano-pyrrolidin-1-yl)-2-oxo-ethylamino]-hexahydro-cyclopenta[c]pyrrole-2-carboxylic acid dimethylamide 5-Amino-5-benzyl-hexahydro-cyclopenta[c]pyrrole-2-carboxylic acid dimethylamide 14f (0.1 g, 0.35 mmol), 1-(2-chloro-acetyl)-pyrrolidine-2-cyano (120.4 mg, 0.7 mmol) and potassium carbonate (49 mg, 0.35 mmol) were dissolved in 3 mL of N,N-dimethylformamide under nitrogen atmosphere. The reaction mixture was reacted overnight at 80° C. upon heating by an oil bath. The reaction was monitored by TLC until the disappearance of the starting materials. The mixture was concentrated, and the resulting residue was purified by silica gel column chromatography to obtain the title compound 5-benzyl-5-[2-((S)-2-cyano-pyrrolidin-1-yl)-2-oxo-ethylamino]-hexahydro-cyclopenta[c]pyrrole-2-carboxylic acid dimethylamide 17a (56 mg, yield 40%) as a colorless oil.

MS m/z (ESI): 424.3 [M+1]

Step 2

Preparation of 5-benzyl-5-[2-((S)-2-cyano-pyrrolidin-1-yl)-2-oxo-ethylamino]-hexahydro-cyclopenta[c]pyrrole-2-carboxylic acid dimethylamide tartrate 5-Benzyl-5-[2-((S)-2-cyano-pyrrolidin-1-yl)-2-oxo-ethylamino]-hexahydro-cyclopenta[c]pyrrole-2-carboxylic acid dimethylamide 17a (56 mg, 0.132 mmol) was dissolved in 1 mL of ethyl acetate with stirring followed by addition of a solution of 1 mL of tartaric acid in acetone. The reaction mixture was stirred for 30 minutes resulting in the formation of a white precipitate followed by addition of n-hexane, and stirred again. The mixture was filtered to obtain the title compound 5-benzyl-5-[2-((S)-2-cyano-pyrrolidin-1-yl)-2-oxo-ethylamino]-hexahydro-cyclopenta[c]pyrrole-2-carboxylic acid dimethylamide tartrate 17 (50 mg, yield 67%) as a white solid.

$^1$H NMR (DMSO-D$_6$, 400 MHz): δ 7.32-7.19 (m, 5H), 4.78 (m, 1H), 4.23 (s, 2H), 3.8-3.0 (m, 8H), 2.75 (s, 2H), 2.73 (s, 6H), 2.18 (m, 2H), 2.16 (m, 2H), 1.87 (m, 3H), 1.35 (m, 3H).

Example 18

5-[2-((2S,4S)-2-Cyano-4-fluoro-pyrrolidin-1-yl)-2-oxo-ethylamino]-5-methyl-hexahydro-cyclopenta[c]pyrrole-2-carboxylic acid dimethylamide p-toluenesulfonate

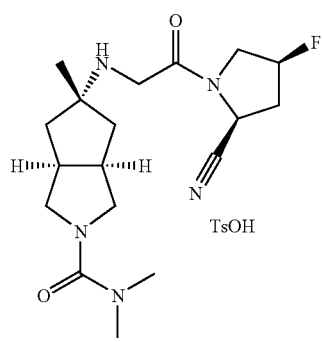

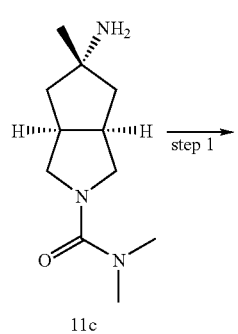
11c

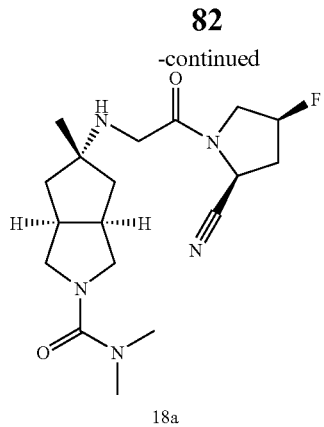
18a

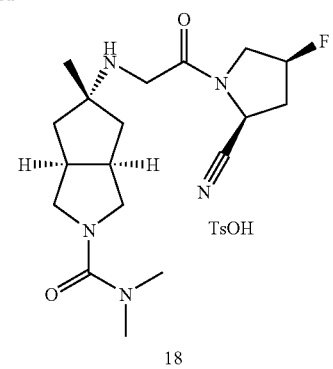
18

Step 1

Preparation of 5-[2-((2S,4S)-2-cyano-4-fluoro-pyrrolidin-1-yl)-2-oxo-ethylamino]-5-methyl-hexahydro-cyclopenta[c]pyrrole-2-carboxylic acid dimethylamide 5-Amino-5-methyl-hexahydro-cyclopenta[c]pyrrole-2-carboxylic acid dimethylamide 11c (1.3 g, 7.58 mmol), (2S,4S)-1-(2-chloroacetyl)-4-fluoropyrrolidine-2-carbonitrile 13g (1.74 g, 9.1 mmol), potassium carbonate (1.26 g, 9.1 mmol), 30 mL of N,N-dimethylformamide and 18 mL of dichloromethane were added to a flask under nitrogen atmosphere. The reaction mixture was reacted for overnight at 30° C. upon heating by an oil bath. The reaction was monitored by TLC until the disappearance of the starting materials. The mixture was concentrated to remove N,N-dimethylformamide. The resulting residue was purified by silica gel column chromatography to obtain the title compound 5-[2-((2S,4S)-2-cyano-4-fluoro-pyrrolidin-1-yl)-2-oxo-ethylamino]-5-methyl-hexahydro-cyclopenta[c]pyrrole-2-carboxylic acid dimethylamide 18a (1.39 g, yield 50%) as a white solid.

MS m/z (ESI): 348.2 [M+1]

Step 2

Preparation of 5-[2-((2S,4S)-2-cyano-4-fluoro-pyrrolidin-1-yl)-2-oxo-ethylamino]-5-methyl-hexahydro-cyclopenta[c]pyrrole-2-carboxylic acid dimethylamide p-toluenesulfonate 5-[2-(2-Cyano-4-fluoro-pyrrolidin-1-yl)-2-oxo-ethylamino]-5-methyl-hexahydro-cyclopenta[c]pyrrole-2-carboxylic acid dimethylamide 18a (0.9 g, 2.47 mmol) was dissolved in 5 mL of dichloromethane with stirring at room temperature. To a solution of p-toluenesulfonic acid monohydrate (469 mg, 2.47 mmol) in 3 mL of acetone was added the above mentioned solution, which resulted in the formation of a white precipitate. The reaction mixture was stirred for 30 minutes followed by addition of 1 mL of n-hexane. The mixture was filtered to obtain the title compound 5-[2-((2S, 4S)-2-cyano-4-fluoro-pyrrolidin-1-yl)-2-oxo-ethylamino]-5-methyl-hexahydro-cyclopenta[c]pyrrole-2-carboxylic acid dimethylamide p-toluenesulfonate 18 (1.3 g, yield 93%) as a white solid.

MS m/z (ESI): 366.1 [M+1]

$^1$H NMR (DMSO-D$_6$, 400 MHz): δ 7.74 (d, 2H), 7.29 (d, 2H), 5.57-5.44 (m, 1H), 5.07 (m, 1H), 4.19-4.07 (m, 4H), 3.49 (m, 2H), 3.35 (m, 2H), 3.0 (m, 2H), 2.9 (s, 6H), 2.6 (m, 2H), 2.39 (m, 5H), 1.57 (m, 2H), 1.34 (s, 3H).

Example 19

5-Ethyl-5-[2-((S)-2-cyano-pyrrolidin-1-yl)-2-oxo-ethylamino]-hexahydro-cyclopenta[c]pyrrole-2-carboxylic acid dimethylamide tartrate

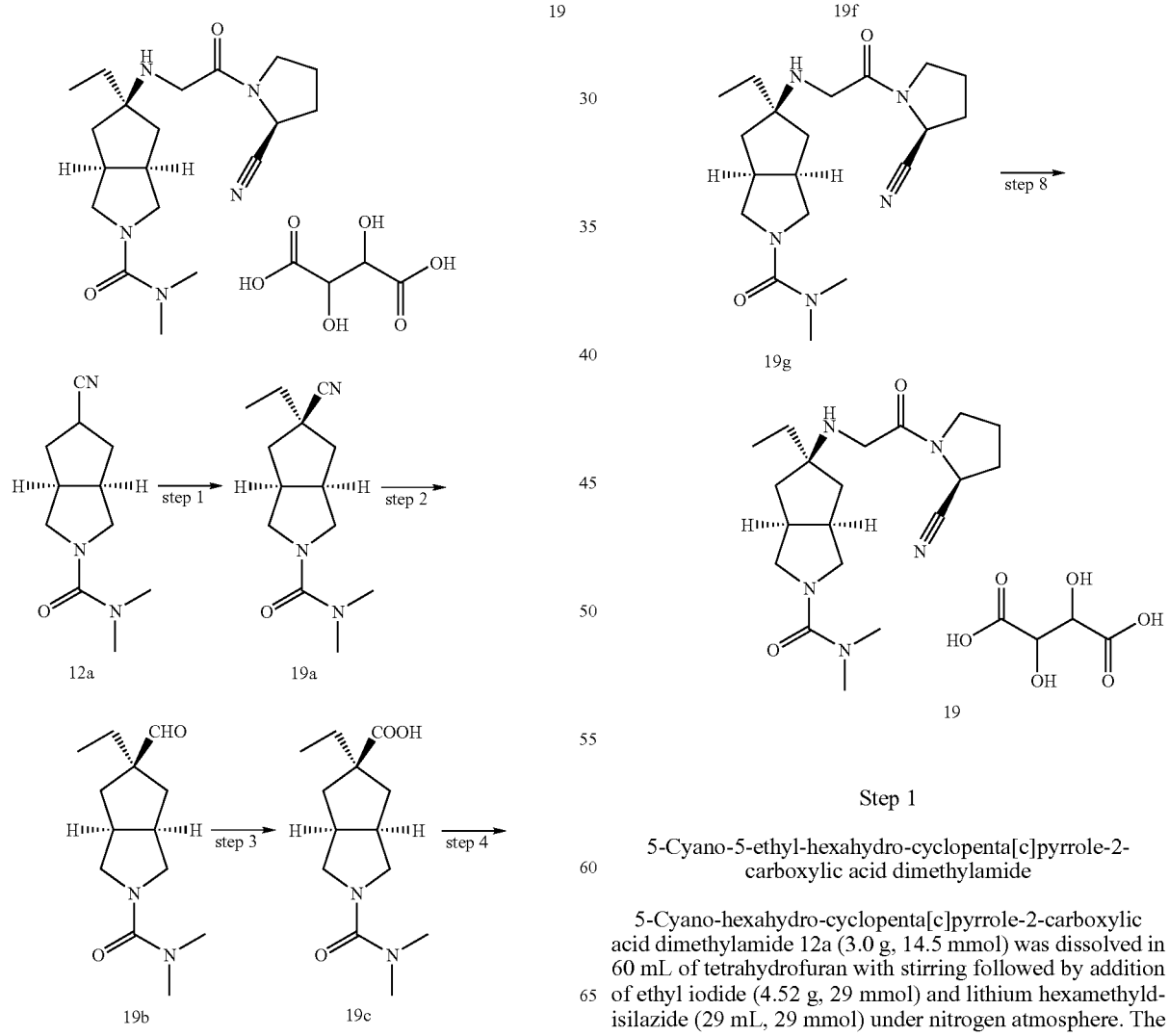

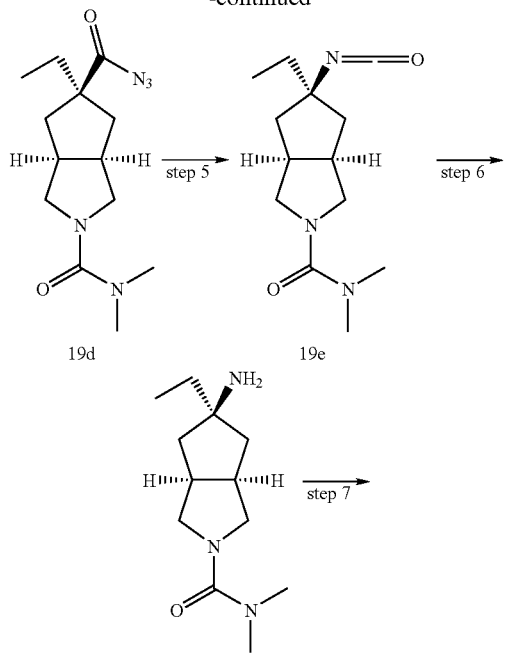

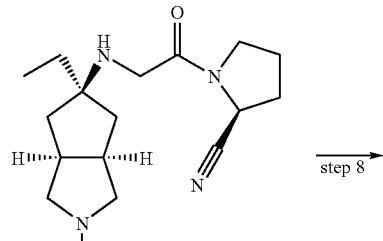

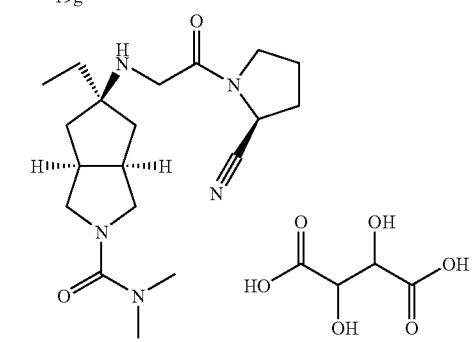

Step 1

5-Cyano-5-ethyl-hexahydro-cyclopenta[c]pyrrole-2-carboxylic acid dimethylamide

5-Cyano-hexahydro-cyclopenta[c]pyrrole-2-carboxylic acid dimethylamide 12a (3.0 g, 14.5 mmol) was dissolved in 60 mL of tetrahydrofuran with stirring followed by addition of ethyl iodide (4.52 g, 29 mmol) and lithium hexamethyldisilazide (29 mL, 29 mmol) under nitrogen atmosphere. The reaction mixture was reacted at room temperature for 2 hours.

The reaction was monitored by TLC until the disappearance of the starting materials. The mixture was diluted with 20 mL of water and extracted with ethyl acetate (200 mL×3). The combined organic extracts were dried over anhydrous sodium sulfate, filtered and concentrated under reduced pressure to obtain an oil. TLC showed that there are two adjacent spots, and then the oil was purified by silica gel column chromatography to obtain the title compound 5-cyano-5-ethyl-hexahydro-cyclopenta[c]pyrrole-2-carboxylic acid dimethylamide 19a (1.64 g) as a light yellow solid.

MS m/z (ESI): 236.3 [M+1]

$^1$H NMR (DMSO-D$_6$, 400 MHz): δ 3.5-3.0 (m, 4H), 2.7 (s, 6H), 1.9-1.2 (m, 8H), 1.19 (m, 3H).

Step 2

Preparation of 5-ethyl-5-formyl-N,N-dimethyl-hexahydro-cyclopenta[c]pyrrole-2-carboxamide 5-Cyano-5-ethyl-hexahydro-cyclopenta[c]pyrrole-2-carboxylic acid dimethylamide 19a (1.54 g, 6.55 mmol) was dissolved in 60 mL of dichloromethane. Diisobutylaluminium hydride (19.6 mL, 19.6 mmol) was added dropwise at 0° C. The reaction mixture was stirred at 0° C. for 30 minutes. The reaction was monitored by TLC until the disappearance of the starting materials. The mixture was quenched with 1.5 mL of water, dried over anhydrous magnesium sulfate, filtered and concentrated under reduced pressure to obtain the title compound 5-ethyl-5-formyl-N,N-dimethyl-hexahydro-cyclopenta[c]pyrrole-2-carboxamide 19b (0.4 g, yield 26%) as a light yellow oil.

MS m/z (ESI): 239.1 [M+1]

Step 3

Preparation of 5-ethyl-2-dimethylcarbamoyl-hexahydro-cyclopenta[c]pyrrole-5-carboxylic acid 5-Ethyl-5-formyl-N,N-dimethyl-hexahydro-cyclopenta[c]pyrrole-2-carboxylic acid dimethylamide 19b (0.4 g, 1.68 mmol) was dissolved in the solvent mixture of 18 mL of tetrahydrofuran and 9 mL of water, followed by addition of sodium dihydrogenphosphate dihydrate (787 mg, 5.04 mmol), sodium chlorite (0.454 g, 5.04 mmol) and 2-methyl-2-butene (354 mg, 5.06 mmol) at 0° C. The reaction mixture was reacted at 0° C. for 2 hours under nitrogen atmosphere. The reaction was monitored by TLC until the disappearance of the starting materials. The mixture was extracted with ethyl acetate. The combined organic extracts were dried over anhydrous magnesium sulfate, filtered and concentrated under reduced pressure to obtain the title compound 5-ethyl-2-dimethylcarbamoyl-hexahydro-cyclopenta[c]pyrrole-5-carboxylic acid 19c (0.426 g, yield 100%) as a yellow solid which was directly used in the next step.

MS m/z (ESI): 255.2 [M+1]

Step 4

Preparation of 5-ethyl-2-dimethylcarbamoyl-hexahydro-cyclopenta[c]pyrrole-5-carbonyl azide 5-Ethyl-2-dimethylcarbamoyl-hexahydro-cyclopenta[c]pyrrole-5-carboxylic acid 19c (0.56 g, 2.2 mmol) was dissolved in 60 mL of acetone upon cooling by an ice-water bath. When cooled to −5° C., triethylamine (0.245 mg, 2.43 mmol) and a solution of 2 mL of ethyl chloroformate (263 mg, 2.43 mmol) in acetone were added dropwise. After the reaction mixture was stirred for 15 minutes, a solution of sodium azide (0.286 g, 4.4 mmol) in 2 mL of water was added. The reaction mixture was stirred at −5° C.~0° C. for another 30 minutes. The reaction was monitored by TLC until the disappearance of the starting materials. The mixture was diluted with 10 mL of water, extracted with ethyl acetate (10 mL×5). The combined organic extracts were dried over anhydrous magnesium sulfate, filtered and concentrated under reduced pressure to obtain the title compound 5-ethyl-2-dimethylcarbamoyl-hexahydro-cyclopenta[c]pyrrole-5-carbonyl azide 19d (0.5 g) as a light yellow oil which was directly used in the next step.

Step 5

Preparation of 5-ethyl-5-isocyanato-hexahydro-cyclopenta[c]pyrrole-2-carboxylic acid dimethylamide 5-Ethyl-2-dimethylcarbamoyl-hexahydrocyclopenta[c]pyrrole-5-carbonyl azide 19d (0.5 g, 1.86 mmol) was dissolved in 30 mL of toluene. The reaction mixture was heated to reflux for 2 hour. The reaction was monitored by TLC until the disappearance of the starting materials. The mixture was concentrated to obtain the title compound 5-ethyl-5-isocyanato-hexahydro-cyclopenta[c]pyrrole-2-carboxylic acid dimethylamide 19e, which was directly used in the next step.

Step 6

Preparation of 5-amino-5-ethyl-hexahydro-cyclopenta[c]pyrrole-2-carboxylic acid dimethylamide To a solution of 12 mL hydrochloric acid (8 N) was added 5-ethyl-5-isocyanato-hexahydro-cyclopenta[c]pyrrole-2-carboxylic acid dimethylamide 19e obtained from the above step at room temperature. The reaction mixture was stirred for 30 minutes and adjusted to pH 9-10 with an 8 N aqueous sodium hydroxide solution. The separated aqueous layer was extracted with dichloromethane (30 mL×5). The combined organic extracts were dried over anhydrous magnesium sulfate, filtered and concentrated under reduced pressure. The resulting residue was purified by silica gel column chromatography to obtain the title compound 5-amino-5-ethyl-hexahydro-cyclopenta[c]pyrrole-2-carboxylic acid dimethylamide 19f (0.3 g, yield 71%) as a colorless oil.

MS m/z (ESI): 226.2 [M+1]

Step 7

Preparation of 5-ethyl-5-[2-((S)-2-cyano-pyrrolidin-1-yl)-2-oxo-ethylamino]-hexahydro-cyclopenta[c]pyrrole-2-carboxylic acid dimethylamide 5-Amino-5-ethyl-hexahydro-cyclopenta[c]pyrrole-2-carboxylic acid dimethylamide 19f (0.202 g, 0.897 mmol), 1-(2-chloro-acetyl)-pyrrolidine-2-cyano (185 mg, 1.07 mmol), potassium carbonate (148 mg, 1.07 mmol) and a solvent mixture of 9 mL of N,N-dimethylformamide/dichloromethane (V/V=1/1) were added to a flask under nitrogen atmosphere. The reaction mixture was reacted at 60° C. for 2 hours. The reaction was monitored by TLC until the disappearance of the starting materials. The mixture was concentrated under reduced pressure to remove dichloromethane and N,N-dimethylformamide. The resulting residue was purified by silica gel column chromatography to obtain the title compound 5-[2-((S)-2-cyano-pyrrolidin-1-yl)-2-oxo-ethylamino]-5-ethyl-hexahydro-cyclopenta[c]pyrrole-2-carboxylic acid dimethylamide 19g (120 mg, yield 40%) as a light yellow oil.

MS m/z (ESI): 362.2 [M+1]

Step 8

Preparation of 5-ethyl-5-[2-((S)-2-cyano-pyrrolidin-1-yl)-2-oxo-ethylamino]-hexahydro-cyclopenta[c]pyrrole-2-carboxylic acid dimethylamide tartrate 5-[2-((S)-2-Cyano-pyrrolidin-1-yl)-2-oxo-ethylamino]-5-ethyl-hexahydro-cyclopenta[c]pyrrole-2-carboxylic acid dimethylamide 19g (120 mg, 0.33 mmol) was dissolved in 1 mL of ethyl acetate followed by dropwise addition of a solution of 2 mL of tartaric acid (50 mg, 0.33 mmol) in acetone. The reaction mixture was stirred for 30 minutes and filtered to obtain the title compound 5-[2-((S)-2-cyano-pyrrolidin-1-yl)-2-oxo-ethylamino]-5-ethyl-hexahydro-cyclopenta[c]pyrrole-2-carboxylic acid dimethylamide tartrate 19 (160 mg, yield 94%) as a white solid.

MS m/z (ESI): 362.2 [M+1]
$^1$H NMR (DMSO-$D_6$, 400 MHz): δ 4.79 (m, 1H), 4.11 (s, 2H), 3.65 (m, 2H), 3.49 (m, 2H), 3.22 (m, 4H), 2.75 (s, 6H), 2.55 (m, 2H), 2.19 (m, 2H), 2.09 (m, 2H), 1.99 (m, 2H), 1.51 (m, 4H), 0.86 (t, 3H).

Test Examples

Biological Assays

Assay for DPP-IV/DPP-VIII/DPP-IX Inhibitory Activity

The following methods can be used to measure the activities of the compounds of the present disclosure that inhibit the enzymatic activity of DPP-IV/DPP-VIII/DPP-IX. The compounds of the present disclosure are tested for their ability to inhibit the enzyme activity of purified DPP-IV/DPP-VIII/DPP-IX. The inhibitory rate or the half inhibition concentration $IC_{50}$ (concentration of the test compound at which 50% of the enzyme activity is inhibited) for each compound is determined by incubating fixed amounts of mixed enzyme substrates with several different concentrations of test compounds.

Assay for -DPP-IV Inhibitory Activity

Materials and Methods:
Materials:
a. 96-well white plate (BMG).
b. Tris buffer: in order to prepare 100 mL of 2 mM Tris Buffer, 0.0242 g Tris was dissolved in about 90 mL distilled $H_2O$ ($dH_2O$) firstly. Hydrochloric acid and sodium hydroxide was used to adjust pH to 8.00 and then the solution was diluted with $dH_2O$ to 100 mL in total volume.
c. DPP-IV enzyme (Calbiochem Catalog No. 317630) was dissolved in Tris buffer to make a 2 mM solution.
d. DPP-IV—Glo™ substrate (Promega Catalog No. G8350) was dissolved in $dH_2O$ to make a 1 mM solution.
e. DPP-IV—Glo buffer solution (Promega Catalog No. G8350).
f. Luciferin detection reagent (Promega Catalog No. G8350).
g. DMSO.
h. $dH_2O$.

Procedure:
The assay was carried out as follows:
1. DPP-IV-Glo. buffer was thawed and equilibrated to room temperature prior to use.
2. The freezing luciferin detection reagent was equilibrated to room temperature prior to use.
3. DPP-IV—Glo. substrate was mixed with ultrapure water by vortexing briefly to form a 1 mM solution of the substrate.
4. The luciferin detection reagent was placed in a brown bottle with addition of DPP-IV—Glo. buffer, and the luciferin agent was dissolved within 1 minute.
5. The test compounds were dissolved in DMSO at a concentration of 50 times of the final concentration.
6. 2 μL of the test compound solution with 50 times concentration was added to each tube, and 2 μL of DMSO was added to the negative control and blank control instead.
7. 46 μL of Tris buffer was added to each tube and 48 μL of Tris buffer was added in the blank control.
8. 2 μL of DPP-IV enzyme was added to each negative control tube and test tube.
9. The test tubes were shaken and centrifuged, and then the substances of the test tube were transferred to 96-well plates.
10. The substrate and DPP-IV—Glo. were mixed in a ratio of 1:49, and this mixture was shaken throughfully and incubated at room temperature for 30-60 minutes prior to use.
11. The 96-well plate was sealed by a sealing film after 50 μL of the mixed solution of DPP-IV—Glo. and substrate were added to each well.
12. The substances of the 96 wells were mixing slowly by using a plate shaker at 300-500 rpm/30 s, and then the plate was incubated at room temperature from 30 minutes to 3 hours.
13. The luminescence value was measured.
The definition of inhibitory rate:

[1−(S−B)/(N−B)]*100%

S: sample
B: blank control
N: negative control

Assay for DPP-VIII Inhibitory Activity

Materials and Methods:
Materials:
a. 96-well white plate (BMG).
b. Tris buffer: in order to prepare 100 mL 2 mM Tris buffer, 0.0242 g Tris was dissolved in about 90 mL $dH_2O$ firstly. Hydrochloric acid and sodium hydroxide were used to adjust pH to 8.00 and then the solution was diluted with $dH_2O$ to 100 mL in total volume.
c. DPP-VIII enzyme (Bioscience Catalog No. 80080) was dissolved in 25 mL of Tris-HCl, pH=8.0, 100 mM NaCl, 0.05% Tween-20, 50% glycerol, and 3 mM DTT Buffer. The final concentration was 0.1 ng/100 μL assay.
d. DPP-VIII—Glo™ substrate (Promega Catalog No. G8350) was dissolved in $dH_2O$ to make a 1 mM solution.
e. DPP-VIII—Glo. buffer solution (Promega Catalog No. G8350).
f. Luciferin detection reagent (Promega Catalog No. G8350).
g. DMSO.
H. $dH_2O$.

Procedure:
The assay was carried out as follows:
1. DPP-VIII—Glo. buffer was thawed and equilibrated to room temperature prior to use.

2. The freezing luciferin detection reagent was equilibrated to room temperature prior to use.

3. DPP-VIII—Glo. substrate was mixed with ultrapure water by vortexing briefly to form 1 mM substrate.

4. The luciferin detection reagent was placed in a brown bottle with addition of DPP-VIII—Glo. buffer, and the luciferin agent was dissolved within 1 minute.

5. The test compounds were dissolved in DMSO to 50 times of the final concentration.

6. 2 µL of the test compound solution with 50 times concentration was added to each tube, and 2 µL of DMSO was added to the negative control and blank control instead.

7. 46 µL of Tris buffer was added to each tube and 48 µL of Tris buffer was added in blank control.

8. 2 µL of DPP-VIII enzyme was added to each negative control tube and test tube.

9. The tested tubes were shaken and centrifuged, and then the substances of the solution in the test tube were transferred to 96-well plates.

10. The substrate and DPP-VIII—Glo. were mixed in a ratio of 1:49, and this mixture was shaken throughfully and incubated at room temperature for 30-60 minutes prior to use.

11. The 96-well plate was sealed by a sealing film after 50 µL of the mixed solution of DPP-VIII—Glo. and substrate were added to each well.

12. The substances of the 96 wells were mixing slowly by using a plate shaker at 300-500 rpm/30 s, and then the plate was incubated at room temperature from 30 minutes to 3 hours.

13. The luminescence value was measured.

The definition of inhibitory rate:

[1−(S−B)/(N−B)]*100%

S: sample
B: blank control
N: negative control

Assay for DPP-IX Inhibitory Activity

Materials and Methods:
Materials:
  a. 96-well white plate (BMG);
  b. Tris buffer: in order to prepare 100 mL 2 mM Tris Buffer, 0.0242 g Tris was dissolved in about 90 mL $dH_2O$ firstly. Hydrochloric acid and sodium hydroxide were used to adjust pH to 8.00 and then the solution was diluted with $dH_2O$ to 100 mL in total volume;
  c. DPP-IX enzyme (Bioscience Catalog No. 80090) was dissolved in 25 mL of Tris-HCl, pH=8.0, 100 mM NaCl, 0.05% Tween-20, 50% glycerol, and 3 mM DTT Buffer. The final concentration was 0.1 ng/100 µL assay,
  d. DPP-IX—Glo™ substrate (Promega Catalog No. G8350), dissolved in $dH_2O$ to make a 1 mM solution.
  e. DPP-IX—Glo. buffer solution (Promega Catalog No. G8350).
  f. Luciferin detection reagent (Promega Catalog No. G8350).
  g. DMSO.
  h. $dH_2O$.
Procedure:
1. The assay was carried out as follows:
2. DPP-IX—Glo. buffer was thawed and equilibrated to room temperature prior to use.
3. The freezing luciferin detection reagent was equilibrated to room temperature prior to use.
4. DPP-IX—Glo. substrate was mixed with ultrapure water by vortexing briefly to form 1 mM substrate.

5. The luciferin detection reagent was placed in a brown bottle with addition of DPP-IX—Glo. buffer, and the luciferin agent was dissolved within 1 minute.

6. The test compounds were dissolved in DMSO at a concentration of 50 times the final concentration.

7. 2 µL of the test compound solution with 50 times concentration was added to each tube, and 2 µL of DMSO was added to negative control and blank control for instead.

8. 46 µL of Tris buffer was added to each tube and 48 µL of Tris buffer was added in blank control.

9. 2 µL of DPP-1× enzyme was added to each negative control tube and test tube.

10. The test tubes were shaken and centrifuged, and then the substances of the test tube were transferred to 96-well plates.

11. The substrate and DPP-IX—Glo. were mixed in a ratio of 1:49, and this mixture was shaken throughfully and incubated at room temperature for 30-60 minutes prior to use.

12. The 96-well plate was sealed by a sealing film after 50 µL of the mixed solution of DPP-IX—Glo. and substrate were added to each well.

13. The substances of the 96 wells were mixing slowly by using a plate shaker at 300-500 rpm/30 s, and then the plate was incubated at room temperature from 30 minutes to 3 hours.

The luminescence value was measured.
The definition of inhibitory rate:

[1−(S−B)/(N−B)]*100%

S: sample
B: blank control
N: negative control $IC_{50}$ of the DPP-IV/DPP-VIII/DPP-IX of the test compounds were showed in table 1.

TABLE 1

$IC_{50}$ Assay Results of Examples

| Example | IC50(nM) DPP-IV | IC50(nM) DPP-VIII | IC50(nM) DPP-IX |
|---|---|---|---|
| 1 | 16 | 17380 | 5700 |
| 2 | 24 | 18240 | 5040 |
| 3 | 14 | | |
| 4 | 69 | | |
| 7 | 50 | | |
| 8 | 39 | | |
| 10 | 83 | | |
| 11 | 13 | 38480 | 2434 |
| 12 | 13 | 4890 | 16900 |
| 13 | 10 | 371 | 516 |
| 18 | 39 | 3320 | 380 |

Preliminary Evaluation of Hypoglycemic Effects of DPP-IV Inhibitors

Objective:
  To observe the effects on oral glucose tolerance of the DPP-IV inhibitors the compounds of Example 1 and Example 2 in normal ICR mice, the hypoglycemic effects in vivo have been evaluated.
Test Animals:
  Species, strains: ICR mice
  Source: Chinese Academy of Sciences, Shanghai Laboratory Animal Center, Certification No.: SYXK (Shanghai) 2004-2005
  Weight: 25-30 g
  Sex: Male Animal Number: 40

Rearing conditions: SPF-class animal room raising, temperature: 22-24° C., Humidity: 45-80%, illumination: 150-300Lx, day and night cycle with an interval of 12 hours.

Drugs:
Name: the compound of Example 1
Lot Number: 01
Color, form: white powder
Purity: 96.97%
Provided by: Shanghai Hengrui Medicine Co., Ltd.
Preparation Method: Compounds were Weighed Accurately, and then dissolved in double distilled water. The suspensions of 0.5, 0.15 and 0.05 mg/mL were prepared, respectively. (Note: Although the product instruction displayed the test compounds were soluble in water, but in the experiment it was poorly water-soluble, i.e., at a low concentration it can be dissolved, but at the concentration of 0.5 mg/mL, there are still visible particles to the naked eye. 1% CMC was tried to suspend the compounds, while it was not better than double-distilled water.)
Dose: 1, 3, 10 mg/kg by gavage. The volume is 20 mL/kg.
Name: the compound of Example 2
Lot Number: 01
Color, form: white powder
Purity: 96.62%
Provided by: Shanghai Hengrui Medicine Co., Ltd.
Preparation Method: Compounds were Weighed Accurately, and then Dissolved in double distilled water and fully mixed to prepare a 1.5 mg/mL solution, and then diluted into 0.5, 0.15 and 0.05 mg/mL transparent solutions, respectively.
Dose: 1, 3, 10 mg/kg by gavage. The volume is 20 mL/kg.

Method:

1. The effects of compounds on blood glucose levels in normal ICR mice

Normal male ICR mice were randomly grouped according to weights, 6 mice in each group. The groups included a black control group as well as different doses of the treatment groups as follows:

Test 1:
Blank control: double-distilled water by gavage.
Group 1: the compound of Example 1, 1 mg/kg by gavage; the compound of Example 1, 3 mg/kg by gavage; and the compound of Example 1, 10 mg/kg by gavage.
Group 2: the compound of Example 2, 1 mg/kg by gavage; the compound of Example 2, 3 mg/kg by gavage; and the compound of Example 2, 10 mg/kg by gavage.

Test 2:
Blank control: double-distilled water by gavage.
Group 1: the compound of Example 1, 1 mg/kg by gavage; the compound of Example 1, 3 mg/kg by gavage; and the compound of Example 1, 10 mg/kg by gavage.
Group 2: the compound of Example 2, 1 mg/kg by gavage; the compound of Example 2, 3 mg/kg by gavage; and the compound of Example 2, 10 mg/kg by gavage.

Animals in each group had been fasted for 6 hours, and then pretreated with test compounds or double distilled water by gavage respectively in single administration. 30 minutes later, animals were administered with 2.5 g/kg glucose by gavage. Before administration and after administration of glucose at 30, 60 and 120 minutes, blood was taken to measure serum glucose levels.

2. Serum Glucose Determination:

Serum glucose is measured by glucose kits. 250 µl working enzyme solution was taken, and then 5 µl serum was added to the solution. A blank tube (5 µl double distilled water was added) and a standard tube (5 µl glucose standard solution was added) were established simultaneously and shaken in 37° C. water bath for 20 minutes. The blank tube was used to set the instrument to zero, the colorimetric assay was performed at OD 505 nm.

Serum glucose concentration ($BG$, mmol/l)= $OD_{sample\ tube}/OD_{standard\ tube} \times 5.55$ Data Processing and Statistical Analysis:

1. Mean±SD and Student-t test were used in statistical analysis.

2. The percentage of declines in blood glucose after 30 minutes of sugar administration as well as the area under the curve (AUC) were calculated.

Results:

Test 1:

Male ICR mice were fasted for 6 hours, and then treated with double distilled water, different doses of the test compounds of Example 1 and Example 2 by gavage. 30 minutes after administration, the oral glucose tolerance test was conducted. The results showed that the blood glucose level in the control group increased significantly after 2.5 g/kg glucose had been administered by gavage, and reached the peak at 30 minutes. At low, middle and high doses of the compound of Example 1, the blood glucose level was significantly lower than the control group at 30 minutes, and the percentage of the blood glucose had decreased by 19.16%, 22.85% and 31.85%, respectively. At each dose of the compound of Example 2, the blood glucose level was significantly lower than the control group at 30 minutes after the administration of glucose (P<0.01). Compared with the control group, the percentage of blood glucose had decreased by 25.54%, 25.92% and 26.93%.

Test 2:

Male ICR mice were fasted for 6 hours, and then treated with double distilled water, different doses of the test compounds of Example 1 and Example 2 by gavage. 30 minutes after administration, the oral glucose tolerance test was conducted. The results showed that the blood glucose level in the control group increased significantly after 2.5 g/kg glucose had administered by gavage, and reached the peak at 30 minutes. At each dose of SHR1039 (i.e, the compound of Example 1), the blood glucose level was significantly lower than the control group at 30 minutes after the administration of glucose (P<0.01), and the percentage of blood glucose thereof had decreased by 26.10%, 30.24% and 32.05% respectively. At low, middle and high doses of SHR1040 (i.e., the compound of Example 2), the blood glucose level was significantly lower than the control group at 30 minutes (P<0.01), and the percentage of blood glucose had decreased by 24.51%, 26.96% and 27.75%.

Conclusion:

Two experimental results of this report show that the test compounds of Example 1 and Example 2 have significant hypoglycemic effect on normal ICR mice in the oral glucose tolerance tests. Moreover, the test compound of Example 1 shows a better dose-effect relationship.

Effects of DPP-IV Inhibitors on Oral Glucose Tolerance in KKAy Mice

Objective:

To observe the DPP-IV inhibitory effects of the compounds of Example 1 and Example 2 on oral glucose tolerance tests in type II diabetes KKAy mice, a preliminary evaluation of their hypoglycemic effect in vivo was performed.

Test Animals:
 Species, Strains: KKAy mice
 Source: Shanghai Laboratory Animal Center, Chinese Academy of Sciences. Certification No.: SYXK (Shanghai) 2004-2005
 Weight: 40~55 g
 Sex: female: 52; male: 33
 Raising Conditions: SPF grade animal room raising, temperature: 22-24° C.;
 humidity: 45-80%; illumination: 150-300 Lx, day and night cycle with an interval of 12 hours.
Drugs:
 Name: the compounds of Example 1 and Example 2
 Preparation Method: Compounds were Weighed Accurately, then Dissolved in double distilled water, and fully mixed to prepare a 3 mg/mL suspension, then diluted to 1, 0.3, 0.1 mg/mL transparent solutions respectively.
 Dose: 1, 3, 10, 30 mg/kg by gavage. The volume is 10 mL/kg.
Methods:
The Effects of the Compounds on Blood Glucose in KKAy Mice
 Normal KKAy mice had been fasted for 6 hours, and then were randomly grouped according to the weights and fasting blood glucose, 5 mice in each group. The groups included a blank control group as well as different doses of the treatment groups as follows:
 Test 1: male 0704
 Blank control: double-distilled water by gavage
 HR1039: the compound of Example 1, 10 mg/kg by gavage
 the compound of Example 1, 30 mg/kg by gavage
 Test 2: female 0816
 Blank control: double-distilled water by gavage
 SHR1039: the compound of Example 1, 3 mg/kg by gavage
 the compound of Example 1, 10 mg/kg by gavage
 Test 3: male 0712
 Black control: double-distilled water by gavage
 SHR1040: the compound of Example 2, 3 mg/kg by gavage
 the compound of Example 2, 10 mg/kg by gavage
 Test 4: female 0907
 Black control: double-distilled water by gavage
 SHR1040: the compound of Example 2, 3 mg/kg by gavage
 the compound of Example 2, 10 mg/kg by gavage
 Animals in each group had been fasted for 6 hours, and then pretreated with compounds or double distilled water by gavage respectively in single administration. 30 minutes later, animals were administered 2.5 g/kg (female KKAy mice) or 1.5 g/kg (male KKAy mice) glucose by gavage. After administration of glucose at 0, 30, 60 and 120 minutes, serum glucose levels were measured by a glucometer.
Data Processing and Statistical Analysis:
 3. Mean±SD and Student-t test, or Anova was used in statistical analysis.
 4. The percentage of declines in blood glucose after 30 minutes of sugar administrations and the area under the curve (AUC) were calculated.
Results:
1. Compound of Example 1: Test 1, 2
 Male KKAy mice were fasted for 6 hours, and then treated with double distilled water and different doses of the test compound of Example 1 by gavage. 30 minutes after administration, the oral glucose tolerance test was conducted. The results showed that the blood glucose level in the control group increased significantly after 1.5 g/kg glucose had been administered by gavage, and reached the peak at 30 minutes. In the doses of 10 mg/kg and 30 mg/kg of the compound of Example 1 groups, blood glucose levels were both lower than the control group 30 minutes after the administration of glucose. Compared with the control group, the percentage of blood glucose had decreased by 16.22% and 17.15% respectively.
 Female KKAy mice were fasted for 6 hours, and then treated with double distilled water and different doses of the test compound of Example 1 by gavage. 30 minutes after administration, the oral glucose tolerance test was conducted. The results showed that the blood glucose level in the control group increased significantly after 2.5 g/kg glucose had administered by gavage, and reached the peak at 30 minutes. In the doses of 3 mg/kg and 10 mg/kg of the compound of Example 1 groups, blood glucose levels were both significantly lower than the control group 30 minutes after the administration of glucose. The percentage of blood glucose had decreased by 40.63% and 24.68% respectively.
2. Compound of Example 2: Test 3, 4
 Male KKAy mice were fasted for 6 hours, and then treated with double distilled water and different doses of the test compound of Example 2 by gavage. 30 minutes after administration, the oral glucose tolerance test was conducted. The results showed that the blood glucose level in the control group increased significantly after 1.5 g/kg glucose had been administered by gavage, and reached the peak at 30 minutes. In the doses of 10 mg/kg and 30 mg/kg of the compound of Example 2 groups, blood glucose levels were both lower than the control group 30 minutes after the administration of glucose. Compared with the control group, the percentage of blood glucose had decreased by 13.79% and 12.23% respectively.
 Female KKAy mice were fasted for 6 hours, and then treated with double distilled water and different doses of the test of compound Example 2 by gavage. 30 minutes after administration, the oral glucose tolerance test was conducted. The results showed that the blood glucose level in the control group increased significantly after 2.5 g/kg glucose had been administrated by gavage, and reached the peak at 30 minutes. In the dose of 10 mg/kg of the compound of Example 2 group, blood glucoses were lower than control group at 30 minutes after the administration of glucose (P=0.075, ANOVA). The percentage of blood glucose had decreased by 21.55%. However, since there is a great individual difference in the mice, the results had no significant difference.
Conclusion:
 The test compounds of Example 1 and Example 2 both have some hypoglycemic effects on oral glucose tolerance test in type II diabetes KKAy mice.

What is claimed is:

1. A compound of formula (I) or a pharmaceutically acceptable salt thereof:

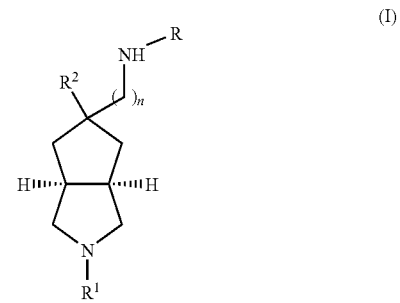

95 wherein:

R is the following formula:

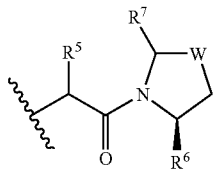

wherein:
- R⁵ is selected from the group consisting of hydrogen, alkyl, cycloalkyl, aryl, heteroaryl and heterocyclic alkyl, wherein the alkyl, cycloalkyl, aryl, heteroaryl or heterocyclic alkyl is independently unsubstituted or substituted with one or more groups independently selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclic alkyl, heterocyclic alkoxyl, carboxylic acid and carboxylic ester;
- R⁶ and R⁷ are each independently selected from the group consisting of hydrogen, alkyl, aryl, heteroaryl, haloalkyl, haloalkoxyl, hydroxy, amino, cyano, alkynyl, alkoxyl, aryloxyl, hydroxyalkyl, heterocyclic alkyl, carboxylic acid, carboxylic ester and halogen; and
- W is C, S or O, wherein C is unsubstituted or substituted with R⁶ or R⁷
- R¹ is selected from the group consisting of —C(O)NR³R⁴, —C(O)R³ and —C(O)OR³;
- R² is selected from the group consisting of hydrogen, unsubstituted or substituted cycloalkyl, and alkyl, wherein the alkyl is unsubstituted or substituted with one or more groups independently selected from the group consisting of cycloalkyl and aryl;
- R³ and R⁴ are either each independently selected from the group consisting of hydrogen, alkyl, cycloalkyl, aryl, heteroaryl and heterocyclic alkyl, wherein the alkyl, cycloalkyl, aryl, heteroaryl or heterocyclic alkyl is independently unsubstituted or substituted with one or more groups independently selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclic alkyl, heterocyclic alkoxyl, trifluoromethyl, carboxylic acid and carboxylic ester;
- or R³ and R⁴, together with the N atom to which they are attached, form a 3- to 8-membered heterocyclic ring, wherein the 3- to 8-membered heterocyclic ring further contains zero or more heteroatoms selected from N, O and S, and the 3- to 8-membered ring is unsubstituted or substituted with one or more groups independently selected from the group consisting of alkyl, aryl, heteroaryl, haloalkyl, haloalkoxyl, hydroxyl, amino, cyano, alkoxyl, aryloxyl, hydroxyalkyl, heterocyclic alkyl, carboxylic acid, carboxylic ester, and halogen; and
- n is an integer from 0 to 4.

2. The compound of claim 1, or a pharmaceutically acceptable salt thereof, which is the compound of formula (IA) or a pharmaceutically acceptable salt thereof:

96

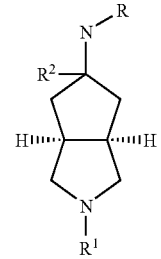

(IA)

wherein:

R is the following formula:

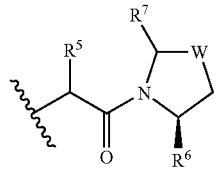

wherein:
- R⁵ is selected from the group consisting of hydrogen, alkyl, cycloalkyl, aryl, heteroaryl and heterocyclic alkyl, wherein the alkyl, cycloalkyl, aryl, heteroaryl or heterocyclic alkyl is independently unsubstituted or substituted with one or more groups independently selected from the group consisting of alkyl, cycloalkyl, aryl, heteroaryl, alkoxyl, cycloalkoxyl, aryloxyl, heteroaryloxy, halogen, hydroxyl, amino, alkylamino, cyano, hydroxyalkyl, heterocyclic alkyl, heterocyclic alkoxyl, carboxylic acid and carboxylic ester;
- R⁶ and R⁷ are each independently selected from the group consisting of hydrogen, alkyl, aryl, heteroaryl, haloalkyl, haloalkoxyl, hydroxy, amino, cyano, alkynyl, alkoxyl, aryloxyl, hydroxyalkyl, heterocyclic alkyl, carboxylic acid, carboxylic ester and halogen; and
- W is C, S or O, wherein C is unsubstituted or substituted with R⁶ or R⁷
- R¹ is selected from the group consisting of —C(O)NR³R⁴, —C(O)R³ and —C(O)OR³;
- R² is selected from the group consisting of hydrogen, unsubstituted or substituted cycloalkyl, and alkyl, wherein the alkyl is unsubstituted or substituted with one or more groups independently selected from the group consisting of cycloalkyl and aryl;
- R³ and R⁴ are either each independently selected from the group consisting of hydrogen, alkyl, cycloalkyl, aryl, heteroaryl and heterocyclic alkyl, wherein the alkyl, cycloalkyl, aryl, heteroaryl or heterocyclic alkyl is independently unsubstituted or substituted with one or more groups independently selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclic alkyl, heterocyclic alkoxyl, trifluoromethyl, carboxylic acid and carboxylic ester; and
- or R³ and R⁴, together with the N atom to which they are attached, may form a 3- to 8-membered heterocyclic ring, wherein the 3- to 8-membered heterocyclic ring contains zero or more heteroatoms selected from N, O and S, and the 3- to 8-membered ring is unsubstituted or substituted with one or more groups independently selected from the group consisting of alkyl, aryl, heteroaryl, haloalkyl, haloalkoxyl, hydroxyl, amino, cyano, alkoxyl, aryloxyl, hydroxyalkyl, heterocyclic alkyl, carboxylic acid, carboxylic ester, and halogen.

3. The compound of claim 1, or a pharmaceutically acceptable salt thereof, which is the compound of formula (IB) or a pharmaceutically acceptable salt thereof:

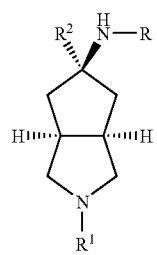

(IB)

wherein:
R is the following formula:

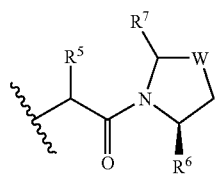

R$^1$ is selected from the group consisting of —C(O)NR$^3$R$^4$, —C(O)R$^3$ and —C(O)OR$^3$;
R$^2$ is selected from the group consisting of hydrogen, unsubstituted or substituted cycloalkyl, and alkyl, wherein the alkyl is unsubstituted or substituted with one or more groups independently selected from the group consisting of cycloalkyl and aryl;
R$^3$ and R$^4$ are either each independently selected from the group consisting of hydrogen, alkyl, cycloalkyl, aryl, heteroaryl and heterocyclic alkyl, wherein the alkyl, cycloalkyl, aryl, heteroaryl or heterocyclic alkyl is independently unsubstituted or substituted with one or more groups independently selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclic alkyl, heterocyclic alkoxyl, trifluoromethyl, carboxylic acid and carboxylic ester;
or R$^3$ and R$^4$, together with the N atom to which they are attached, may form a 3- to 8-membered heterocyclic ring, wherein the 3- to 8-membered heterocyclic ring contains zero or more heteroatoms selected from N, O and S, and the 3- to 8-membered ring is unsubstituted or substituted with one or more groups independently selected from the group consisting of alkyl, aryl, heteroaryl, haloalkyl, haloalkoxyl, hydroxyl, amino, cyano, alkoxyl, aryloxyl, hydroxyalkyl, heterocyclic alkyl, carboxylic acid, carboxylic ester, and halogen;
R$^5$ is selected from the group consisting of hydrogen, alkyl, cycloalkyl, aryl, heteroaryl and heterocyclic alkyl, wherein the alkyl, cycloalkyl, aryl, heteroaryl or heterocyclic alkyl is independently unsubstituted or substituted with one or more groups independently selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclic alkyl, heterocyclic alkoxyl, carboxylic acid and carboxylic ester;
R$^6$ and R$^7$ are each independently selected from the group consisting of hydrogen, alkyl, aryl, heteroaryl, haloalkyl, haloalkoxyl, hydroxyl, amino, cyano, alkynyl, alkoxyl, aryloxyl, hydroxyalkyl, heterocyclic alkyl, carboxylic acid, carboxylic ester and halogen; and
W is C, S or O, wherein C is unsubstituted or substituted with R$^6$ or R$^7$.

4. The compound of claim 1, or a pharmaceutically acceptable salt thereof, which is the compound of formula (IC) or a pharmaceutically acceptable salt thereof:

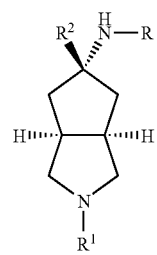

(IC)

wherein:
R is the following formula:

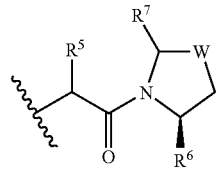

R$^1$ is selected from the group consisting of —C(O)NR$^3$R$^4$, —C(O)R$^3$ and —C(O)OR$^3$;
R$^2$ is selected from the group consisting of hydrogen, unsubstituted or substituted cycloalkyl, and alkyl, wherein the alkyl is independently unsubstituted or substituted with one or more groups independently selected from the group consisting of cycloalkyl and aryl;
R$^3$ and R$^4$ are each independently selected from the group consisting of hydrogen, alkyl, cycloalkyl, aryl, heteroaryl and heterocyclic alkyl, wherein the alkyl, cycloalkyl, aryl, heteroaryl or heterocyclic alkyl is independently unsubstituted or substituted with one or more groups independently selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclic alkyl, heterocyclic alkoxyl, trifluoromethyl, carboxylic acid and carboxylic ester;
or R$^3$ and R$^4$, together with the N atom to which they are attached, may form a 3- to 8-membered heterocyclic ring, wherein the 3- to 8-membered heterocyclic ring contains zero or more heteroatoms selected from N, O and S, and the 3- to 8-membered ring is unsubstituted or substituted with one or more groups independently selected from the group consisting of alkyl, aryl, heteroaryl, haloalkyl, haloalkoxyl, hydroxyl, amino, cyano, alkoxyl, aryloxyl, hydroxyalkyl, heterocyclic alkyl, carboxylic acid, carboxylic ester, and halogen;

R⁵ is selected from the group consisting of hydrogen, alkyl, cycloalkyl, aryl, heteroaryl and heterocyclic alkyl, wherein the alkyl, cycloalkyl, aryl, heteroaryl or heterocyclic alkyl is independently unsubstituted or substituted with one or more groups independently selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclic alkyl, heterocyclic alkoxyl, carboxylic acid and carboxylic ester;

R⁶ and R⁷ are each independently selected from the group consisting of hydrogen, alkyl, aryl, heteroaryl, haloalkyl, haloalkoxyl, hydroxyl, amino, cyano, alkynyl, alkoxyl, aryloxyl, hydroxyalkyl, heterocyclic alkyl, carboxylic acid, carboxylic ester and halogen; and W is C, S or O, wherein C is unsubstituted or substituted with R⁶ or R⁷.

5. The compound of claim 1, or a pharmaceutically acceptable salt thereof, wherein the salt is selected from the group consisting of a hydrochloride salt, a p-toluenesulfonate salt, a tartrate salt, a malate salt, a lactate salt, a methanesulfonate salt, a sulfate salt, a phosphate salt, a citrate salt, an acetate salt, and a trifluoroacetate salt.

6. The compound of claim 5, or a pharmaceutically acceptable salt thereof, wherein the salt is selected from the group consisting of a hydrochloride salt, a p-toluenesulfonate salt, a tartrate salt, and a trifluoroacetate salt.

7. The compound of claim 1, or a pharmaceutically acceptable salt thereof, which is selected from the group consisting of:

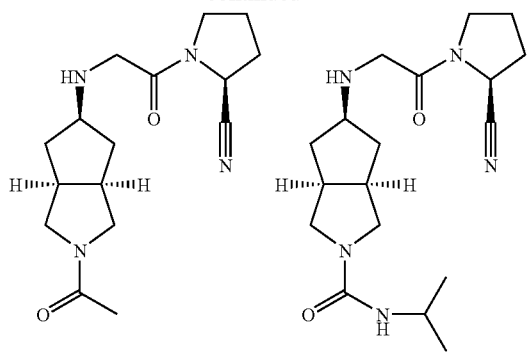

-continued

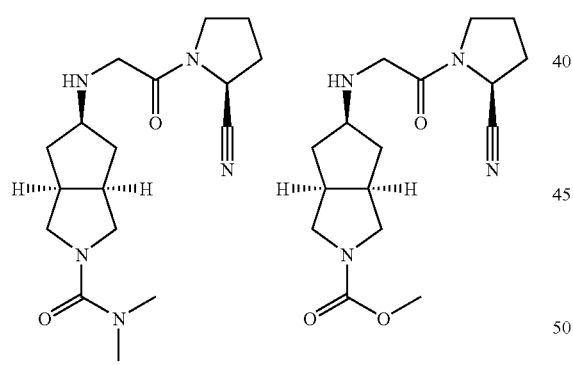

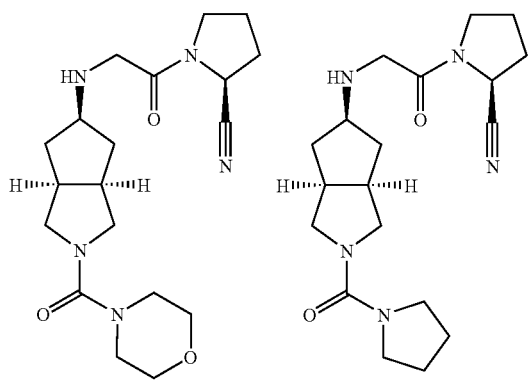

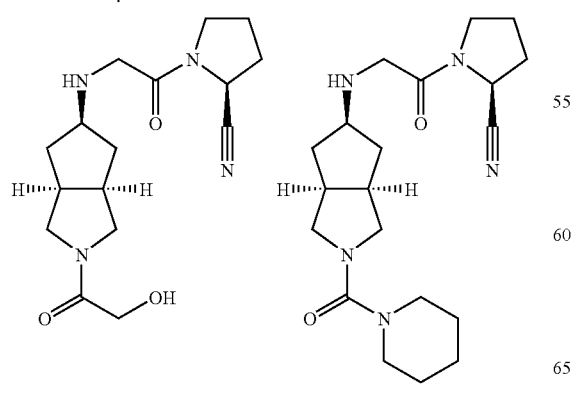

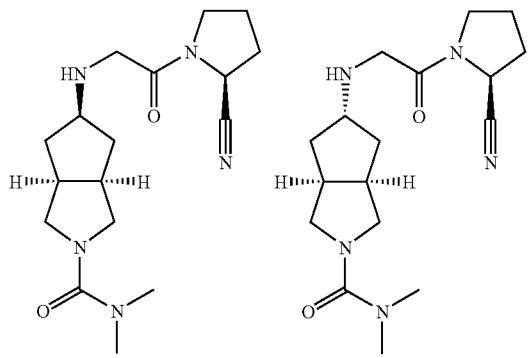

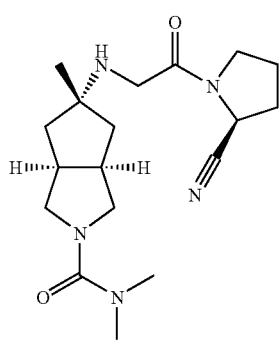

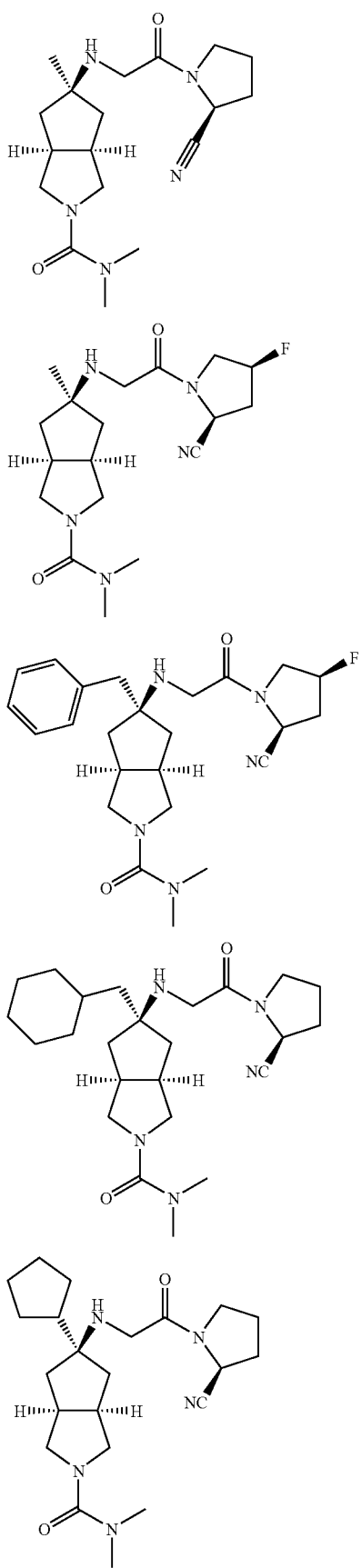

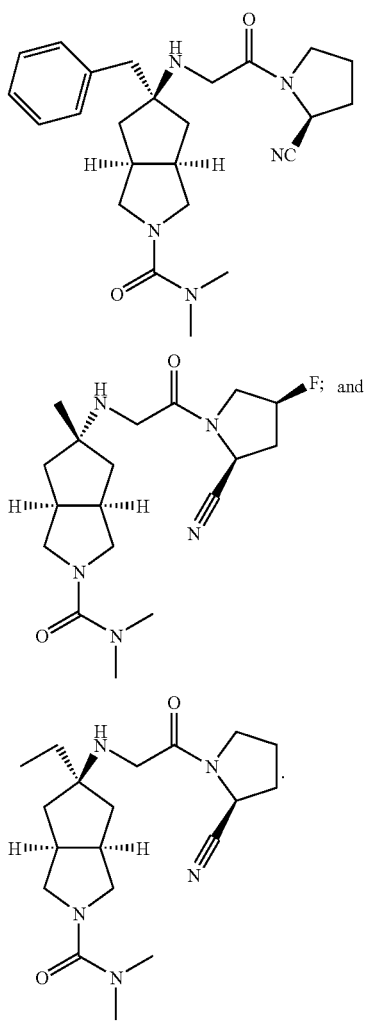

8. A pharmaceutical composition comprising a therapeutically effective amount of the compound of claim 1.

9. A process for preparing the compound of formula (IB) of claim 3, comprising the step of:

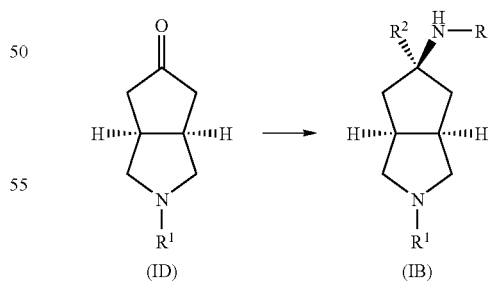

converting the compound of formula (ID) the compound of formula (IB).

10. A process of claim 9, wherein the converting is carried out in methanol or ethanol.

11. A process for preparing the compound of formula (IC) of claim 4, comprising the steps of:

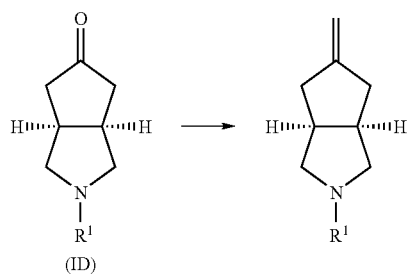

converting the compound of formula (ID) to an azabicyclo alkenyl compound;

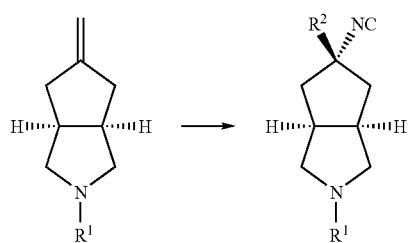

converting the azabicyclo alkenyl compound an azabicyclo cyano compound;

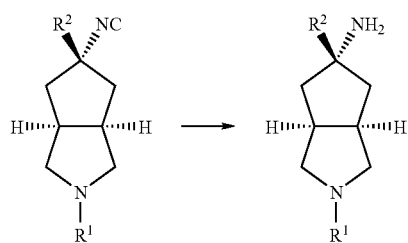

converting the azabicyclo cyano compound to an azabicyclo amine compound; and

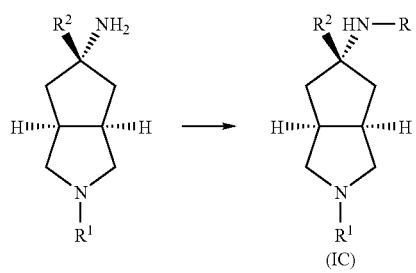

reacting the azabicyclo amine compound with a halo substituted compound to obtain the compound of formula (IC).

12. A process of claim 11, wherein the converting of the azabicyclo alkenyl compound is carried out in the presence of dichloromethane, and the converting of the azabicyclo cyano compound is carried out in the presence of ethanol and hydrochloric acid.

13. A process for preparing the compound of formula (IB) of claim 3, comprising the steps of:

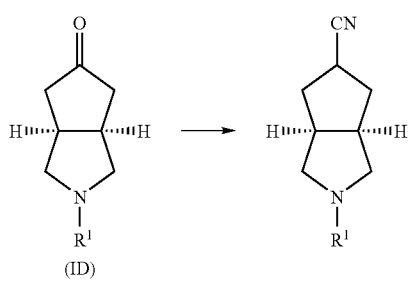

converting the compound of formula (ID) to an azabicyclo cyano compound;

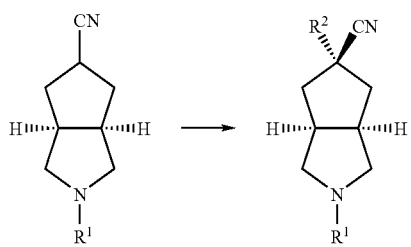

converting the azabicyclo cyano compound to a $R^2$ substituted azabicyclo cyano compound;

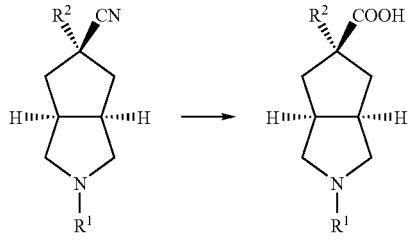

converting the $R^2$ substituted azabicyclo cyano compound to a $R^2$ substituted azabicyclo carboxyl compound;

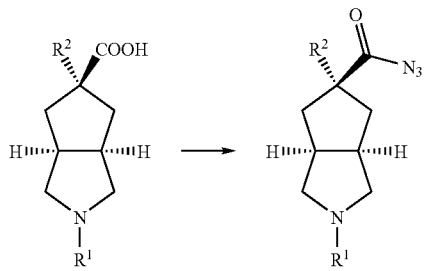

converting the $R^2$ substituted azabicyclo carboxyl compound a substituted azabicyclo azido compound;

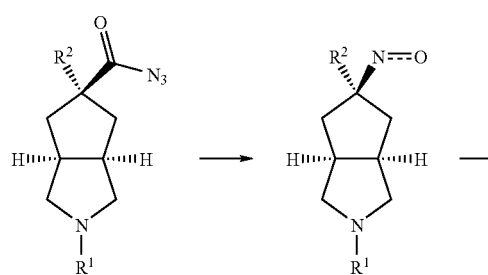

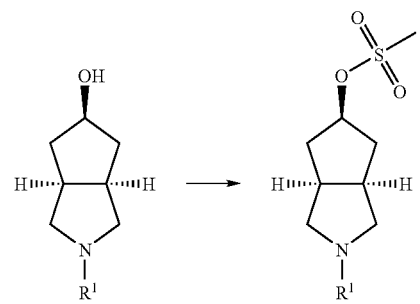

converting the azabicyclo hydroxyl compound to an azabicyclo methyl sulfonic acid compound;

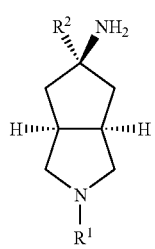

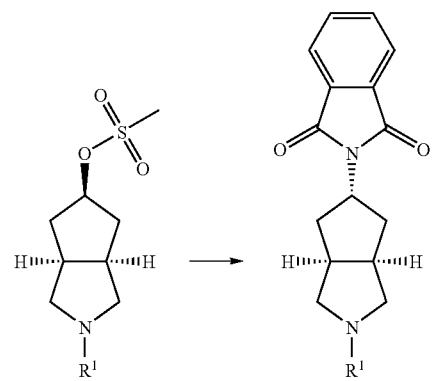

converting the azabicyclo azido compound to a R² substituted azabicyclo amine compound; and converting the azabicyclo methyl sulfonic acid compound to a phthalimide substituted azabicyclo compound;

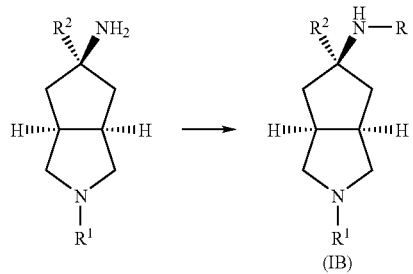

(IB)

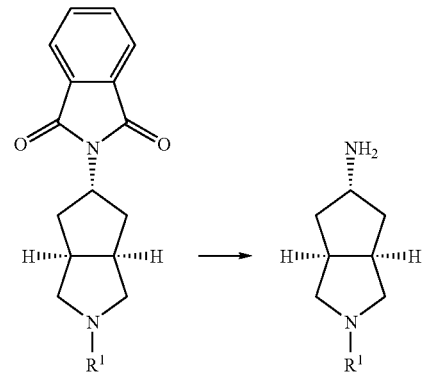

converting the R² substituted azabicyclo amine compound to the compound of formula (IB).

14. A process for preparing the compound of formula (IC) of claim 4, comprising the following steps of:

converting the phthalimide substituted azabicyclo compound to an azabicyclo amine compound; and

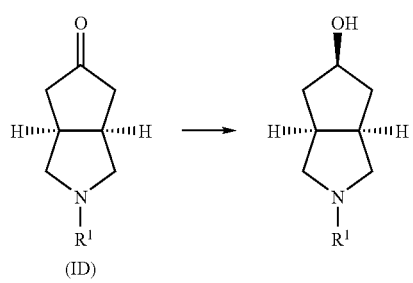

(ID)

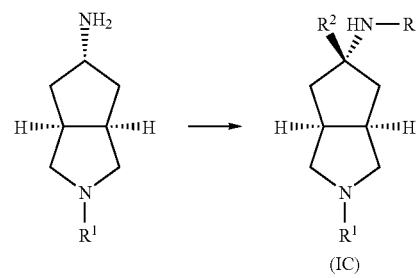

(IC)

reducing the intermediate of formula (ID) to an azabicyclo hydroxyl compound;

converting the azabicyclo amine compound to the compound of formula (IC).

15. A process of claim 14, wherein the reducing is carried out in the presence of lithium tri-tert-butoxyaluminum hydride.

16. A preparation process of claim 11 or 13, further comprising the step of reacting the compound of formula (IB) or formula (IC) with an acid to obtain an acid addition salt.

17. A method of inhibiting a dipeptidyl peptidase comprising administering the compound or pharmaceutically acceptable salt thereof of claim 1 to a patient in need of the treatment.

18. A method of inhibiting a dipeptidyl peptidase comprising administering the composition of claim 8 to a patient in need of the treatment.

19. The compound of claim 1, or a pharmaceutically acceptable salt thereof, wherein $R^3$ and $R^4$ are independently selected from the group consisting of hydrogen, alkyl, and hydroxylalkyl.

20. The compound of claim 1, or a pharmaceutically acceptable salt thereof, wherein $R^1$ is —C(O)NR$^3$R$^4$.

21. The compound of claim 1, or a pharmaceutically acceptable salt thereof, wherein $R^1$ is selected from the group consisting of —C(O)N(CH$_3$)$_2$, —C(O)NCH$_2$(CH$_3$)$_2$, —C(O)CH$_3$, —C(O)OCH$_3$, and —C(O)CH$_2$OH.

22. The compound of claim 1, or a pharmaceutically acceptable salt thereof, wherein $R^2$ is selected from the group consisting of hydrogen, and unsubstituted or substituted alkyl.

23. The compound of claim 1, or a pharmaceutically acceptable salt thereof, wherein $R^2$ is selected from the group consisting of hydrogen, methyl, ethyl, cyclohexylmethyl, cyclopentyl, and benzyl.

24. The compound of claim 23, or a pharmaceutically acceptable salt thereof, wherein $R^2$ is methyl or ethyl.

25. The compound of claim 1, or a pharmaceutically acceptable salt thereof, wherein $R^5$ is hydrogen.

26. The compound of claim 1, or a pharmaceutically acceptable salt thereof, wherein at least one of $R^6$ and $R^7$ is hydrogen.

27. The compound of claim 1, or a pharmaceutically acceptable salt thereof, wherein at least one of $R^6$ and $R^7$ is cyano.

28. The compound of claim 1, or a pharmaceutically acceptable salt thereof, wherein W is C.

29. The compound of claim 28, or a pharmaceutically acceptable salt thereof, wherein W is halogen-substituted C.

30. The compound of claim 1, or a pharmaceutically acceptable salt thereof, which is selected from the group consisting of:

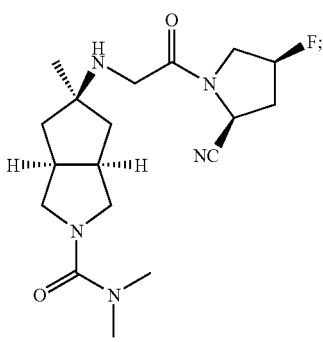

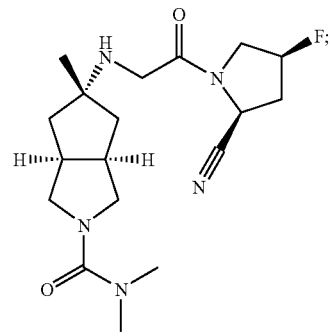

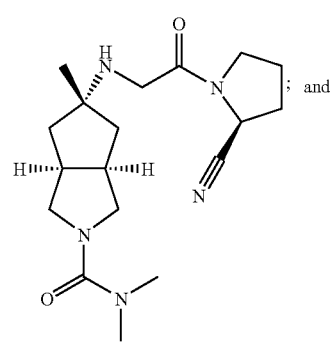

; and

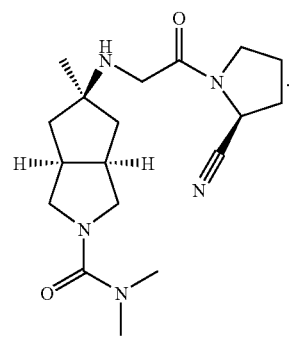

.

31. The preparation process of claim 13, further comprising the step of reacting the compound of formula (IB) with an acid to obtain an acid addition salt.

32. A method of inhibiting dipeptidyl peptidase-IV in a mammal in need thereof comprising the step of administering a therapeutically effective amount of the compound of claim 1, or a pharmaceutically acceptable salt thereof.

33. A method of treating type II diabetes comprising administering to a mammal in need thereof a therapeutically effective amount of the compound of claim 1, or a pharmaceutically acceptable salt thereof.

\* \* \* \* \*